US012569616B2

(12) United States Patent
Agard et al.

(10) Patent No.: US 12,569,616 B2
(45) Date of Patent: Mar. 10, 2026

(54) MULTI-USE DRUG-DELIVERY DEVICE

(71) Applicant: Eli Lilly and Company, Indianapolis, IN (US)

(72) Inventors: Ryan Michael Agard, Royersford, PA (US); Matthew James Clemente, Carmel, IN (US); Nicholas Joseph Ciccarelli, Newton Square, PA (US); Daniel Scott Davenport, Collegeville, PA (US); Shaun Robert Devitt, Wayne, PA (US); Andrew Nathan King, King of Prussia, PA (US)

(73) Assignee: Eli Lilly and Company, Indianapolis, IN (US)

( * ) Notice: Subject to any disclaimer, the term of this patent is extended or adjusted under 35 U.S.C. 154(b) by 945 days.

(21) Appl. No.: 17/783,833

(22) PCT Filed: Dec. 4, 2020

(86) PCT No.: PCT/US2020/063405
§ 371 (c)(1),
(2) Date: Jun. 9, 2022

(87) PCT Pub. No.: WO2021/118888
PCT Pub. Date: Jun. 17, 2021

(65) Prior Publication Data
US 2023/0009541 A1 Jan. 12, 2023

Related U.S. Application Data

(60) Provisional application No. 62/947,836, filed on Dec. 13, 2019.

(51) Int. Cl.
| | |
|---|---|
| *A61M 5/158* | (2006.01) |
| *A61M 5/142* | (2006.01) |
| *A61M 5/168* | (2006.01) |

(52) U.S. Cl.
CPC ............ *A61M 5/158* (2013.01); *A61M 5/142* (2013.01); *A61M 5/168* (2013.01); *A61M 2005/1585* (2013.01)

(58) Field of Classification Search
CPC ...... A61M 5/158; A61M 5/142; A61M 5/168; A61M 2005/1585; A61M 5/14248;
(Continued)

(56) References Cited

U.S. PATENT DOCUMENTS

| | | | |
|---|---|---|---|
| 1,004,611 A | 10/1911 | White | |
| 9,149,578 B2 | 10/2015 | Byerly | |

(Continued)

FOREIGN PATENT DOCUMENTS

| | | |
|---|---|---|
| JP | 2013544153 | 12/2013 |
| JP | 2014502887 | 2/2014 |

(Continued)

OTHER PUBLICATIONS

Patent Cooperation Treaty International Search Report pertaining to International Application No. PCT/US2020/063405; International Filing Date: Dec. 4, 2020; Date of Mailing Mar. 22, 2021.

(Continued)

*Primary Examiner* — James D Ponton
(74) *Attorney, Agent, or Firm* — Arthur Shum

(57) ABSTRACT

A drug-delivery device is provided including a drug reservoir configured to contain a fluid drug, a needle cartridge comprising a plurality of needle assemblies, a drive member, a pump, one or more springs, a loading button and a dosing button. The device is configured to use work done by the user in actuating the loading button to load the one or more springs. When the user actuates the dosing button after actuating the loading button, the device is configured to (i) release the one or more loaded springs to operate the drive member to drive a needle assembly that is in operational (Continued)

alignment with the drive member from a retracted position to an injection position, (ii) drive the pump to pump fluid drug from the drug reservoir through the driven needle assembly, and (iii) retract the driven needle assembly from the injection position to the retracted position.

37 Claims, 37 Drawing Sheets

(58) Field of Classification Search
CPC ......... A61M 2005/14256; A61M 2005/14506; A61B 5/15146; A61B 5/15117
See application file for complete search history.

(56) References Cited

U.S. PATENT DOCUMENTS

| | | | | |
|---|---|---|---|---|
| 9,981,088 | B2 | 5/2018 | Byerly | |
| 2007/0299458 | A1* | 12/2007 | Epple | A61B 5/15113 |
| | | | | 606/181 |
| 2009/0062747 | A1 | 3/2009 | Saul | |
| 2016/0051755 | A1 | 2/2016 | Lin | |
| 2016/0199590 | A1 | 7/2016 | Schabbach et al. | |
| 2016/0213838 | A1 | 7/2016 | Schabbach et al. | |
| 2016/0213840 | A1 | 7/2016 | Schabbach et al. | |
| 2016/0354553 | A1 | 12/2016 | Anderson et al. | |

FOREIGN PATENT DOCUMENTS

| | | |
|---|---|---|
| JP | 2014531961 | 12/2014 |
| JP | 2019513463 | 5/2019 |
| WO | 2006003130 | 1/2006 |
| WO | 12068321 | 5/2012 |
| WO | 12085032 | 6/2012 |
| WO | 13057032 | 4/2013 |
| WO | 2017139741 | 8/2017 |

OTHER PUBLICATIONS

Patent Cooperation Treaty Written Opinion of the International Searching Authority pertaining to International Application No. PCT/US2020/063405; International Filing Date: Dec. 4, 2020; Date of Mailing: Mar. 22, 2021.

* cited by examiner

MULTI-USE DRUG-DELIVERY DEVICE

FIELD OF THE DISCLOSURE

The present disclosure relates to devices and methods for delivering drugs. More particularly, the present disclosure relates to a multi-use drug-delivery device.

BACKGROUND OF THE DISCLOSURE

Some drug-delivery devices, such as autoinjectors, store potential energy in compression springs which are released at the time of device actuation. This stored energy is used to drive various functions of such drug-delivery devices, such as needle insertion into the patient and ejection of fluid from a drug reservoir. However, long-term potential energy storage in springs can be problematic because resultant forces from compressed springs can cause device material deformation over the shelf life of a device. Furthermore, basic physics and material properties require that springs adequate for storing sufficient potential energy to drive the previously-mentioned functions in a drug-delivery device over the shelf life of the device be of a certain minimum size, which can increase device size. Ideally, springs should remain unstressed or minimally stressed over the shelf life of a device, and then be loaded and released in a relatively short period of time during device use.

SUMMARY

Various aspects are described in this disclosure, which include, but are not limited to, the following aspects:

1. A drug-delivery device, comprising: a housing; a drug reservoir within the housing configured to contain a drug fluid; a drive member; a needle assembly disposed in a retracted position within the housing; a pump in fluid communication with the drug reservoir; one or more springs; a loading button coupled to the housing configured to be manually actuated to load the one or more springs using work done through actuation of the loading button; and a dosing button coupled to the housing configured to be manually actuated after actuation of the loading button to release the one or more loaded springs to: operate the drive member to drive the needle assembly from the retracted position to an injection position, drive the pump to pump the drug fluid from the drug reservoir through the driven needle assembly, and retract the driven needle assembly from the injection position to the retracted position.

2. The device of aspect 1, further comprising the drug fluid contained within the drug reservoir.

3. The device of any of aspects 1-2, wherein the needle assembly includes a first needle assembly of a plurality of needle assemblies, and the plurality of needle assemblies is disposed in a needle cartridge within the housing.

4. The device of aspect 3, wherein actuation of the loading button advances the needle cartridge so that a second needle assembly of the plurality of needle assemblies is moved out of operational alignment with the drive member and the first needle assembly is moved into operational alignment with the drive member.

5. The device of any of aspects 1-4, further comprising an unlocking button configured to prevent actuation of the dosing button until the unlocking button is moved to an unlocked configuration.

6. The device of any of aspects 1-5, wherein: the one or more springs comprise one or more linear springs movable between an axially expanded configuration and an axially compressed configuration; actuation of the loading button loads the one or more linear springs by moving the one or more linear springs to the axially compressed configuration; and actuation of the dosing button after actuation of the loading button releases the one or more linear springs by moving the one or more linear springs to the axially expanded configuration to operate the drive member.

7. The device of any of aspects 1-6, wherein: the one or more springs comprise one or more clock springs movable between an unwound configuration and a wound configuration; actuation of the loading button loads the one or more clock springs by moving the one or more clock springs to the wound configuration using work done through actuation of the loading button, and actuation of the dosing button after actuation of the loading button releases the one or more clock springs by moving the one or more clock springs to the unwound configuration to drive the pump.

8. The device of any of aspects 1-7, wherein: the one or more springs comprise a first linear spring and a second linear spring, each movable between an axially expanded configuration and an axially compressed configuration; the device further comprises a primary slide and a secondary slide, wherein: the primary slide is configured to slidably move parallel to a linear axis of the device between a first primary slide position and a second primary slide position, the secondary slide is configured to slidably move parallel to the linear axis between a first secondary slide position and a second secondary slide position, the primary slide is coupled to the first linear spring, and the secondary slide is coupled to both of the first linear spring and the second linear spring; the device further comprises a blocker that, until released, is configured to prevent the primary slide from moving from the first primary slide position to the second primary slide position; actuation of the loading button moves the secondary slide from the first secondary slide position to the second secondary slide position to move both of the first linear spring and the second linear spring to the axially compressed configuration; and actuation of the dosing button after actuation of the loading button releases the blocker to allow the first linear spring to move to the axially expanded configuration, wherein movement of the first linear spring to the axially expanded configuration moves the primary slide from the first primary slide position to the second primary slide position, and wherein movement of the primary slide to the second primary slide position operates the drive member.

9. The device of aspect 8, further comprising a latch that, until released, is configured to prevent the secondary slide from moving from the second secondary slide position to the first secondary slide position after actuation of the loading button; wherein the latch is configured to be released a predetermined time after the blocker is released to allow the second linear spring to move to the axially expanded configuration, wherein movement of the second linear spring to the axially expanded configuration moves the secondary slide from the second secondary slide position to the first secondary slide position.

10. The device of aspect 9, wherein the primary slide and the secondary slide are coupled such that movement of the secondary slide from the second secondary slide position to the first secondary slide position causes the primary slide to move from the second primary slide position to the first primary slide position, wherein movement of the primary slide to the first primary slide position retracts the driven needle assembly from the injection position to the retracted position.

11. The device of any of aspects 9-10, wherein the device is a re-usable device that, when the primary slide returns to the first primary slide position and the secondary slide returns to the first secondary slide position, is configured to allow a second actuation of the loading button, and then a second actuation of the dosing button after the second actuation of the loading button, to deliver a second dose of the drug fluid.

12. The device of any of aspects 9-11, further comprising a clock spring rotatable between an unwound configuration and a wound configuration, a face gear rotationally locked with the clock spring, and a pawl configured to engage with the face gear, wherein actuation of the loading button loads the clock spring by rotating the face gear in a first rotational direction, wherein rotation of the face gear in the first rotational direction rotates the clock spring to the wound configuration; wherein the pawl is configured to engage with the face gear after rotation of the clock spring to the wound configuration to prevent rotation of the face gear in a second rotational direction opposite the first rotational direction, and to prevent rotation of the clock spring to the unwound configuration; wherein actuation of the dosing button after actuation of the loading button dis-engages the pawl from the face gear to allow the face gear to rotate in the second rotational direction, wherein rotation of the face gear in the second rotational direction rotates the clock spring to the unwound configuration; and wherein rotation of the face gear in the second rotational direction by a predetermined rotational angle releases the latch to allow the second linear spring to move to the axially expanded configuration, wherein movement of the second linear spring to the axially expanded configuration moves the secondary slide from the second secondary slide position to the first secondary slide position.

13. The device of any of aspects 1-12, wherein the pump is a rotary plunger pump.

14. The device of any of aspects 1-13, wherein the device is configured to use only energy released from the one or more loaded springs to operate the drive member, to drive the pump, and to retract the driven needle assembly.

15. A method for operating a drug-delivery device comprising: actuating a loading button of the device to load one or more springs of the device using work done through actuation of the loading button; actuating a dosing button of the device after actuating the loading button to release the one or more loaded springs, wherein releasing the one or more loaded springs: operates a drive member of the device to drive a needle assembly within the device from a retracted position to an injection position, drives a pump of the device to pump drug fluid from a drug reservoir through the driven needle assembly, and retracts the driven needle assembly from the injection position to the retracted position.

16. The method of aspect 15, wherein the drug reservoir is disposed within the device and contains a drug fluid.

17. The method of any of aspects 15-16, wherein the needle assembly is a first needle assembly of a plurality of needle assemblies, and the plurality of needle assemblies is disposed in a needle cartridge.

18. The method of aspect 17, further comprising advancing the needle cartridge in response to actuation by the user of the loading button so that a second needle assembly of the plurality of needle assemblies is moved out of operational alignment with the drive member and the first needle assembly is moved into operational alignment with the drive member.

19. The method of any of aspects 15-18, further comprising actuating an unlocking button of the device to unlock the dosing button for actuation.

20. The method of any of aspects 15-19, wherein only energy released from the one or more loaded springs is used to operate the drive member, drive the pump, and retract the driven needle assembly.

21. A needle-insertion mechanism for a drug-delivery device, the mechanism comprising: a drive member; a needle assembly disposed in a retracted position within a housing of the drug-delivery device; a primary linear spring; a secondary linear spring; a primary slide configured to slidably move parallel to a linear axis of the device between a first primary slide position and a second primary slide position, wherein the primary slide is coupled to the first linear spring; a secondary slide configured to slidably move parallel to the linear axis of the device between a first secondary slide position and a second secondary slide position, wherein the secondary slide is coupled to the first linear spring and the second linear spring; a blocker that, until released, is configured to prevent the primary slide from moving from the first primary slide position to the second primary slide position; a loading button configured to be manually actuated to move the secondary slide from the first secondary slide position to the second secondary slide position using work done through actuation of the loading button to compress both the first linear spring and the second linear spring; and a dosing button configured to be manually actuated after actuation of the loading button to release the blocker to allow the primary slide to move from the first primary slide position to the second primary slide position under biasing pressure from the compressed first linear spring, wherein movement of the primary slide to the second primary slide position operates the drive member to drive the needle assembly from the retracted position to an injection position.

22. The mechanism of aspect 21, wherein: the mechanism further comprises a latch that, until released, is configured to prevent the secondary slide from moving from the second secondary slide position to the first secondary slide position after actuation of the loading button; and the mechanism is configured to release the latch a predetermined time after the release of the blocker to allow the secondary slide to move from the second secondary slide position to the first secondary slide position under biasing pressure from the compressed second linear spring.

23. The mechanism of aspect 22, wherein the primary slide and the secondary slide are coupled such that movement of the secondary slide from the second secondary slide position to the first secondary slide position causes the primary slide to move from the second primary slide position to the first primary slide position, wherein movement of the primary slide to the first primary slide position retracts the driven needle assembly from the injection position to the retracted position.

24. The mechanism of any of aspects 22-23, wherein: the device further comprises a clock spring rotatable between an unwound configuration and a wound configuration, a face gear rotationally locked with the clock spring, and a pawl configured to engage with the face gear; actuation of the loading button loads the clock spring by rotating the face gear in a first rotational direction, wherein rotation of the face gear in the first rotational direction rotates the clock spring to the wound configuration; the pawl is configured to engage with the face gear after rotation of the clock spring to the wound configuration to prevent rotation of the face gear in a second rotational direction opposite the first rotational direction, and to prevent rotation of the clock spring to the unwound configuration; actuation of the dosing button after actuation of the loading button dis-engages the pawl from the face gear to allow the face gear to rotate in the second rotational direction, wherein rotation of the face gear in the second rotational direction rotates the clock spring to the unwound configuration; and rotation of the face gear in the second rotational direction by a predetermined rotational angle, releases the latch to allow the secondary slide to move from the second secondary slide position to the first secondary slide position under biasing pressure from the compressed second linear spring.

25. A method for operating a needle-insertion mechanism for a drug-delivery device, the needle-insertion mechanism comprising a primary slide coupled to a first linear spring, a secondary slide coupled to the first linear spring and a second linear spring, and a blocker that, until released, is configured to prevent the primary slide from moving from a first primary slide position to a second primary slide position, the method comprising: actuating a loading button of the device to move the secondary slide from a first secondary slide position to a second secondary slide position, wherein the movement of the secondary slide axially compresses both the first linear spring and the second linear spring; and actuating a dosing button of the device after actuating the loading button to release the blocker to allow the primary slide to move from the first primary slide position to the second primary slide position under biasing pressure from the compressed first linear spring, wherein movement of the primary slide to the second primary slide position operates a drive member to drive a needle assembly disposed within the device from a retracted position to an injection position.

26. The method of aspect 25, wherein the device further comprises a latch that, until released, prevents the secondary slide from moving from the second secondary slide position to the first secondary slide position after the user has actuated the loading button, the method further comprising: releasing the latch a predetermined time after releasing the blocker so as to allow the secondary slide to move from the second secondary slide position to the first secondary slide position under biasing pressure from the compressed second linear spring.

27. The method of aspect 26, wherein the primary slide and the secondary slide are coupled such that movement of the secondary slide from the second secondary slide position to the first secondary slide position causes the primary slide to move from the second primary slide position to the first primary slide position, wherein movement of the primary slide to the first primary slide position retracts the driven needle assembly from the injection position to the retracted position.

28. The method of any of aspects 25-27, wherein the needle-handling mechanism further comprises a clock spring, a face gear coupled with the clock spring, and a pawl configured to engage with the face gear, the method further comprising: during actuation of the loading button, loading the clock spring by rotationally winding the face gear and the clock spring in a first rotational direction using work done through actuation of the loading button; after loading the clock spring, engaging the pawl with the face gear to prevent the clock spring from unwinding by rotating in a second rotational direction opposite to the first rotational direction; during actuation of the dosing button, dis-engaging the pawl from the face gear to allow the clock spring to unwind by rotating in the second rotational direction; and when the clock spring unwinds by a predetermined rotational angle, releasing the latch so as to allow the secondary slide to move from the second secondary slide position to the first secondary slide position under biasing pressure from the compressed second linear spring.

29. A device for storing and handling needles, the device comprising: a housing; a drive member; a needle cartridge holding a plurality of needle assemblies, each needle assembly disposed in a separate retracted position within the needle cartridge; one or more springs; a loading button coupled to the housing configured to be manually actuated to load the one or more springs using work done through actuation of the loading button, and to advance the needle cartridge so a first needle assembly of the plurality of needle assemblies is moved out of operational alignment with the drive member and a second needle assembly of the plurality of needle assemblies is moved into operational alignment with the drive member; and a dosing button coupled to the housing configured to be manually actuated after actuation of the loading button to release the one or more loaded springs to operate the drive member to drive the second needle assembly from its retracted position within the needle cartridge to an injection position.

30. The device of aspect 29, wherein the device is further configured to, after operating the drive member to drive the second needle assembly to the injection position, retract the second needle assembly to its retracted position using energy released from the one or more springs.

31. The device of any of aspects 29-30, wherein: the needle cartridge comprises a plurality of Geneva wheel members; the device further comprises a Geneva wheel configured to engage with the Geneva wheel members; and the Geneva wheel is configured to rotate in response to actuation of the loading button, wherein engagement between the Geneva wheel and the Geneva wheel members causes the needle cartridge to rotate such that the first needle assembly is moved out of operational alignment with the drive member and the second needle assembly is moved into operational alignment with the drive member.

32. The device of any of aspects 29-31, wherein the device further comprises a drug reservoir configured to contain a drug fluid, and a pump in fluid communication with the drug reservoir.

33. The device of aspect 32, wherein the device is configured to, after operating the drive member to drive the second needle assembly to the injection position, drive the pump to pump the drug fluid from the drug reservoir through the second needle assembly using energy released from the one or more springs.

34. The device of any of aspects 32-33, wherein the pump is a rotary plunger pump.

35. The device of any of aspects 29-34, further comprising an unlocking button configured to prevent actuation of the dosing button until the unlocking button is moved to an unlocked configuration.

36. The device of any of aspects 29-35, wherein the device is configured to use only energy released from the one or more loaded springs to operate the drive member.

37. The device of any of aspects 30-35, wherein the device is configured to use only energy released from the one or more loaded springs to operate the drive member and to retract the second needle assembly.

38. The device of any of aspects 33-35, wherein the device is configured to use only energy released from the one or more loaded springs to operate the drive member and to drive the pump.

39. A method for operating a drug-delivery device comprising one or more springs, a loading button, a dosing button, a drive member, and a needle cartridge holding a plurality of needle assemblies, each needle assembly disposed in a retracted position within the needle cartridge, the method comprising: actuating a loading button of the device to: advance the needle cartridge using work done through actuation of the loading button, such that a first needle assembly of the plurality of needle assemblies is moved out of operational alignment with the drive member and a second needle assembly of the plurality of needle assemblies is moved into operational alignment with the drive member, and load the one or more springs using work done through actuation of the loading button; and actuating a dosing button of the device after actuation of the loading button to release the one or more loaded springs, wherein releasing the one or more loaded springs operates the drive member using energy released from the one or more loaded springs to drive the second needle assembly from its retracted position within the needle cartridge to an injection position.

40. The method of aspect 39, wherein releasing the one or more loaded springs retracts the second needle assembly to its retracted position using energy released from the one or more loaded springs after driving the second needle assembly to the injection position.

41. The method of any of aspects 39-40, wherein: the needle cartridge comprises a plurality of Geneva wheel members; the device further comprises a Geneva wheel configured to engage with the Geneva wheel members; and the Geneva wheel rotates in response to actuation of the loading button, wherein engagement between the Geneva wheel and the Geneva wheel members causes the needle cartridge to rotate such that the first needle assembly is moved out of operational alignment with the drive member and the second needle assembly is moved into operational alignment with the drive member.

42. The method of any of aspects 39-41, wherein the device further comprises a drug reservoir configured to contain a drug fluid, and a pump in fluid communication with the drug reservoir.

43. The method of aspect 42, wherein releasing the one or more loaded springs drives the pump to pump the drug fluid from the drug reservoir through the second needle assembly using energy released from the one or more loaded springs.

44. The method of any of aspects 42-43, wherein the pump is a rotary plunger pump.

45. The method of any of aspects 39-44, further comprising actuation of an unlocking button for unlocking the dosing button.

46. The method of any of aspects 39-45, wherein only energy released from the one or more loaded springs is used to operate the drive member.

47. The method of any of aspects 40-45, wherein only energy released from the one or more loaded springs is used to operate the drive member and to retract the second needle assembly.

48. The method of any of aspects 43-45, wherein only energy released from the one or more loaded springs is used to operate the drive member and to drive the pump.

49. A drug-delivery device, comprising: a housing; a drug reservoir within the housing configured to contain a drug fluid; a pump in fluid communication with the drug reservoir; a needle cartridge holding a plurality of needle assemblies; one or more springs; a loading button coupled to the housing configured to be manually actuated to load the one or more springs using work done through actuation of the loading button and to advance the needle cartridge so a first needle assembly of the plurality of needle assemblies is moved out of a dosing position within the device, and a second needle assembly of the plurality of needle assemblies is moved into the dosing position; and a dosing button coupled to the housing configured to be manually actuated after actuation of the loading button to release the one or more loaded springs to drive the pump to pump the drug fluid from the drug reservoir through the second needle assembly.

50. The device of aspect 49, further comprising a drive member, wherein the dosing position is in operational alignment with the drive member, wherein: actuation of the dosing button after actuation of the loading button releases the one or more loaded springs to operate the drive member to drive the second needle assembly to an injection position.

51. The device of aspect 50, wherein the device is further configured to, after operating the drive member to drive the second needle assembly to the injection position, use energy released from the one or more springs to retract the second needle assembly to the dosing position.

52. The device of any of aspects 49-51, wherein the pump is a rotary plunger pump.

53. The device of any of aspects 49-52, further comprising an unlocking button configured to prevent actuation of the dosing button until the unlocking button is moved to an unlocked configuration.

54. The device of any of aspects 49-53, wherein: the one or more springs comprise one or more clock springs movable between an unwound configuration and a wound configuration; and actuation of the loading button loads the one or more clock springs by moving the one or more clock springs to the wound configuration using work done through actuation of the loading button, and actuation of the dosing button after actuation of the loading button releases the one or more clock springs by moving the one or more clock springs to the unwound configuration to drive the pump.

55. The device of any of aspects 50-54, wherein: the one or more springs comprise one or more linear springs each movable between an axially expanded configuration and an axially compressed configuration; actuation of the loading button moves the one or more linear springs to the axially compressed configuration using work done through actuation of the loading button; and actuation of the dosing button after actuation of the loading button releases the one or more linear springs by allowing them to move to the axially expanded configuration, wherein movement of the one or more linear springs to the axially expanded configuration operates the drive member.

56. The device of any of aspects 49-55, wherein the device is configured to use only energy released from the one or more loaded springs to drive the pump.

57. The device of any of aspects 50-55, wherein the device is configured to use only energy released from the one or more loaded springs to drive the pump and operate the drive member.

58. The device of any of aspects 51-55, wherein the device is configured to use only energy released from the one or more loaded springs to drive the pump, operate the drive member, and retract the second needle assembly.

59. A method for operating a drug-delivery device comprising: actuating a loading button of the device to: advance a needle cartridge of the device using work through actuation of the loading button so a first needle assembly of a plurality of needle assemblies stored within the needle cartridge is moved out of a dosing position within the device and a second needle assembly of the plurality of needle assemblies is moved into the dosing position, and load one or more springs in the device using work done through actuation of the loading button; actuating a dosing button of the device after actuation of the loading button to release the one or more loaded springs to drive a pump using energy released from the one or more loaded springs to pump a drug fluid from a drug reservoir of the device through the second needle assembly.

60. The method of aspect 59, wherein: the device further comprises a drive member; the dosing position is in operational alignment with the drive member; and releasing the one or more loaded springs operates the drive member to drive the second needle assembly to an injection position.

61. The method of aspect 60, wherein releasing the one or more loaded springs retracts the second needle assembly to the dosing position after operating the drive member to drive the second needle assembly to the injection position.

62. The method of any of aspects 59-61, wherein the pump is a rotary plunger pump.

63. The method of any of aspects 59-62, further comprising actuating an unlocking button for unlocking the dosing button.

64. The method of any of aspects 59-63, wherein: the one or more springs comprise one or more clock springs; loading the one or more springs comprise rotationally winding the one or more clock springs; and releasing the one or more loaded springs comprises allowing the one or more clock springs to unwind, and using energy released by the one or more unwinding clock springs to drive the pump.

65. The method of any of aspects 60-64, wherein: the one or more springs comprise one or more linear springs; loading the one or more springs comprise compressing the one or more linear springs; and releasing the one or more springs comprises allowing the one or more linear springs to expand, and using energy released by the one or more expanding linear springs to operate the drive member.

66. The method of any of aspects 59-65, wherein only energy released from the one or more loaded springs is used to drive the pump.

67. The method of any of aspects 60-65, wherein only energy released from the one or more loaded springs is used to drive the pump and to operate the drive member.

68. The method of any of aspects 61-65, wherein only energy released from the one or more loaded springs is used to drive the pump, operate the drive member, and retract the second needle assembly.

BRIEF DESCRIPTION OF THE DRAWINGS

The above-mentioned and other features and advantages of this disclosure, and the manner of attaining them, will become more apparent and will be better understood by reference to the following description of embodiments of the invention taken in conjunction with the accompanying drawings, wherein.

Corresponding reference characters indicate corresponding parts throughout the several views. The exemplifications set out herein illustrate exemplary embodiments of the invention and such exemplifications are not to be construed as limiting the scope of the invention in any manner.

DETAILED DESCRIPTION

The present disclosure relates to drug-delivery devices that store energy as a result of work done by the user to perform steps such as needle cartridge indexing, needle insertion, needle retraction, dosing button unlock, fluid path creation from a reservoir to a patient, and pumping.

According to one aspect of the present disclosure, the devices disclosed herein uses work done by a user in a first actuation step (e.g., by pressing a button) to load one or more springs and to index a needle holding cartridge. A second actuation step by the user releases one or more of the loaded springs (e.g., linear compression springs) to drive a needle into a patient's subcutaneous/intramuscular tissue. This step also releases one or more of the loaded springs (e.g., one or more coiled clock springs) to drive a gear train, whose output torque rotates a pump (e.g., a rotary plunger pump). This pump in turn draws fluid from a reservoir and delivers it to the patient. At the end of the dose, further energy from the one or more loaded springs is released to retract the needle and reset the device. An on-body sensing button and associated lock mechanism decreases the chances of the user inadvertently triggering the second actuation step by mechanically locking out the device and preventing the user from triggering the second actuation step until the device is pressed against the patient's body.

The devices disclosed herein may be configured to be filled by a user at the time of use (e.g., in which the user fills the device drug reservoir at the time the device is to be used), assembled at the time of use (e.g., in which a user assembles a pre-filled drug reservoir at the time the device is to be used), or pre-filled and pre-assembled (e.g., in which the device is provided to the user already pre-filled and pre-assembled).

Figure 1:
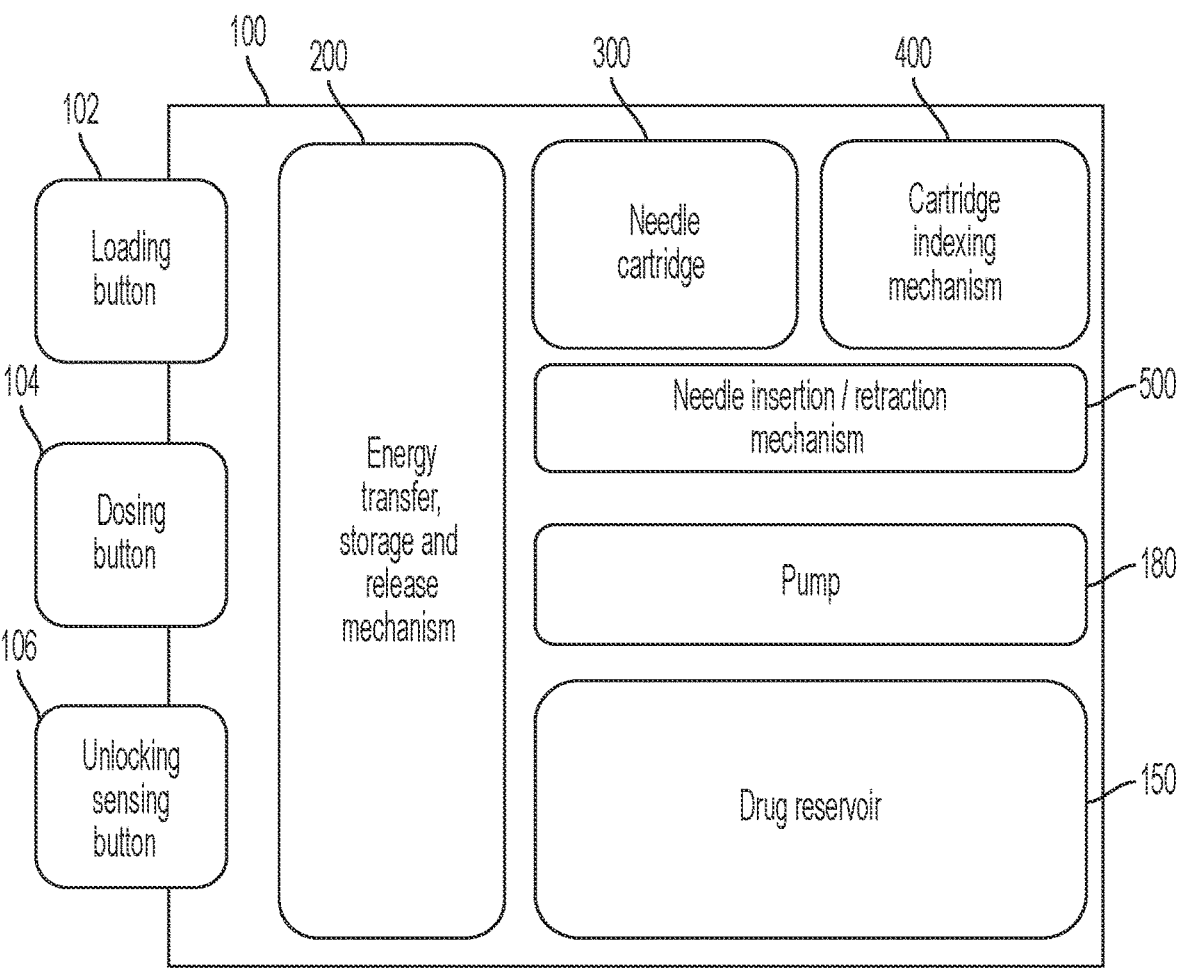
FIG. 1 is a block diagram providing a system-level overview of a multi-use drug-delivery device, according to some embodiments.

FIG. 1 is a block diagram providing a system-level overview of an exemplary multi-use drug-delivery device 100, according to some embodiments. Device 100 comprises a loading button 102, a dosing button 104, and an optional on-body sensing button 106.

Device 100 also comprises a drug reservoir 150. Reservoir 150 may be a rigid or elastomeric container configured to store a drug. Device 100 may further comprise a drug stored within reservoir 150. In another embodiment, a system may comprise one or more devices including device 100 and a drug. The term "drug" refers to one or more therapeutic agents including but not limited to insulins, insulin analogs such as insulin lispro or insulin glargine, insulin derivatives, GLP-1 receptor agonists such as dulaglutide or liraglutide, glucagon, glucagon analogs, glucagon derivatives, gastric inhibitory polypeptide (GIP), GIP analogs, GIP derivatives, oxyntomodulin analogs, oxyntomodulin derivatives, therapeutic antibodies and any therapeutic agent that is capable of delivery by device 100. The drug as used in the device may be formulated with one or more excipients. The device is operated in a manner generally as described herein by a patient, caregiver or healthcare professional to deliver drug to a person.

Device 100 also comprises a pump 180. Pump 180 may comprise any suitable pump that draws fluid drug from reservoir 150 and delivers said fluid drug through a fluid pathway and into the patient's body. One example of a suitable pump 180 is a rotary plunger pump. Other examples of suitable pumps include piston pumps, peristaltic pumps, diaphragm pumps, rotary vane pumps, and screw pumps.

Device 100 also comprises a needle cartridge 300 holding a plurality of needle assemblies. Each individual needle assembly within cartridge 300 may comprise an injection needle and a support hub that holds said needle and provides gripping and/or pushing surfaces that allow the needle assembly to be individually handled by an insertion/retraction mechanism. Each needle assembly may be configured to be used for a single injection. After a needle assembly has been used, the needle assembly may be retracted into the needle cartridge 300. After every needle assembly in the cartridge 300 has been used, the entire cartridge may be replaced and/or disposed of. In some disposable embodiments of device 100, the entire device 100 may be disposed of once every needle in cartridge 300 has been used.

Device 100 also comprises a needle insertion/retraction mechanism 500 that, when actuated by the user, drives an individual needle assembly within cartridge 300 that is operationally aligned with mechanism 500 from a retracted position into an injection position, and then retracts said individual needle assembly from the injection position back to the retracted position after the injection is complete. Mechanism 500 may comprise a single hammer or arm that both drives and retracts the individual needle assembly; alternately, mechanism 500 may comprise a plurality of hammers/arms, one/some of which drive the needle assembly, and one/some of which retract the needle assembly. Device 100 also comprises a cartridge indexing mechanism 400 that, when actuated, advances or indexes cartridge 300 to move a spent or used needle assembly out of operational alignment with mechanism 500 and positions a new, unused needle assembly into operational alignment with mechanism 500.

Device 100 may be used by a user to inject fluid drug stored within reservoir 150 into a patient's body. As used herein, a "user" may refer to a person operating device 100, e.g., by pressing its buttons and/or placing the device against the patient's body for an injection. A "patient" may refer to a person receiving the injection. In some embodiments, the "user" and the "patient" may be the same person, e.g., when the device is used by a patient to inject him or herself. In some embodiments, the "user" and the "patient" may be different persons, e.g., when the device is used by a caregiver to inject the patient.

Device 100 may be operated by a user by first pressing the loading button 102 to "load" the device. When a user presses the loading button 102, the work done by the user in pressing the button 102 is captured and/or harvested by an energy transfer, storage, and release mechanism 200. Mechanism 200 may comprise one or more mechanical components, such as gears, gear trains, slide racks, pinion couplers, wires, and/or other mechanical linkages, that transfer the work done by the user to other parts of device 100. For example, the work done by the user may be transferred to the cartridge indexing mechanism 400 that advances or indexes cartridge 300. Mechanism 200 may also comprise one or more springs (e.g., linear springs, torsion springs, clock springs, and the like) that store the work done by the user as potential energy that may be released at a later point in time to drive other parts of device 100.

After the loading button 102 has been pressed, the user may trigger the device to initiate an injection by pressing dosing button 104. In some embodiments, however, the dosing button 104 is initially locked such that the user cannot depress it. The dosing button 104 can be unlocked subsequently, such as, e.g., by a button or another unlocking component. In such embodiments, the user can unlock the dosing button 104 by actuating the unlocking button 106. For example, the user may press unlocking button 106 with his or her fingers. Alternately, the user may actuate unlocking button 106 by pressing the device 100 against the patient's body in preparation for an injection (e.g., the unlocking button 106 takes the form of an on-body sensing button 106). In such embodiments, when device 100 is pressed against the patient's body, the unlocking button 106 is depressed, thus unlocking dosing button 104. While the balance of this disclosure refers to an on-body sensing button 106, it should be understood that the that is only one embodiment of device 100. The principal function of button 106 is to unlock the dosing button 104, and button 106 need not take the form of an on-body sensing button.

When the user subsequently presses the dosing button 104, potential energy stored by the energy transfer, storage, and release mechanism 200 (e.g., by one or more springs) is released to drive the needle insertion/retraction mechanism 500 to insert an individual needle assembly for an injection. The energy stored by mechanism 200 is also released to drive pump 180 to pump liquid drug from reservoir 150 through the inserted needle assembly and into the patient. In other embodiments, in addition to, or separate from, the driving of the needle assembly, the driven needle assembly may be retracted back into the device after the injection is complete. For example, after the injection is complete, additional energy stored by mechanism 200 is released to drive the needle insertion/retraction mechanism 500 to retract the inserted needle assembly back into cartridge 300. In some embodiments, no means for converting or storing electrical energy (e.g., batteries, electrical motors) or chemical energy (e.g., fuel cells, combustion engines, fuel storage reservoirs, or reaction chambers for chemical reactions that produce heat or gas) are needed. Instead, all the energy required for driving device 100, including indexing cartridge 300, inserting and retracting a needle, and pumping the drug, are provided by the user.

Figure 2:
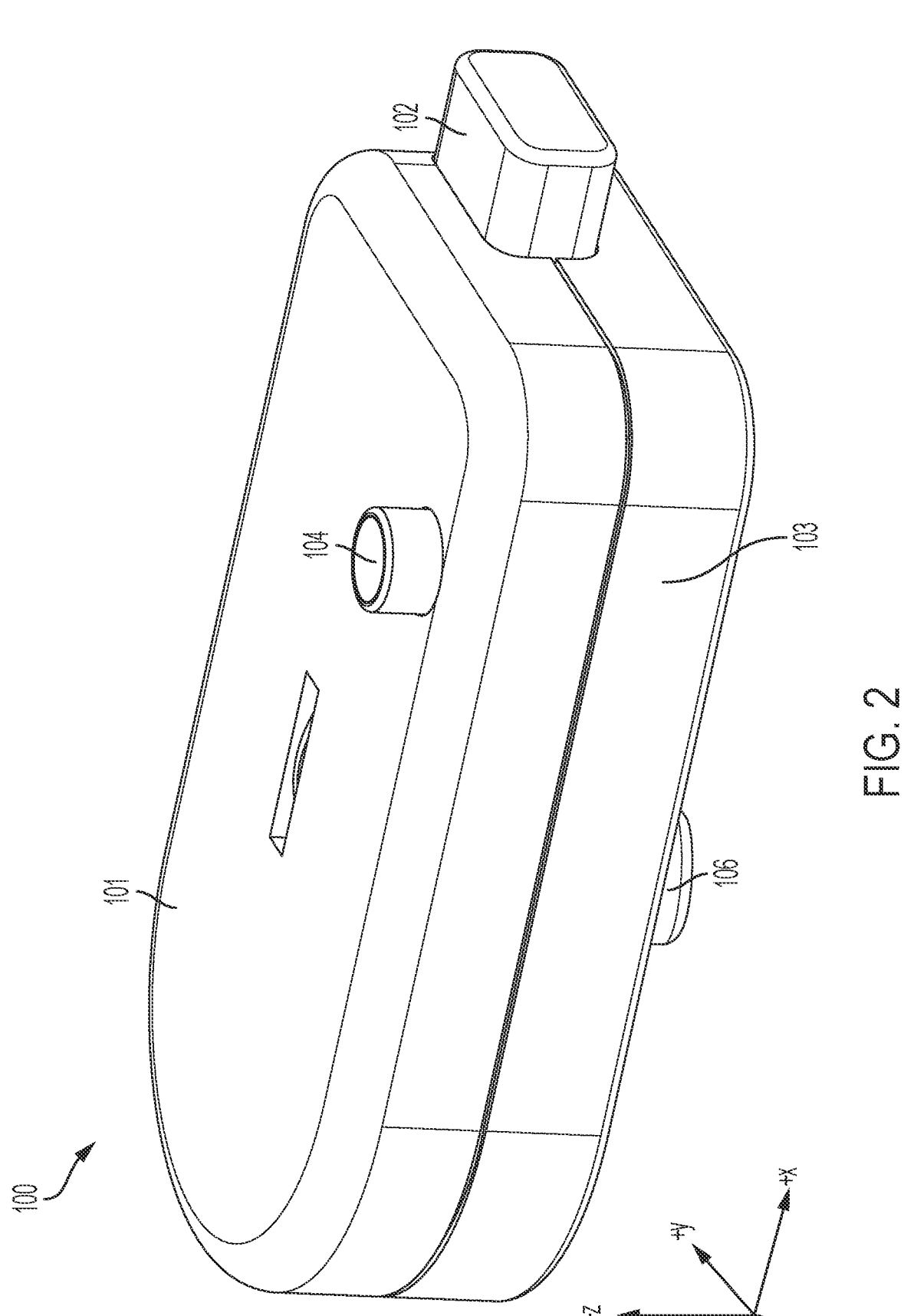
FIG. 2 provides a top perspective view of the external appearance of an exemplary drug-delivery device.
Figure 3:
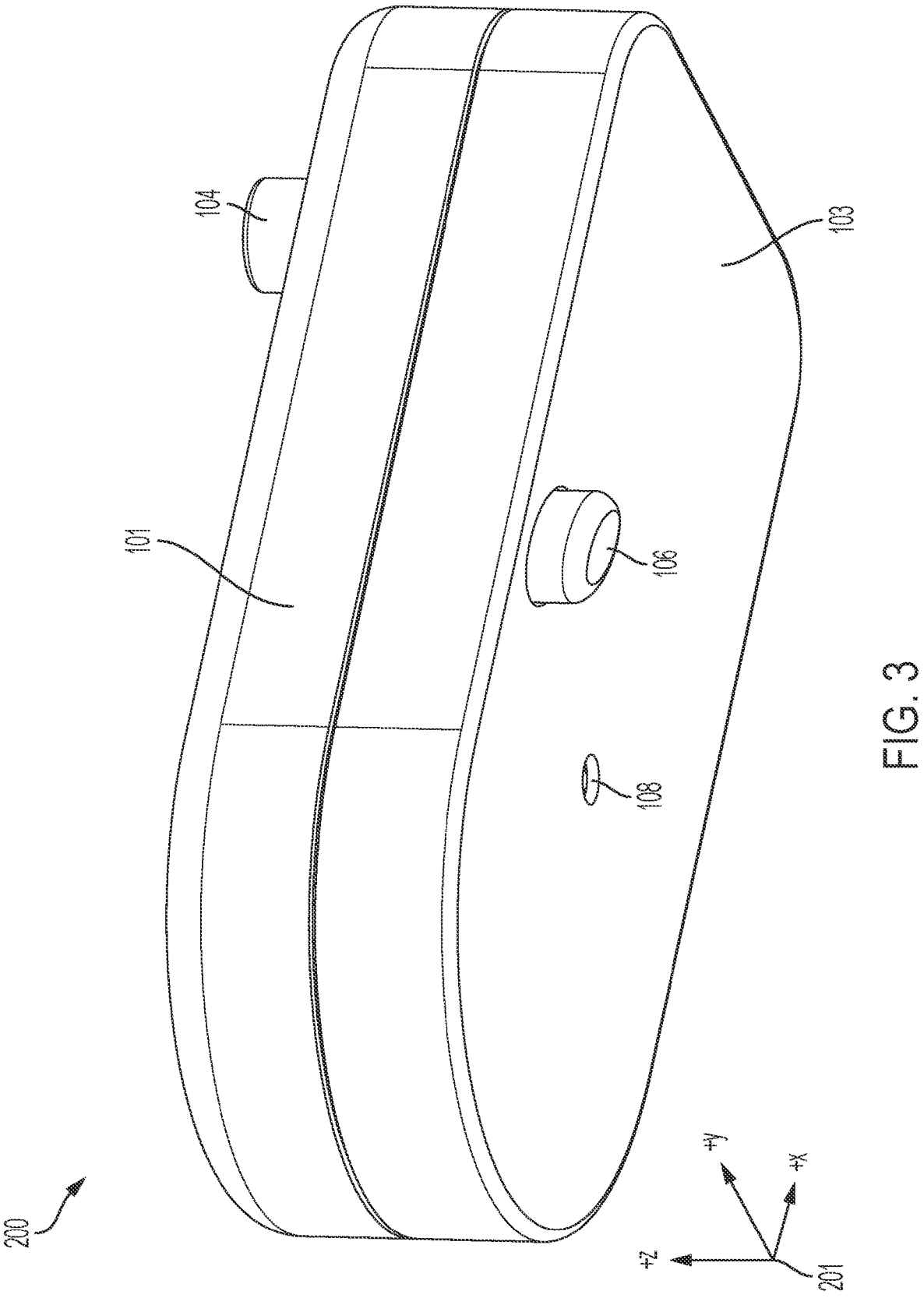
FIG. 3 provides a bottom perspective view of the external appearance of the exemplary drug-delivery device.

FIGS. 2 and 3 provide a top and a bottom perspective view (respectively) of the external appearance of an exemplary device 100. Solely for ease of explication, FIG. 2 to FIGS. 27A, 27B, and 27C will use the x, y, z directional system depicted by arrows 201. The symbol $\odot$ shall represent an arrow coming out of the page, while the symbol $\otimes$ shall represent an arrow going into the page. In the specification and claims, references to the "up," "upward," "upper," or "top" direction shall mean the positive z direction; references to the "down," "downward," "lower," or "bottom" direction shall mean the negative z direction; references to the "proximal" direction shall mean the negative x direction; references to the "distal" direction shall mean the positive x direction; references to the "left" direction shall mean the positive y direction; references to the "right" direction shall mean the negative y direction; references to the "horizontal" plane shall mean the x-y plane; and references to the "vertical" plane shall mean the x-z or y-z plane, as appropriate.

Device 100 comprises an upper housing 101 and a lower housing 103 that house the internal components of the device. Loading button 102 protrudes from a distal end of the device, dosing button 104 protrudes upward from upper housing 101, while on-body sensor button 106 (e.g., unlocking button 106) protrudes downward from lower housing 103. Lower housing 103 also defines a needle aperture 108 (see FIG. 3) through which a needle of a needle assembly may protrude when it is inserted into the patient.

Figure 4:
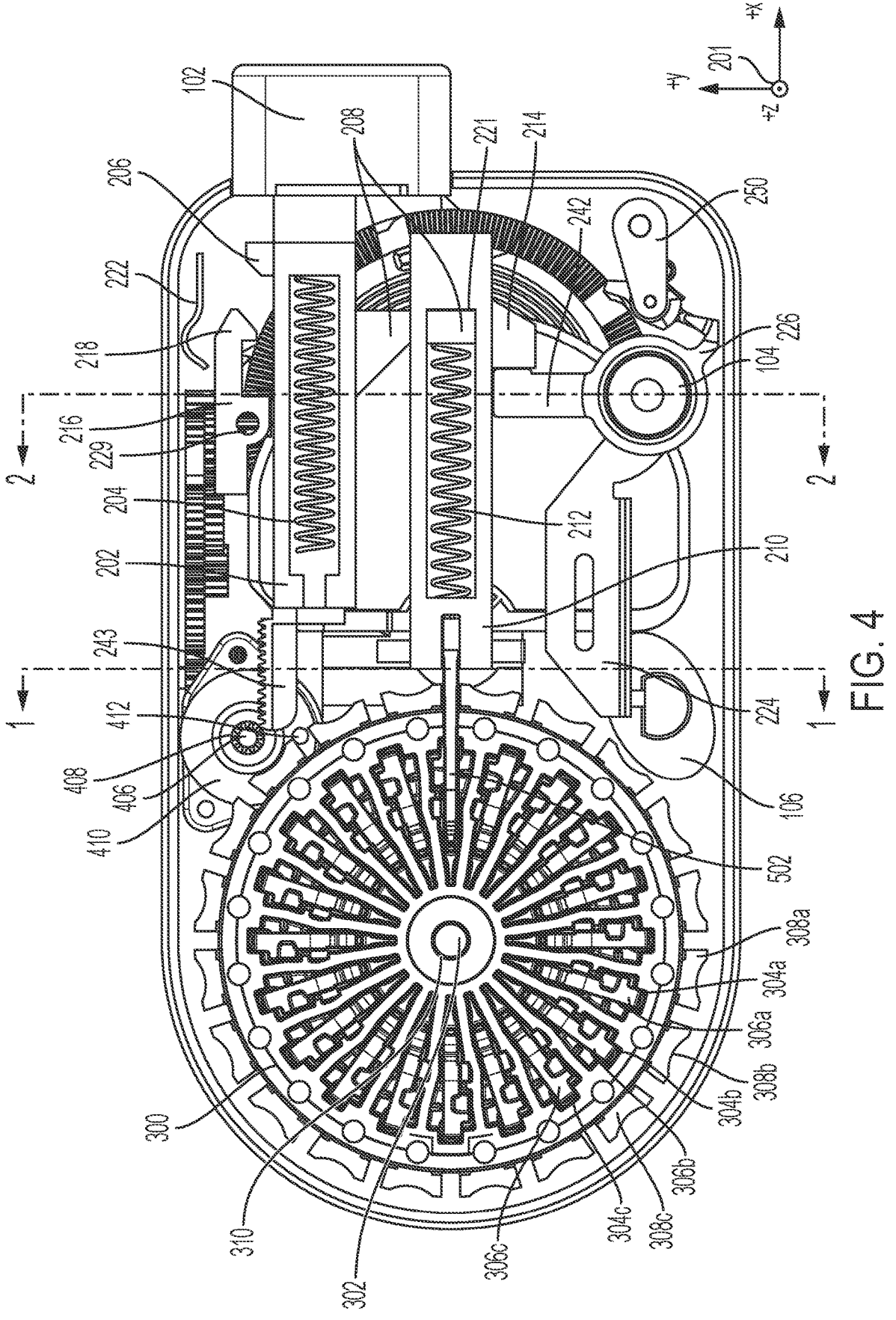
FIG. 4 provides a top-down view of internal components of the exemplary drug-delivery device.
Figure 5:
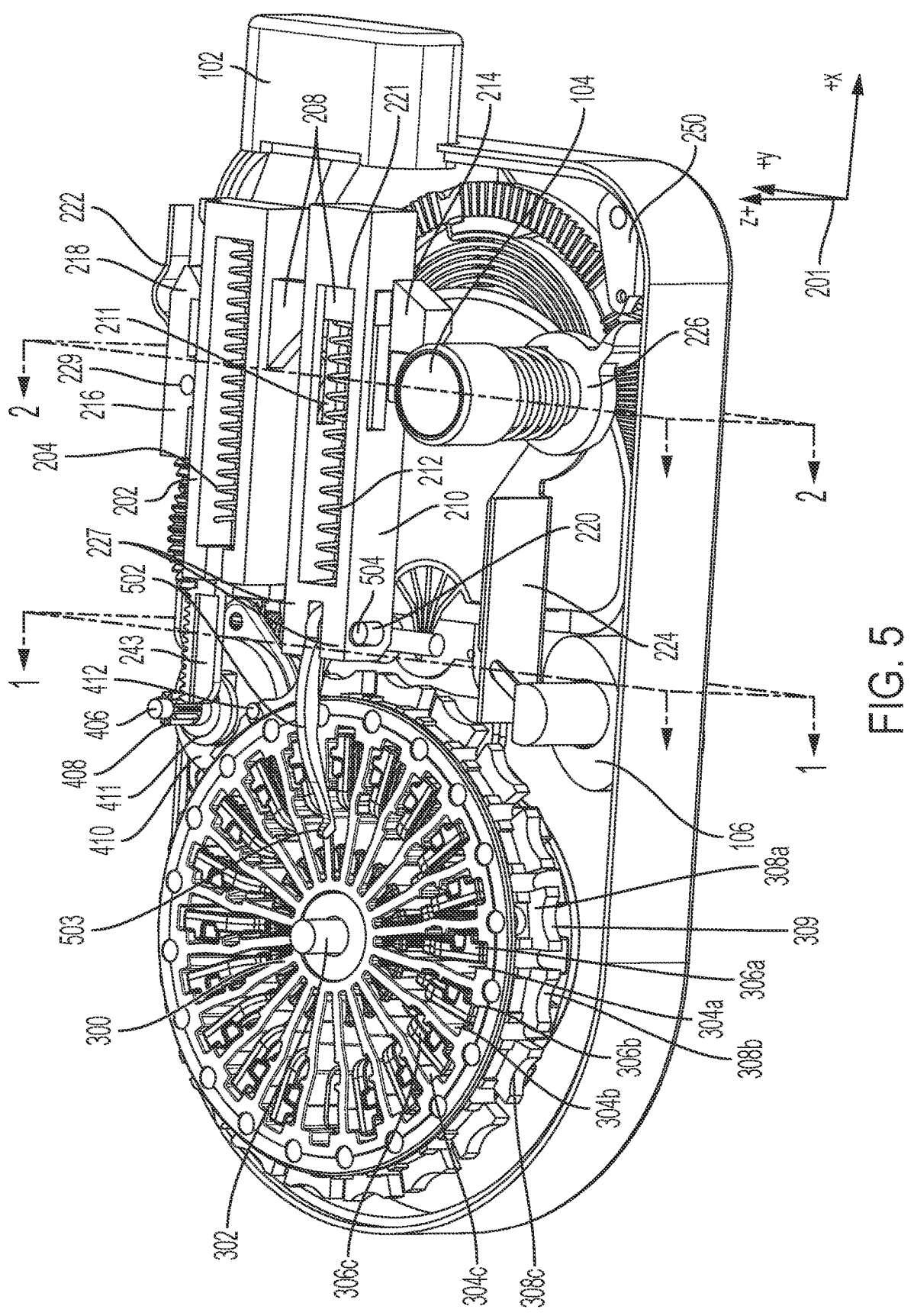
FIG. 5 provides a top perspective view of internal components of the exemplary drug-delivery device.
Figure 6:
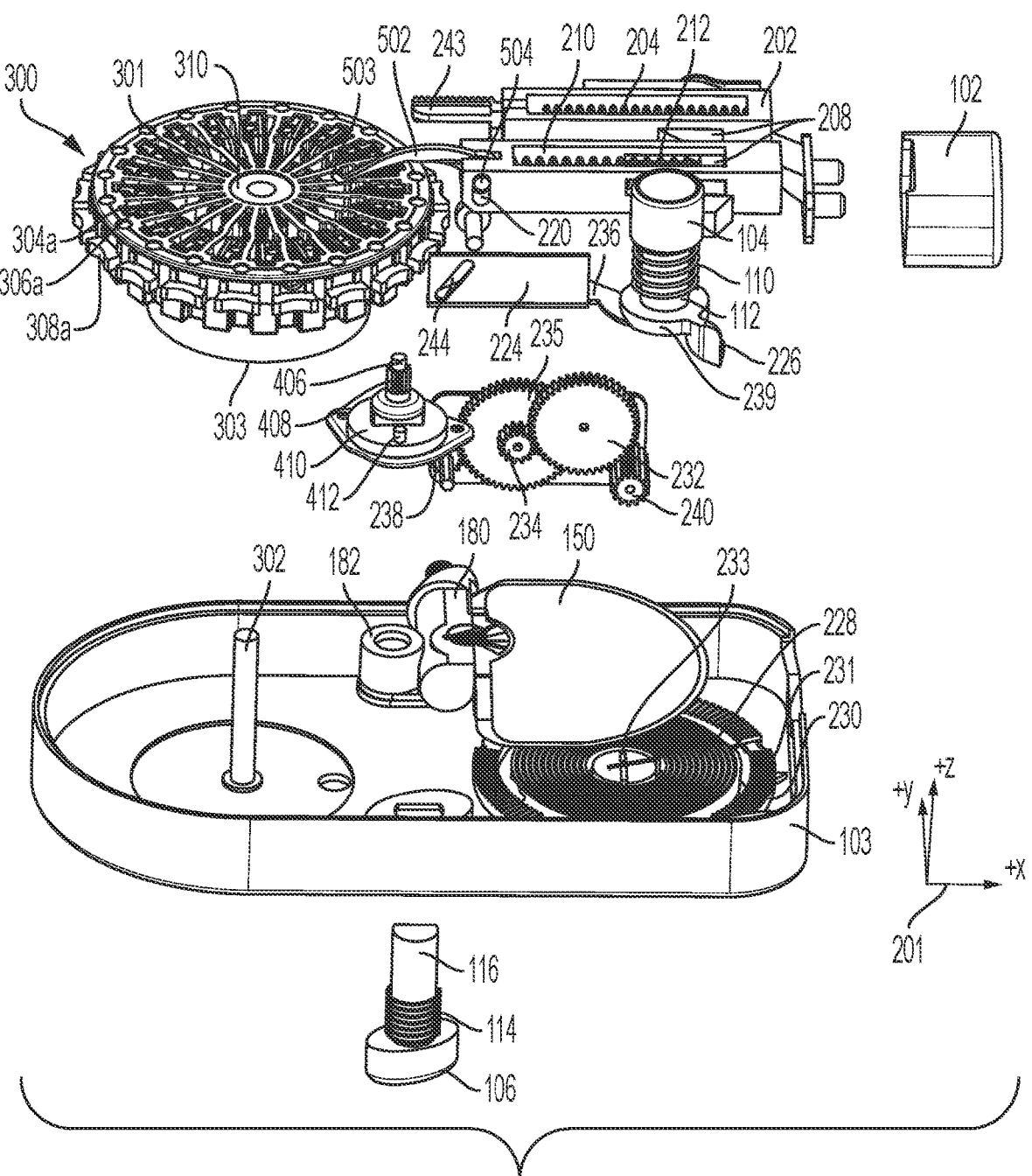
FIG. 6 provides an exploded, perspective view of the exemplary drug-delivery device.

FIGS. 4, 5, and 6 display the internal components of device 100 when upper housing 101 has been removed. FIG. 4 provides a top-down view of device 100; FIG. 5 provides a perspective view of device 100; and FIG. 6 provides an exploded, perspective view of device 100.

In the embodiment depicted in FIGS. 4-6, cartridge 300 may take the form of a round carousel having a generally planar top surface 301 and a generally planar bottom surface 303 (see FIG. 6). Cartridge 300 has a central shaft 310 extending through a central, vertical axis of the cartridge from the top surface to the bottom surface. The central shaft 310 may be configured to accommodate a central spindle 302 that extends vertically upward from the inner surface of lower housing 103 (see FIG. 6). When central spindle 302 is inserted through central shaft 310, carousel 300 is configured to rotate about central spindle 302. Carousel 300 defines a plurality of cavities 304a, b, c, etc. (collectively or individually referred to herein as a "cavity" or "cavities" 304, as appropriate). Each cavity 304 extends radially outward from the central shaft 310 towards the radial perimeter of the cartridge and includes an opening in the top surface 301 and an opening in the bottom surface 303.

Figure 22A:
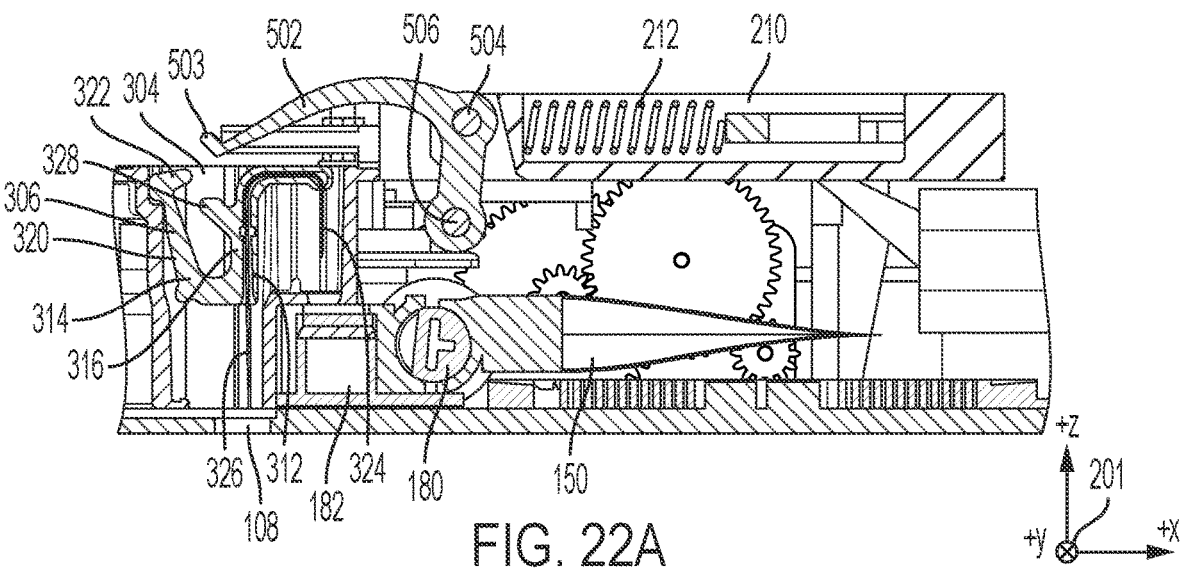
FIG. 22A and FIG. 22B show how proximal translation of the primary slide component drives insertion of a needle in the exemplary drug-delivery device.
Figure 22B:
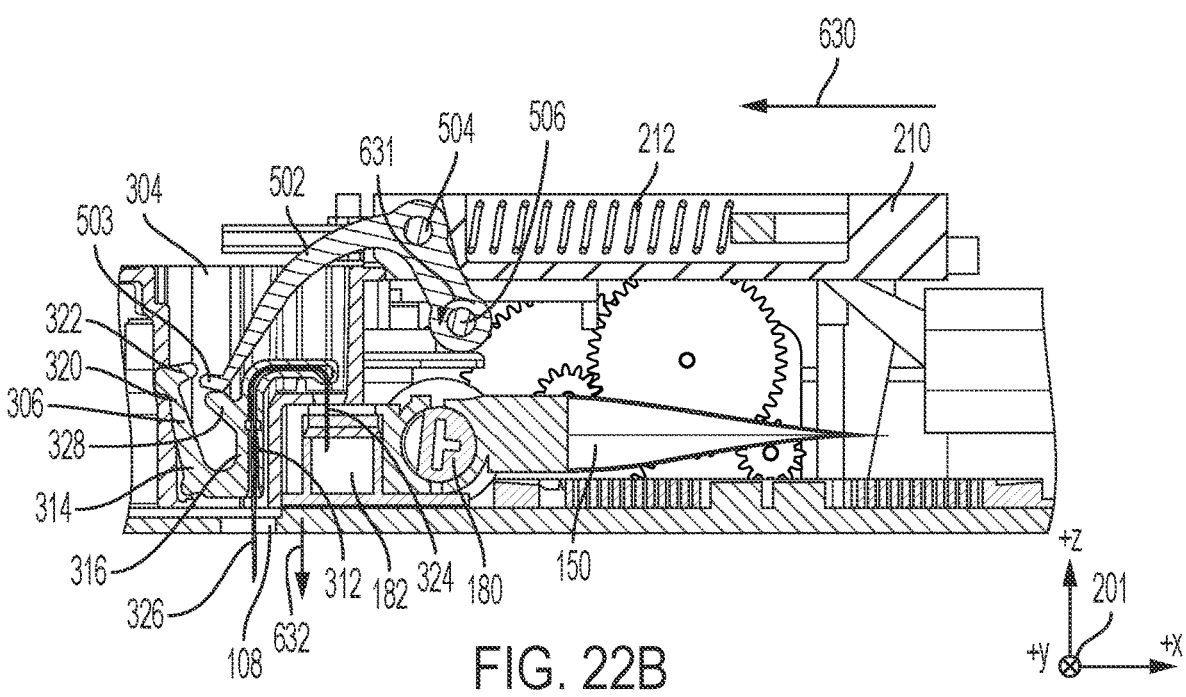

Each cavity 304 houses a needle assembly 306a, b, c (collectively or individually referred to herein as a "needle assembly" or "needle assemblies" 306, as appropriate). One exemplary embodiment of a needle assembly 306 is depicted in FIGS. 22A and 22B. In this embodiment, needle assembly 306 comprises a J-shaped needle or cannula 312 having a first leg segment 324 which is configured to penetrate drug septum 182 and draw fluid drug therefrom, as described below, and a second leg segment 326 which is configured to be driven into a patient's body to inject the drug. Needle 312 is held within a support hub 314 having a needle supporting base 316. In addition to holding and supporting needle 312, needle supporting base 316 also mounts a ledge 328. Needle supporting base 316 also mounts an upstanding arm part 320 topped with a tang 322. Additional details regarding cartridge 300, cavities 304, and/or needle assemblies 306 are further described in U.S. Pat. No. 9,149,578, filed Nov. 17, 2011, and entitled NEEDLE CARTRIDGE FOR MEDICA-TION INJECTION DEVICE, the entire contents of which are hereby expressly incorporated by reference.

Returning to FIGS. 4-6, cartridge 300 includes an inter-mittently rotating drive. For example, cartridge 300 comprises a plurality of Geneva wheel members 308a, b, c (collectively or individually referred to herein as a "Geneva wheel member" or "Geneva wheel members" 308, as appropriate) which interact with a Geneva wheel 410 to index or advance cartridge 300 one increment at a time, as described in further detail below. Each Geneva wheel member comprises a substantially planar member that extends radially outward in the horizontal plane from cartridge 300. Each respective Geneva wheel member may comprise a vertical, concave, arcuate wall 309 (see FIG. 5) at the furthest extent of such respective wheel member away from central shaft 310. When a Geneva wheel member is aligned with Geneva wheel 410, this vertical, concave wall 309 fits against inner hub 411 of Geneva wheel 410 (see FIG. 5). Geneva wheel 410 further comprises a Geneva pin 412 that extends vertically upward from a horizontal plane of Geneva wheel 410. Every pair of adjacent Geneva wheel members (e.g., 308a and 308b) define a gap in-between said wheel members into which Geneva pin 412 may fit.

Reservoir 150 (best seen in FIG. 6), which in this embodiment takes the form of an elastomeric container, is configured to contain a drug. Reservoir 150 may be provided to users pre-filled with drug or may be configured to be filled by users. Pump 180 (also best seen in FIG. 6) in this embodiment takes the form of a rotary plunger pump. Examples of suitable rotary plunger pumps are disclosed in U.S. Prov. App. No. 62/891,600, entitled "ROTARY PLUNGER PUMP SUBSYSTEMS" and filed on Aug. 26, 2019, the entire contents of which are hereby incorporated by reference. As discussed in further detail below, pump 180 can be driven to pump liquid drug from reservoir 150 towards drug septum 182, where it can be pushed into an individual needle and from there into a patient.

Energy transfer, storage, and release mechanism 200, shown in FIGS. 5-6, includes a secondary slide 202, a primary slide 210, a latch 216, a dosing button lock 224, a blocker 226, a face gear 230, a gear train comprising gears 232, 234, 235, 238, and 240, and a latch assembly 250. Each of these components shall now be discussed in turn.

Figure 11:
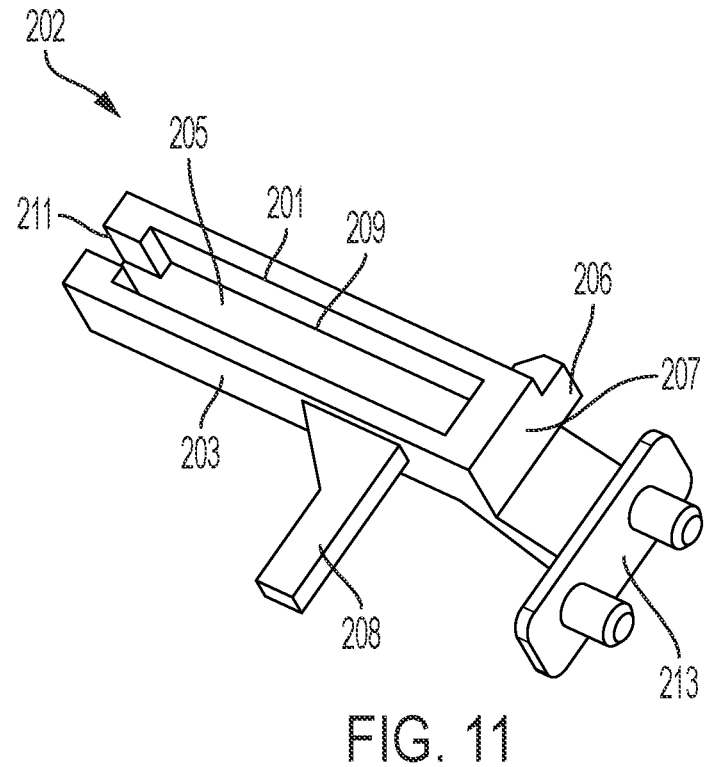
FIG. 11 provides a detailed close-up view of a secondary slide component, according to some embodiments.

Secondary slide 202 is attached or mechanically joined via one or more intermediate mechanical components (e.g., gears, rods, wires, or the like) to loading button 102. Slide 202 is configured to slidably move parallel to the x-axis of device 100 between a secondary slide distal position and a secondary slide proximal position, as described in further detail below. FIG. 11 provides a more detailed view of one embodiment of secondary slide 202. In this embodiment, secondary slide 202 takes the form of a hollow and substantially rectangular-shaped member having its long axis aligned with the x-axis of device 100. Slide 202 comprises a first left wall 201, a second right wall 203, a bottom wall 205, a distal wall 207, an open top channel 209 defined between body portions of the left and right walls 201, 203, and an open proximal channel 211 defined at the proximal end of the slide between ends of the left and right walls 201, 203. Slide 202 also comprises a loading button support 213 extending from distal wall 207, which is configured to be attached or mechanically joined via one or more intermediate components to loading button 102. Secondary slide 202 also comprises a locking tab 206 extending horizontally outward from the left wall 201 of slide 202 and a compression tab 208 extending horizontally outward from the right wall 203 of slide 202. Secondary slide 202 houses a spring 204 (see FIGS. 4-6) within the channel 209. A distal end of spring 204 abuts an interior surface of distal wall 207, and a proximal end of spring 204 abuts a tab (not shown) extending downwards from an interior surface of upper housing 101.

Figure 8:
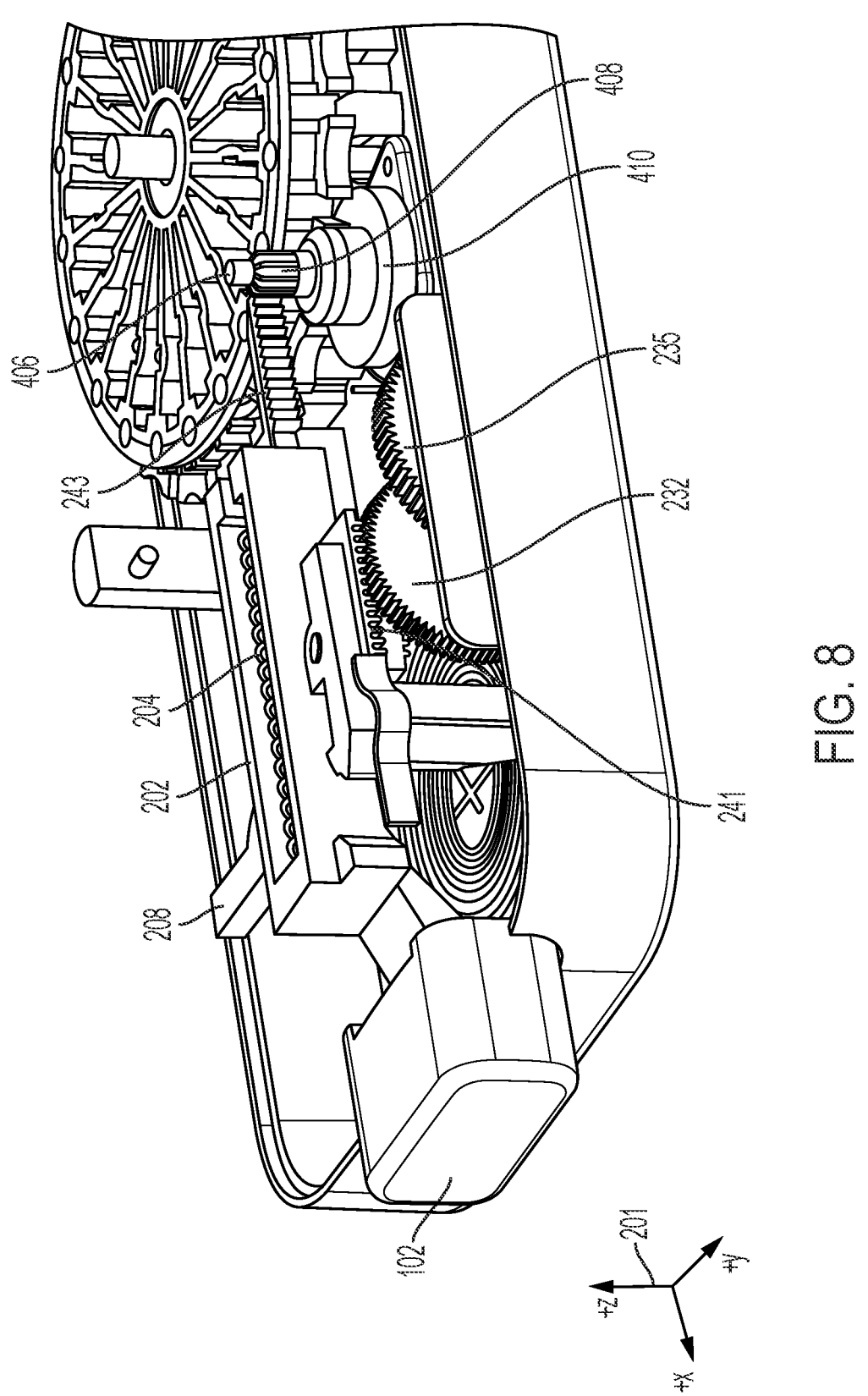
FIG. 8 provides a first top perspective view of internal components of the exemplary drug-delivery device, in which certain components have been omitted for simplicity and clarity.

FIG. 8 depicts a perspective view of device 100 from a different angle. For simplicity and clarity, certain components have been removed from the view of device 100 in FIG. 8. As depicted in FIG. 8, secondary slide 202 also includes one or more slide racks (two shown): a downward-facing slide rack 241 and a side-facing slide rack 243. Downward-facing slide rack 241 projects horizontally outward from the left wall 201 of secondary slide 202 (i.e., on the +y side of slide 202) and has teeth that face downwards (i.e., in the −z direction) which interact with gear 232 (described in more detail below). Side-facing slide rack 243 projects proximally from the proximal end of secondary slide 202 (shown coupled to the proximal end portion of the left wall 201) and has teeth that face in the +y direction. The teeth from the side-facing slide rack interact with teeth 408 of pinion coupler 406, as described in more detail below.

Figure 12:
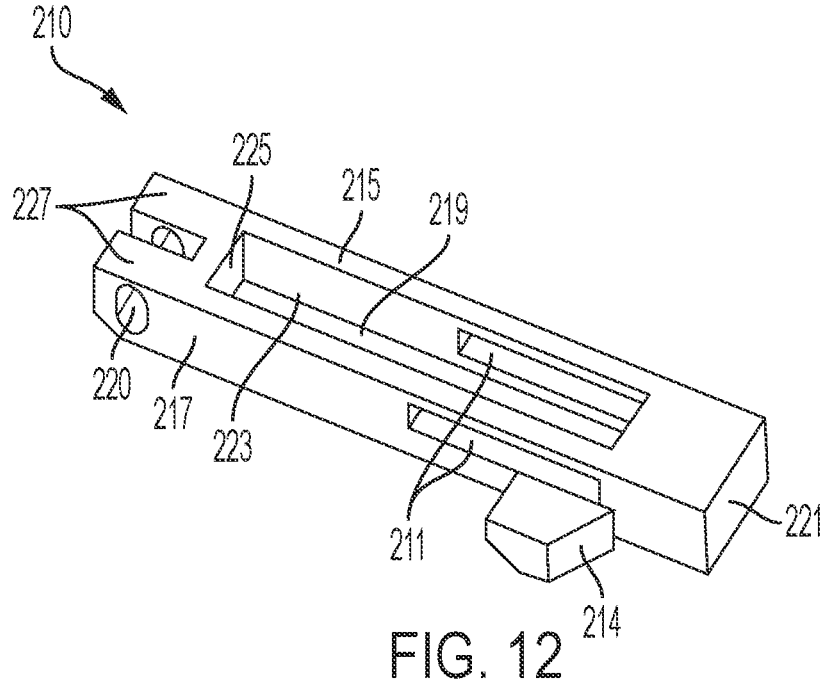
FIG. 12 provides a detailed close-up view of a primary slide component, according to some embodiments.
Figure 13A:
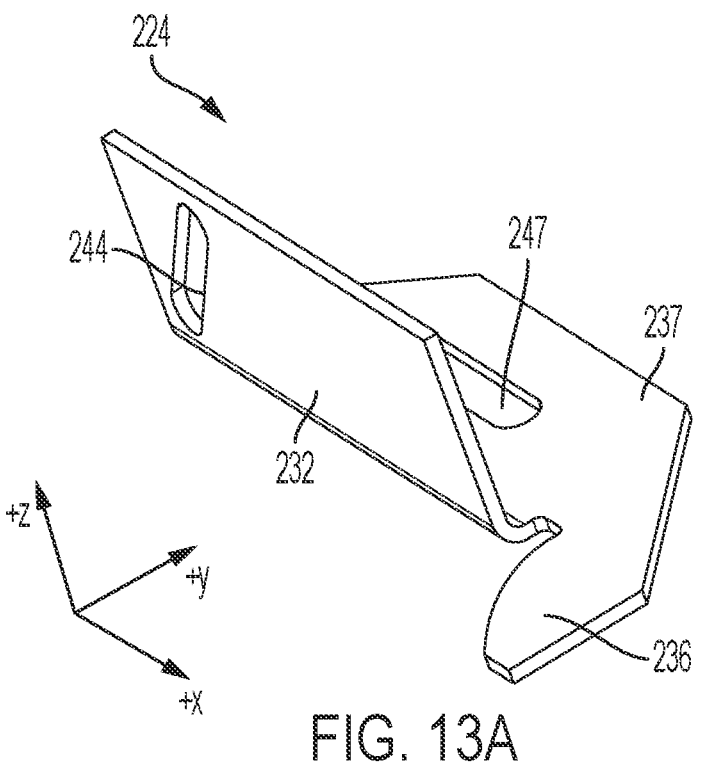
FIG. 13A and FIG. 13B provide detailed close-up views of a dosing button lock component, according to some embodiments.
Figure 13B:
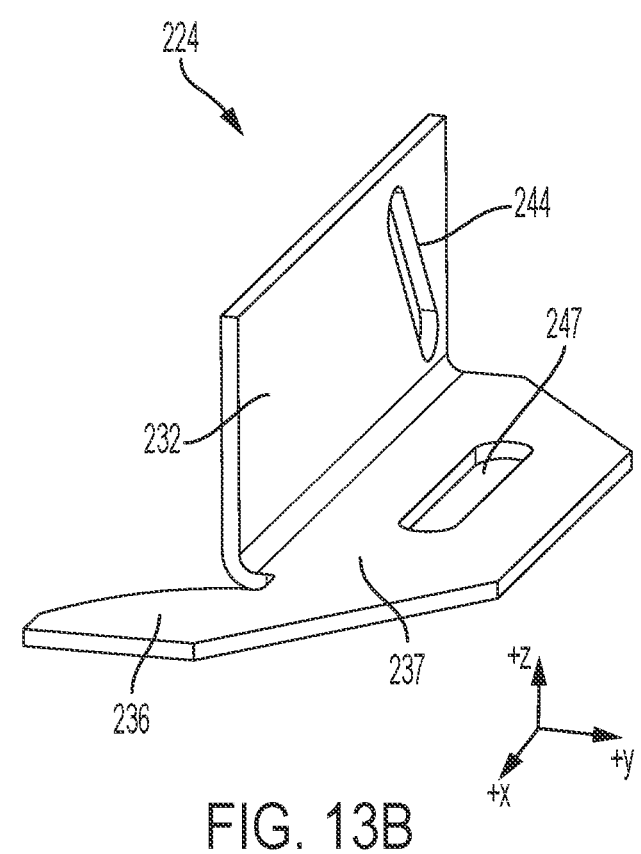

Returning to FIGS. 4-6, primary slide 210 is configured to slidably move parallel to the x-axis of device 100 between a primary slide distal position and a primary slide proximal position, as described in further detail below. FIG. 12 provides a more detailed view of one embodiment of primary slide 210. In this embodiment, primary slide 210 takes the form of a hollow and substantially rectangular-shaped member that also has its long axis aligned with the x-axis of device 100. Primary slide 210 comprises a first left wall 215, a second right wall 217, a bottom wall 219, a distal wall 221, a proximal wall 225, and an open top channel 223 defined between the body portions of the left and rights walls 215, 217. Primary slide 210 also comprises a locking tab 214 extending horizontally outward from the right wall 217 of slide 210 (i.e., the −y side), and a pair of fins 227 that extend proximally from proximal wall 225. Left wall 215 and right wall 217 define slots 211 extending laterally (y-direction) therethrough, and fins 227 define channels 220 extending laterally (y-direction) therethrough. When device 100 is fully assembled (see FIGS. 4-6), compression tab 208 of secondary slide 202 is configured to extend through slots 211 and through the interior volume of primary slide 210. Primary slide 210 also houses a spring 212 within its channel 223. A distal end of spring 212 abuts a proximal surface of compression tab 208 of secondary slide 202, and a proximal end of spring 212 abuts an interior surface of proximal wall 225 of primary slide 210.

Latch 216 is configured to rotate in the horizontal plane around axis 229 and comprises a latch tab 218. When latch 216 is rotated in a counter-clockwise direction (when viewed from the top down), an anti-over-rotation mechanism (shown as a spring 222) prevents latch 216 from over-rotating and also biases latch 216 in a clockwise direction back to its neutral position (i.e., as shown in FIGS. 4-5), where a long axis of latch 216 is parallel to the x-axis of device 100. The anti-over-rotation mechanism may also include a pin or plate with a spring configured to function as described above.

Dosing button lock 224 interacts with other components to prevent the depressing of dosing button 104 by the user until the on-body sensing button 106 is depressed. Dosing button lock 224 is depicted in greater detail in FIGS. 13A and 13B. In this embodiment, lock 224 comprises a vertical panel 232 that defines a pin slot 244. Slot 244 may extend diagonally in a +x/+z direction. Lock 224 also comprises a horizontal panel 237 extending from the vertical panel 232, such as, for example, in an orthogonal manner. Horizontal panel 237 defines another pin slot 247, which extends in a +x direction. Horizontal panel 237 also comprises a blocker member 236, which takes the form of a substantially flat tab aligned with the horizontal plane, extending from a distal end of horizontal panel 237 beyond the vertical panel 232. Member 236 is also shown extending laterally beyond the vertical panel 232 in the −y direction.

Figure 7A:
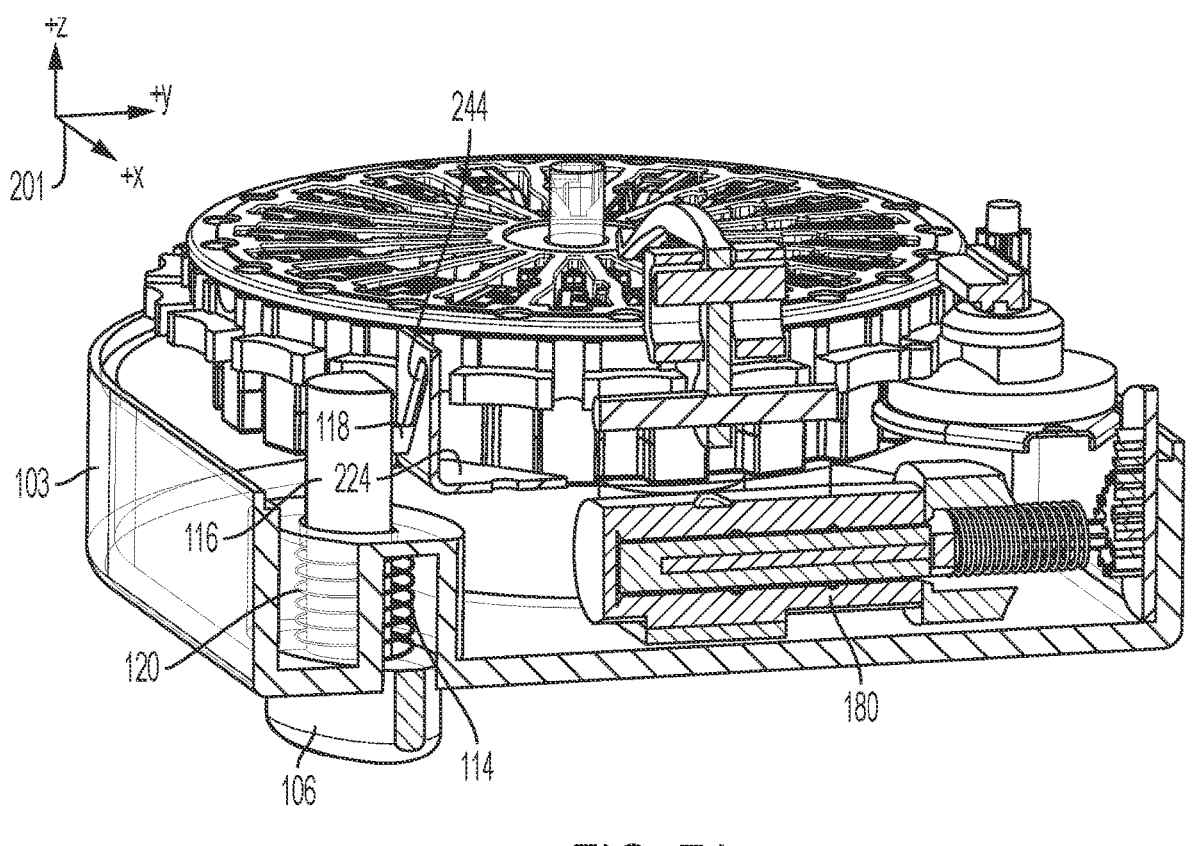
FIG. 7A provides a first cross-sectional perspective view of the exemplary drug-delivery device.

FIG. 7A provides a cross-sectional, perspective view of device 100 when cut along plane 1-1 (see FIGS. 4-5), and best depicts how dosing button lock 224 interacts with on-body sensing button 106 when device 100 is fully assembled. For clarity, lower housing 103 has been rendered transparent. On-body sensing button 106 can translate up and down into or out of a sensing button cavity 120, which is defined within lower housing 103. Button 106 also comprises a vertical sensing button shaft 116 and around which is coaxially surrounded by a sensing button spring 114. A top end of spring 114 abuts an interior surface of cavity 120, while a bottom end of spring 114 abuts an interior, top surface of button 106. Spring 114 biases button 106 downward out of cavity 120. When the user presses the bottom side of device 100 against his/her body, the user's pressing force overcomes the biasing force of spring 114 and causes button 106 to translate upward into cavity 120. When the pressing force is removed, the spring force allows the button 106 to return to its biased-out position. A pin 118 is configured to extend in a horizontal direction from the left side of shaft 116. When device 100 is assembled, pin 118 is configured to ride within pin slot 244 of dosing button lock 224. As discussed in further detail below, the interaction of pin 118 with pin slot 244 of dosing button lock 224 causes dosing button lock 224 to translate proximally (i.e., in the −x direction) when button 106 is pushed upward into cavity 120.

Figure 14A:
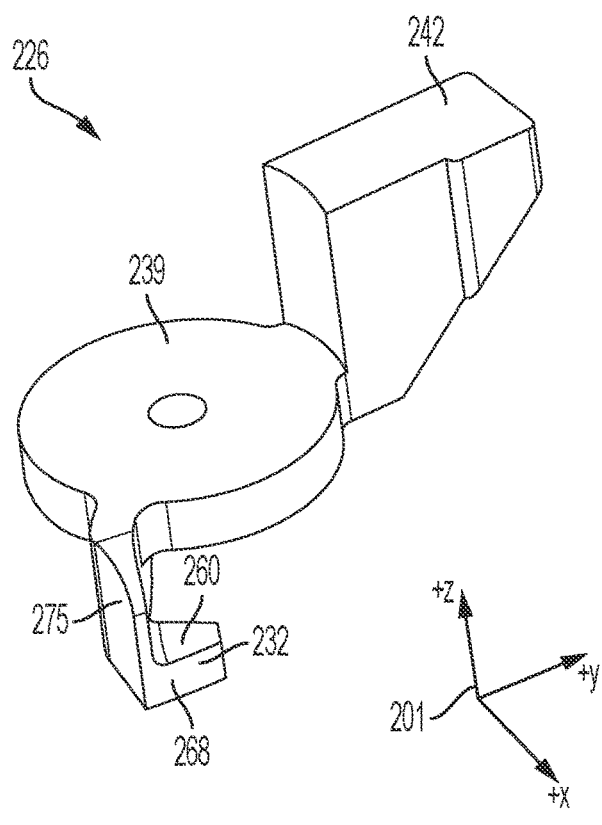
FIG. 14A and FIG. 14B provide detailed close-up views of a blocker component, according to some embodiments.
Figure 14B:
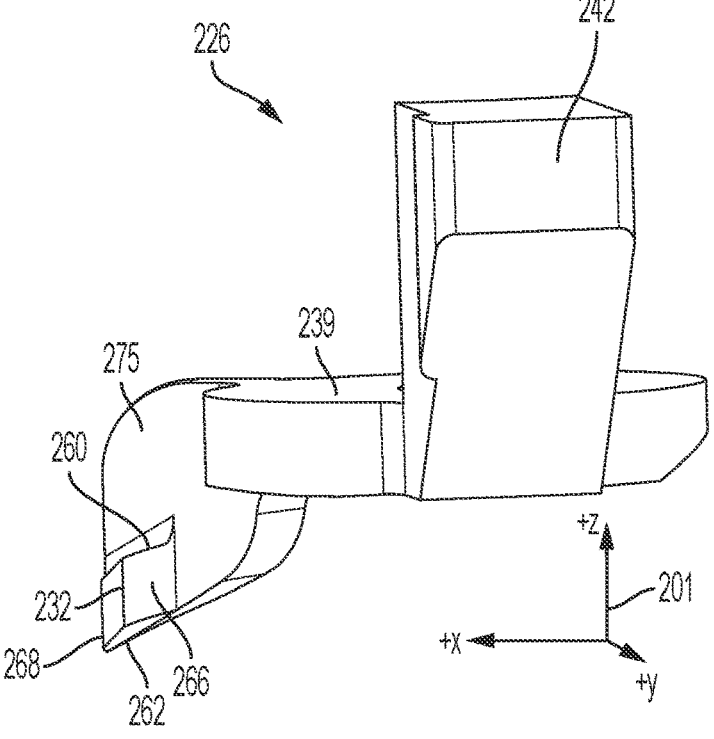

Returning to FIGS. 4-6, blocker 226 interacts with dosing button lock 224 to prevent the user from depressing dosing button 104 until it has been unlocked, i.e., until the on-body sensing button 106 is depressed. When the dosing button 104 is unlocked and depressed, blocker 226 also interacts with latch assembly 250 (described in further detail below) to release energy stored by mechanism 200. Blocker 226 is depicted in greater detail in FIGS. 14A and 14B. In this embodiment, blocker 226 comprises three parts: a blocking tab 242, a button seat 239, and an arm 275. Button seat 239 takes the form of a substantially planar surface or member (in this embodiment, having the shape of a circle, but other shapes are also possible) oriented parallel to the horizontal plane of device 100. Blocking tab 242 is attached to the left side (i.e., the +y side) of button seat 239 and takes the form of a substantially planar surface or member oriented parallel to the vertical plane of device 100 that extends in both of the +y/+z directions away from the seat 239. Arm 275 is also attached to button seat 239, circumferentially spaced away from the tab 242, extending approximately in the +x direction. Arm 275 comprises a fin 232 disposed on a distal end thereof, extending in the +y direction. Fin 232 comprises a top surface 260, a bottom surface 262, a proximal surface 266, and a distal surface 268. As best seen in FIG. 14B, top surface 260 and bottom surface 262 are angled diagonally; that is, they are parallel to a plane oriented in a −x/+z direction.

Figure 7B:
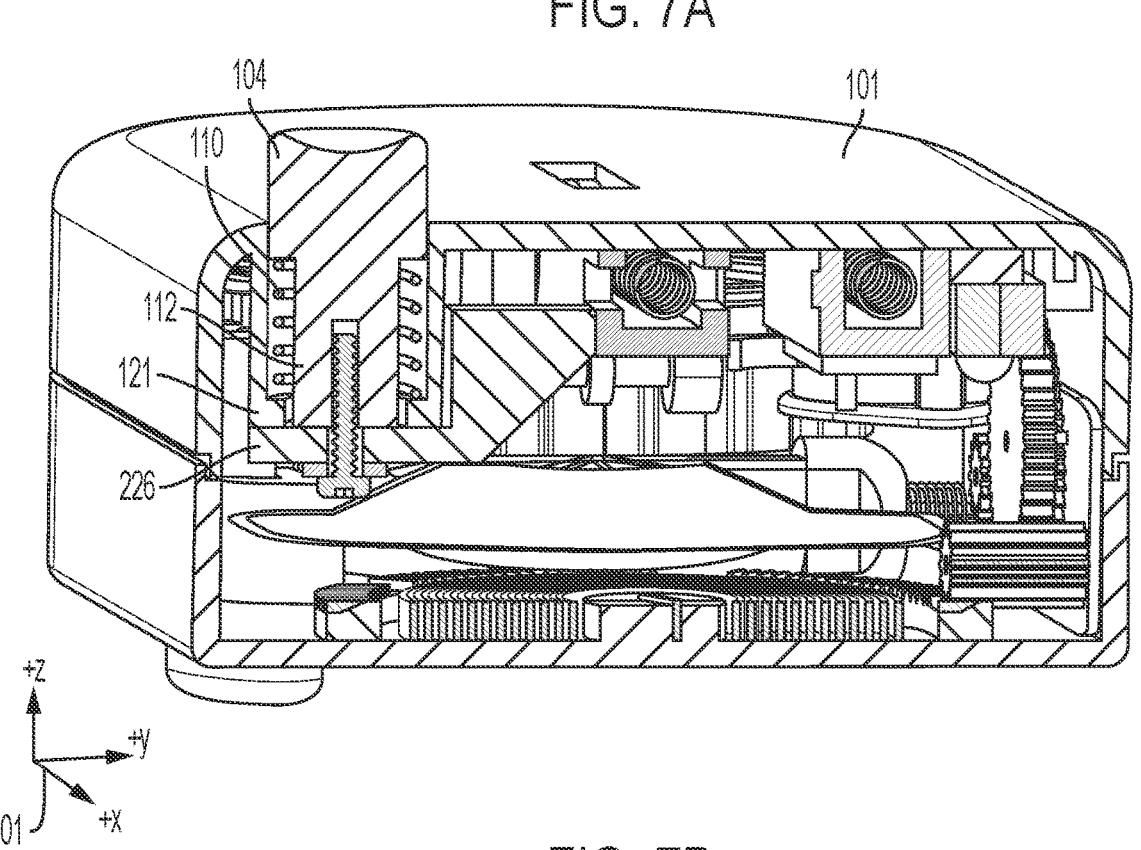
FIG. 7B provides a second cross-sectional perspective view of the exemplary drug-delivery device.

FIG. 7B provides a perspective, cross-sectional view of device 100 when cut along plane 2-2 (see FIGS. 4-5). Both FIG. 7B and FIG. 6 best depict how blocker 226 interacts with dosing button 104 and with dosing button lock 224 when device 100 is fully assembled. As depicted in FIG. 6, when the user has not yet depressed the on-body sensing button 106, blocker member 236 of dosing button lock 224 is disposed beneath button seat 239 of blocker 226. The position of blocker member 236 beneath button seat 239 of blocker 226 prevents blocker 226 from translating downwards. As discussed in further detail below, when the user presses the on-body sensing button 106 upwards, the interaction between pin 118 and pin slot 244 of dosing button lock 224 causes dosing button lock 224 to translate in a proximal direction (i.e., in the −x direction) such that blocker member 236 clears button seat 239, thus unlocking blocker 226 and allowing blocker 226 to translate downwards.

Dosing button 104 can translate up and down into or out of a dosing button cavity 121, which is defined within upper housing 101 (see FIG. 7B). Dosing button 104 comprises a vertical dosing button shaft 112 which is coupled with blocker 226 such that button 104 and blocker 226 translate up and down together. In the embodiment depicted in FIG. 7B, dosing button shaft 112 is coupled with blocker 226 using a screw, though any suitable method of fixed attachment may be used (e.g., heat staking, one-way snaps, etc.). A dosing button spring 110 coaxially surrounds dosing button shaft 112. A top end of spring 110 abuts a bottom surface of button 104, while a bottom end of spring 110 abuts an interior, upward-facing surface of dosing button cavity 121. Spring 110 biases button 104 (and blocker 226, which is attached to button 104) upwards. When a user presses down on button 104, shaft 112 transmits the user's downward pressing force of button 104 to button seat 239 of blocker 226. When blocker 226 is unlocked as described previously, the user's downward pressing force causes button 104 and blocker 226 (including button seat 239) to translate downward.

Mechanism 200 also comprises face gear 230 and a gear train comprising gears 232, 234, 235, 238, and 240, each of which are best seen in FIG. 6. Face gear 230 takes the form of a circular-shaped gear that includes a plurality of upward-facing teeth 231. Face gear 230 is coupled to a clock spring 228. Both face gear 230 and clock spring 228 are disposed parallel to the horizontal plane and are configured to rotate about a central axis 233. Clock spring 228 resists rotational movement of face gear 230 around central axis 233. Put another way, rotating face gear 230 around central axis 233 in a first rotational direction adds tension to clock spring 228, thus storing potential energy within clock spring 228. Face gear 230 interacts with and drives gear 240, which in turn interacts with and drives gear 232. Gear 232 also interacts and drives small gear 234 which is rotationally coupled with gear 235 such that gears 234 and 235 rotate together. Gear 235 in turn interacts with gear 238, which provides rotational torque to pump 180. The number of gears, relative sizes of gears and teeth, and configuration may be selected to provide the rotational speed and torque needed to drive the pump.

Figure 9:
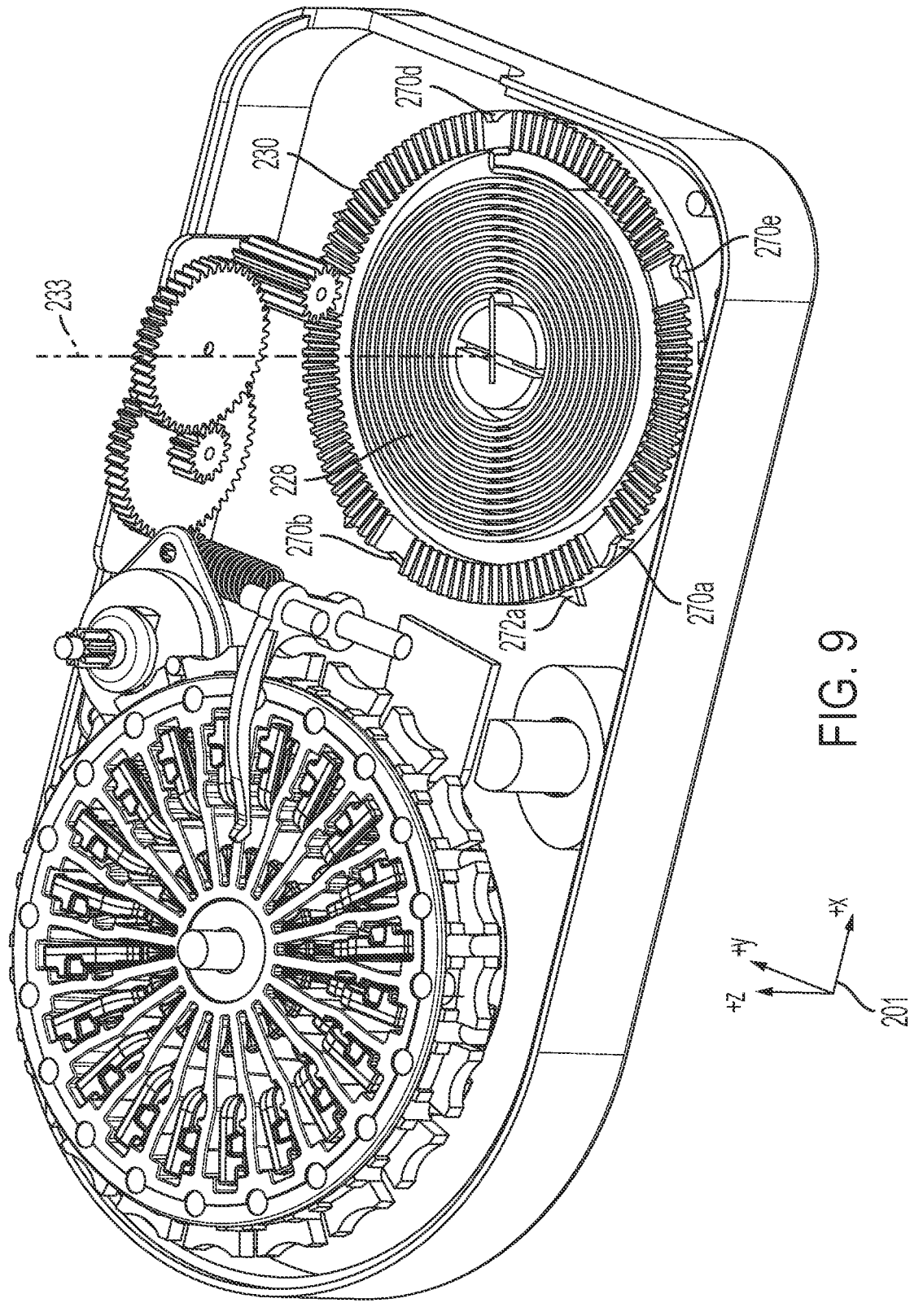
FIG. 9 provides a second top perspective view of internal components of the exemplary drug-delivery device, in which certain components have been omitted for simplicity and clarity.
Figure 10:
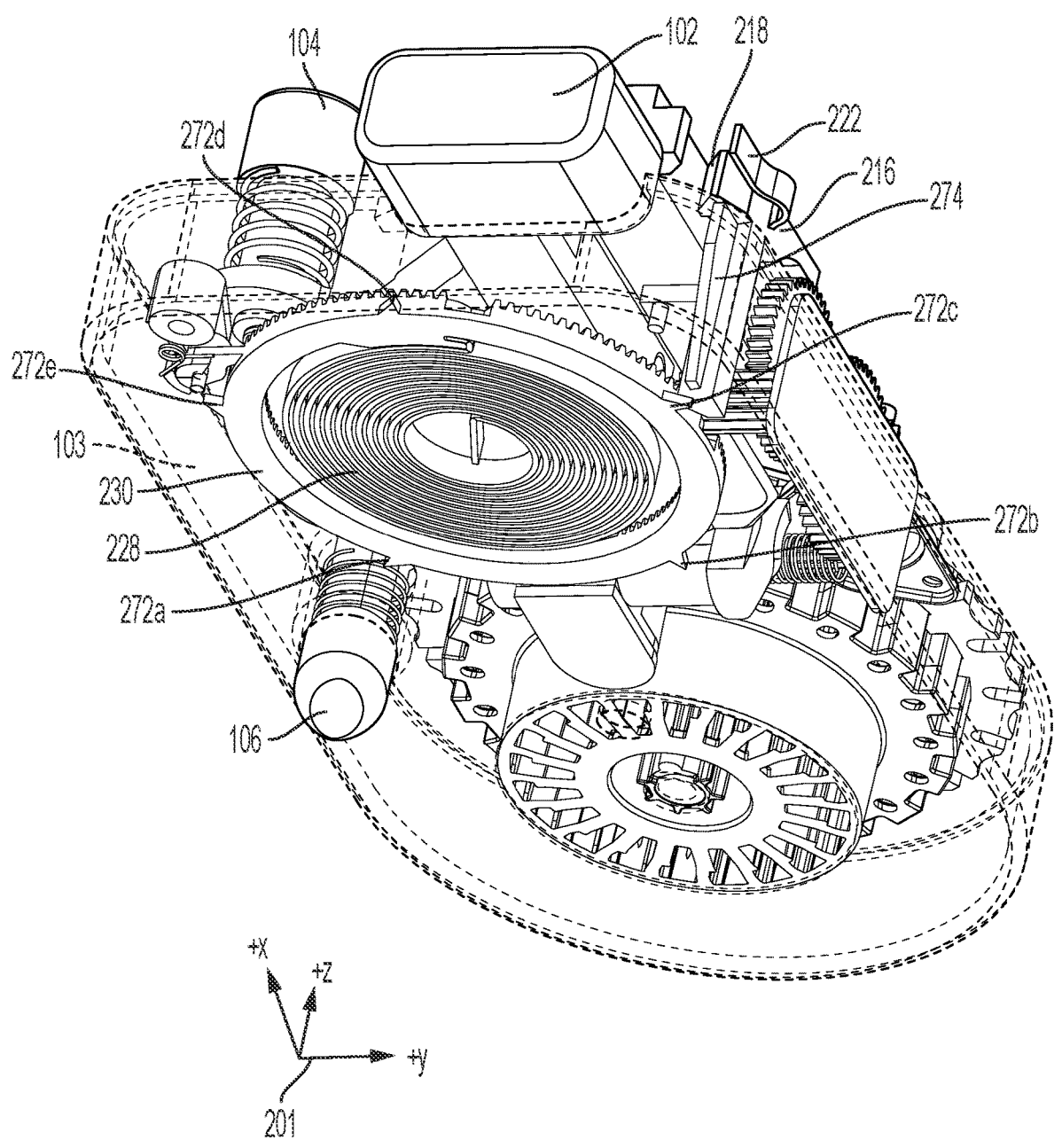
FIG. 10 provides a bottom perspective view of internal components of the exemplary drug-delivery device.

FIGS. 9 and 10 provide additional, more detailed views of face gear 230 and clock spring 228, and how they interact with latch 216. FIG. 9 provides a top perspective view in which certain components (e.g., slides 202, 210, blocker 226, dosing button lock 224, and latch assembly 250) have been removed to expose face gear 230 and clock spring 228, and FIG. 10 provides a bottom perspective view in which bottom housing 103 has been rendered transparent to better view the underside of face gear 230. As can be seen in FIG. 9, the top surface of face gear 230 defines a plurality of notches 270*a, b, c, d, e* (collectively or individually referred to herein as "notch" or "notches" 270, as appropriate). While the embodiment of face gear 230 depicted in FIG. 9 defines five notches (notch 270*c* is obscured beneath gear 240 in FIG. 9), other embodiments are also possible in which face gear 230 defines fewer or more notches. Notches are shown spaced radially from one another and may be spaced equi-radially. Each notch is shaped to accommodate a pawl 256, as described in further detail below in reference to FIG. 23A. As best seen in FIG. 10, face gear 230 also comprises a plurality of fins 272*a, b, c, d, e* (collectively or individually referred to herein as "fins" or "fin" 272, as appropriate). Once again, while the embodiment of face gear 230 depicted in FIGS. 9 and 10 comprises five fins, other embodiments are also possible in which face gear 230 comprises fewer or more fins. Fins are shown spaced radially from one another and may be spaced equi-radially. Each fin extends radially outward in the horizontal plane from the outer circumference of face gear 230 and comprises a sloped leading edge and a trailing straight edge. As shown, the fins may be radially offset from the notches. Also as best seen in FIG. 10, latch 216 further comprises a downward-extending arm 274 that extends down from the horizontal plane of latch tab 218 to the horizontal plane of face gear 230. Each fin 272 is sized and placed such that they will push against and displace arm 274 radially outward when face gear 230 rotates to a position in which such fin 272 is aligned with arm 274, as discussed in further detail below.

Figures 23A, 23B, 23C:
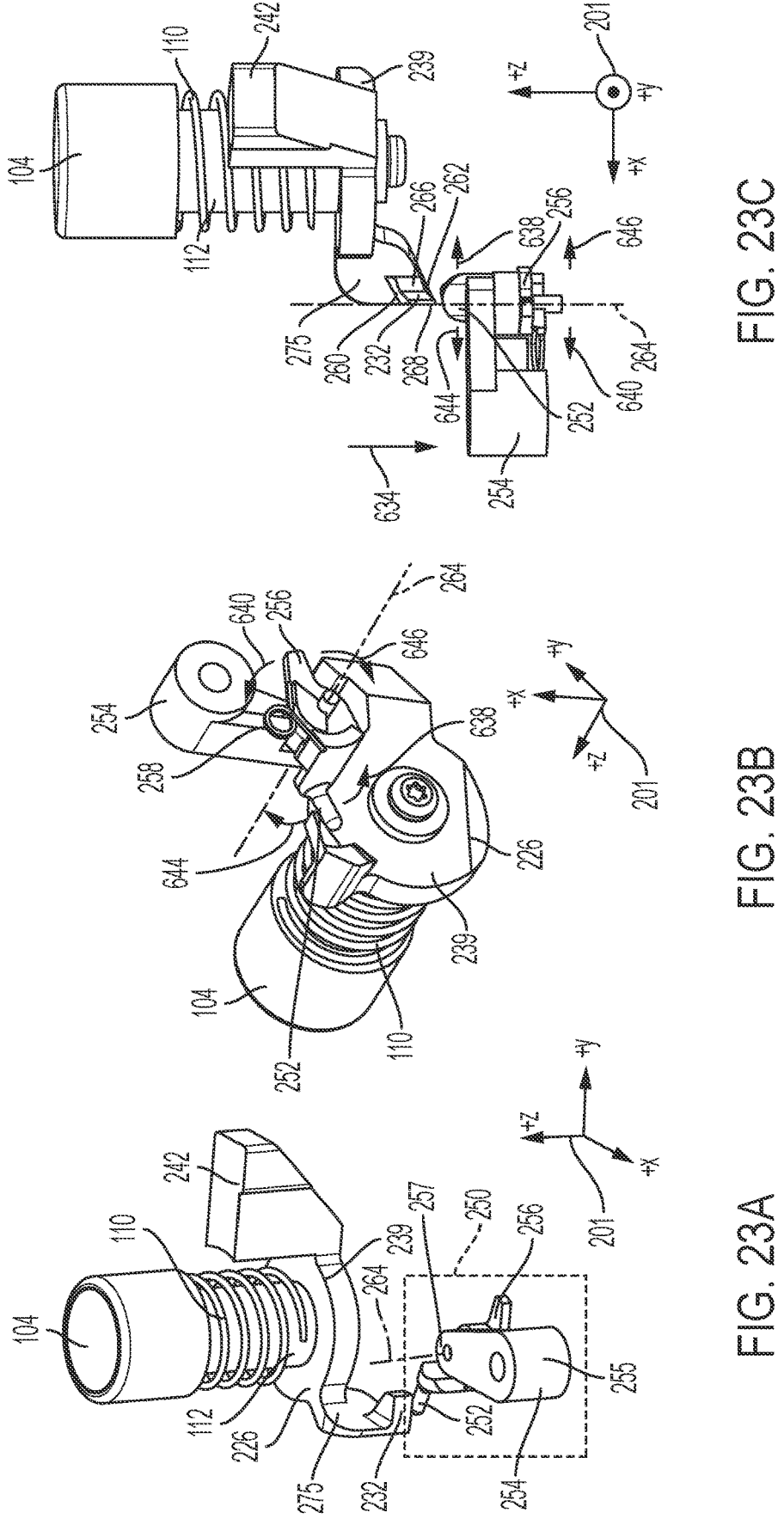
FIG. 23A, FIG. 23B, and FIG. 23C show the interaction between the dosing button component, a blocker component, and a latch assembly component in the exemplary drug-delivery device.

Latch assembly 250 is visible in the distal-right corner of device 100 in FIGS. 4-5 and depicted in greater detail in FIGS. 23A-C. Latch assembly comprises a latch support 254 that secures latch assembly 250 to bottom housing 103. Latch support 254 has a first end 255 and a second end 257. First end 255 of support 254 is attached to an interior surface of bottom housing 103, while second end 257 of support 254 supports a latch pin 252 and a pawl 256. Both latch pin 252 and pawl 256 may rotate in the horizontal plane about axis 264. A torsion v-spring 258 is disposed between latch pin 252 and pawl 256 and coupled to both components such that rotation of latch pin 252 around axis 264 also imparts rotational forces on pawl 256, and vice versa. When device 100 is fully assembled, latch pin 252 is configured to interact with fin 232 of blocker 226 and pawl 256 is configured to interact with face gear 230, as described in further detail below.

Cartridge indexing mechanism 400 is depicted in FIGS. 4-5. Mechanism 400 includes a pinion coupler 406 having teeth 408 that interact and are driven to rotate with teeth of side-facing slide rack 243 when rack 243 is linearly translated. Pinion coupler 406 is rotationally coupled with Geneva wheel 410 such that rotation of pinion coupler 406 drives rotation of Geneva wheel 410. Geneva wheel 410 may be shaped as a substantially planar disc having a first circumference, and an inner hub 411 having a second circumference smaller than the first circumference stacked on top of said planar disc. A Geneva pin 412 extends vertically upwards from a top surface of the planar disc. Geneva pin 412 interacts with Geneva wheel members 308 of cartridge 300 by fitting in the gaps between adjacent wheel members, as best seen in FIG. 4.

Needle insertion/retraction mechanism 500 is depicted in FIGS. 4-6 and in FIGS. 22A and 22B. Mechanism 500 comprises a drive member or hammer 502. A proximal end of hammer 502 includes a head 503 which interacts with needle assemblies 306 within cartridge 300 that are operationally aligned to engage with hammer 502, as discussed in further detail below. A distal end of hammer 502 includes pins 504 and 506 (see FIGS. 22A and 22B). When device 100 is fully assembled, hammer 502 is configured to rotate about pin 506, which is secured to either upper housing 101 or lower housing 103 (not shown in FIGS. 22A and 22B). When device 100 is assembled, pin 504 of hammer 502 is also configured to slot into channel 220 defined within fins 227 of primary slide 210 (see FIG. 5). Proximal or distal translation of primary slide 210 therefore exerts a force on pin 504 of hammer 502, thus causing hammer 502 to rotate about pin 506.

Figure 15A:
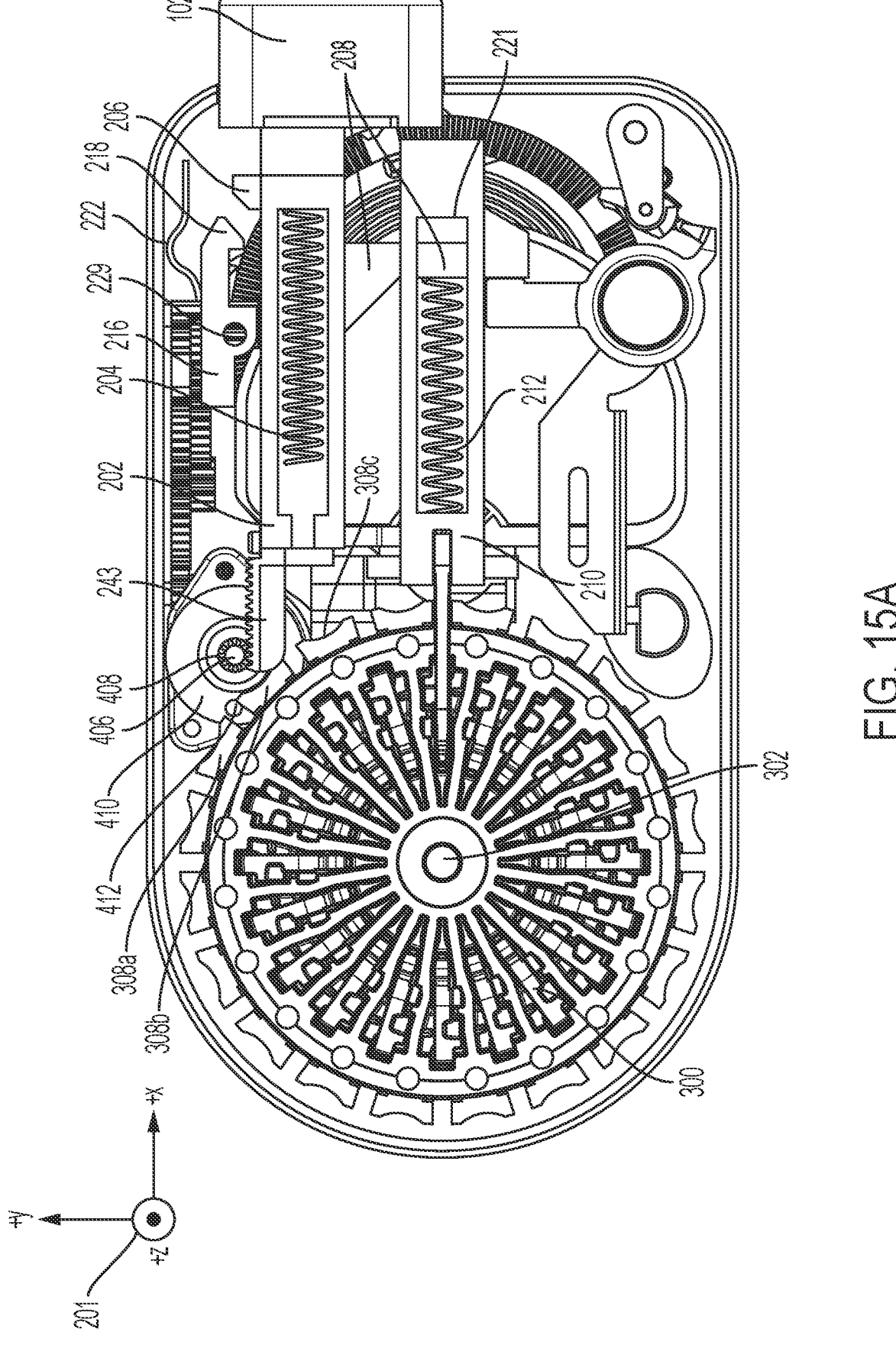
FIG. 15A, FIG. 15B, FIG. 15C, and FIG. 15D depict a series of states of the exemplary drug-delivery device in operation when the user presses a loading button.

The operation of device 100 will now be described. FIGS. 15A-D depict a series of states of device 100 in operation, according to some embodiments. FIG. 15A depicts device 100 in an initial neutral state, before the user begins depressing loading button 102. While in this neutral state, spring 204 of secondary slide 202 biases slide 202 in the distal direction to hit a stop (e.g., a surface of secondary slide 202 hits a stop in the upper housing 101 or lower housing 103, or when a distal surface of compression tab 208 hits distal wall 221 of primary slide 210). The position of secondary slide 202 in this initial neutral state of device 100 is referred to herein as the secondary slide distal position. Similarly, while in this neutral state, spring 212 of primary slide 210 biases slide 210 in the distal direction until it hits a stop in the upper housing 101 or lower housing 103 (not shown). The position of primary slide 210 in this initial neutral state of device 100 is referred to herein as the primary slide distal position. Geneva pin 412 is initially engaged between two Geneva wheel members 308 of cartridge 300, labeled 308a and 308b in FIG. 15A.

Figure 15B:
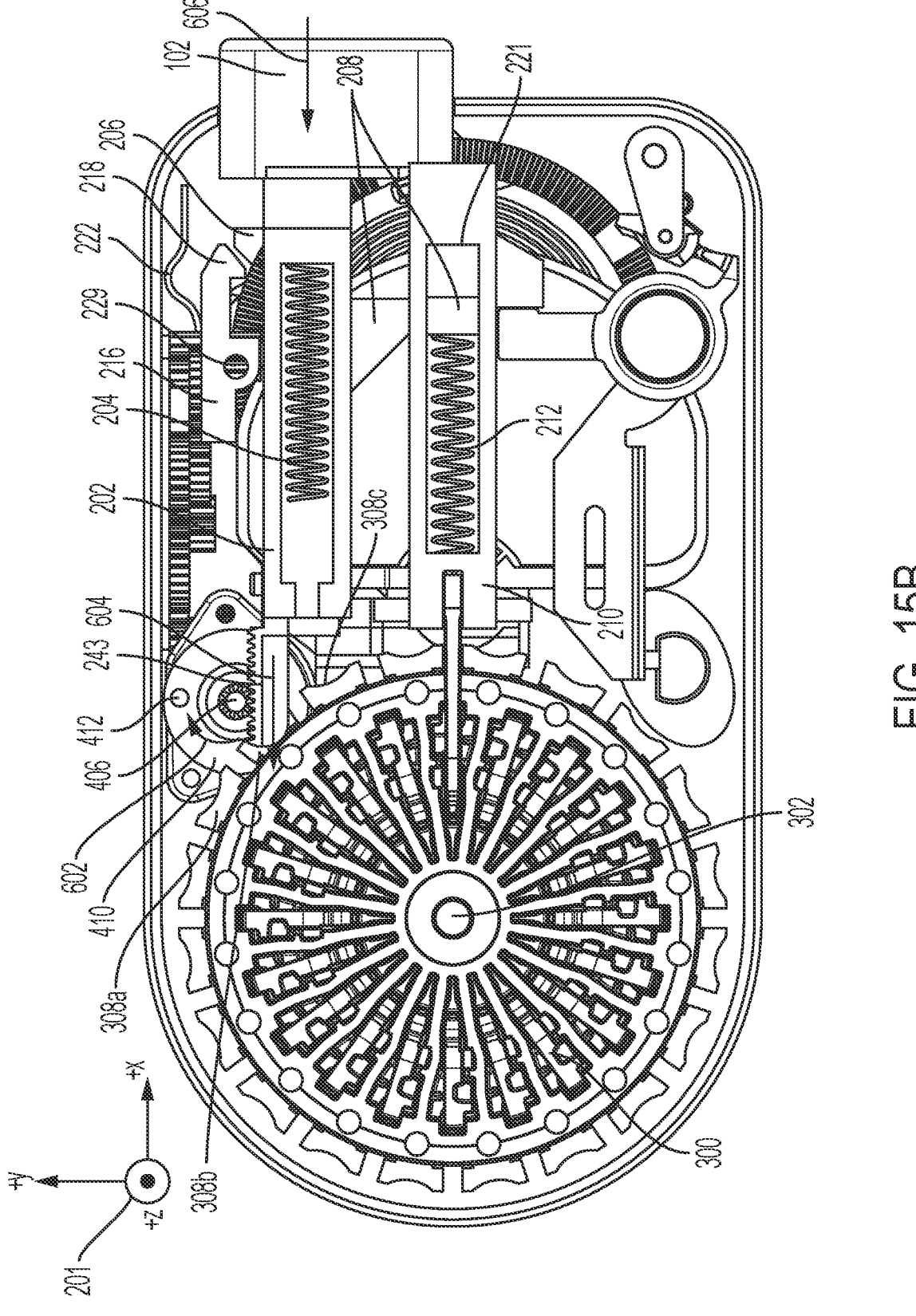

FIG. 15B depicts what happens when a user begins to apply a force in the proximal direction on loading button 102, as depicted by arrow 606. Movement of loading button 102 in the proximal direction causes secondary slide 202 to translate in the proximal direction parallel to the x-axis of device 100, thus compressing spring 204 against the tab (not shown) extending downwards from the interior surface of upper housing 101. Compression tab 208 of secondary slide 202 also translates in the proximal direction within primary slide 210, thus compressing spring 212 against the interior surface of proximal wall 225 of primary slide 210. In this way, movement of secondary slide 202 in the proximal direction compresses both spring 204 and spring 212. As secondary slide 202 translates in the proximal direction, locking tab 206 eventually pushes against latch tab 218 of latch 216. Both locking tab 206 and latch tab 218 comprise sloped surfaces that, when pushed together, causes latch 216 to rotate counter-clockwise (when viewed from the top down) about axis 229, as shown by arrow 608 in FIG. 15C. Eventually, as secondary slide 202 continues to translate proximally, locking tab 206 clears latch tab 218, at which point latch 216 rotates clockwise (when viewed from the top down) about axis 229, as shown by arrow 610 in FIG. 15D, due to the biasing pressure of spring 222. As depicted in FIG. 15D, latch tab 218 slides into place behind (i.e., distal to) locking tab 206, thus preventing secondary slide 202 from translating distally. The position of secondary slide 202 depicted in FIG. 15D is referred to herein as the secondary slide proximal position.

Figure 15C:
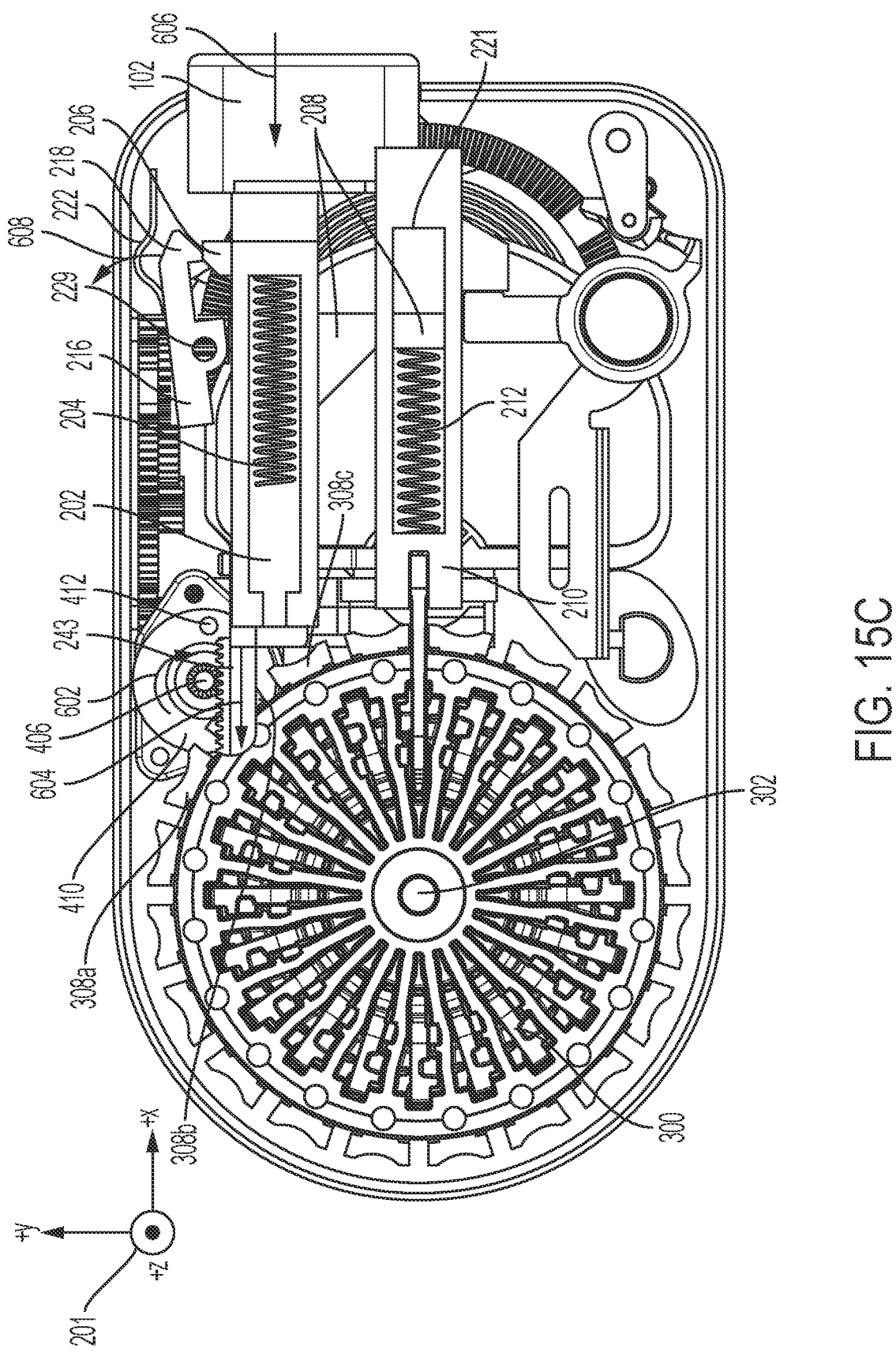
Figure 15D:
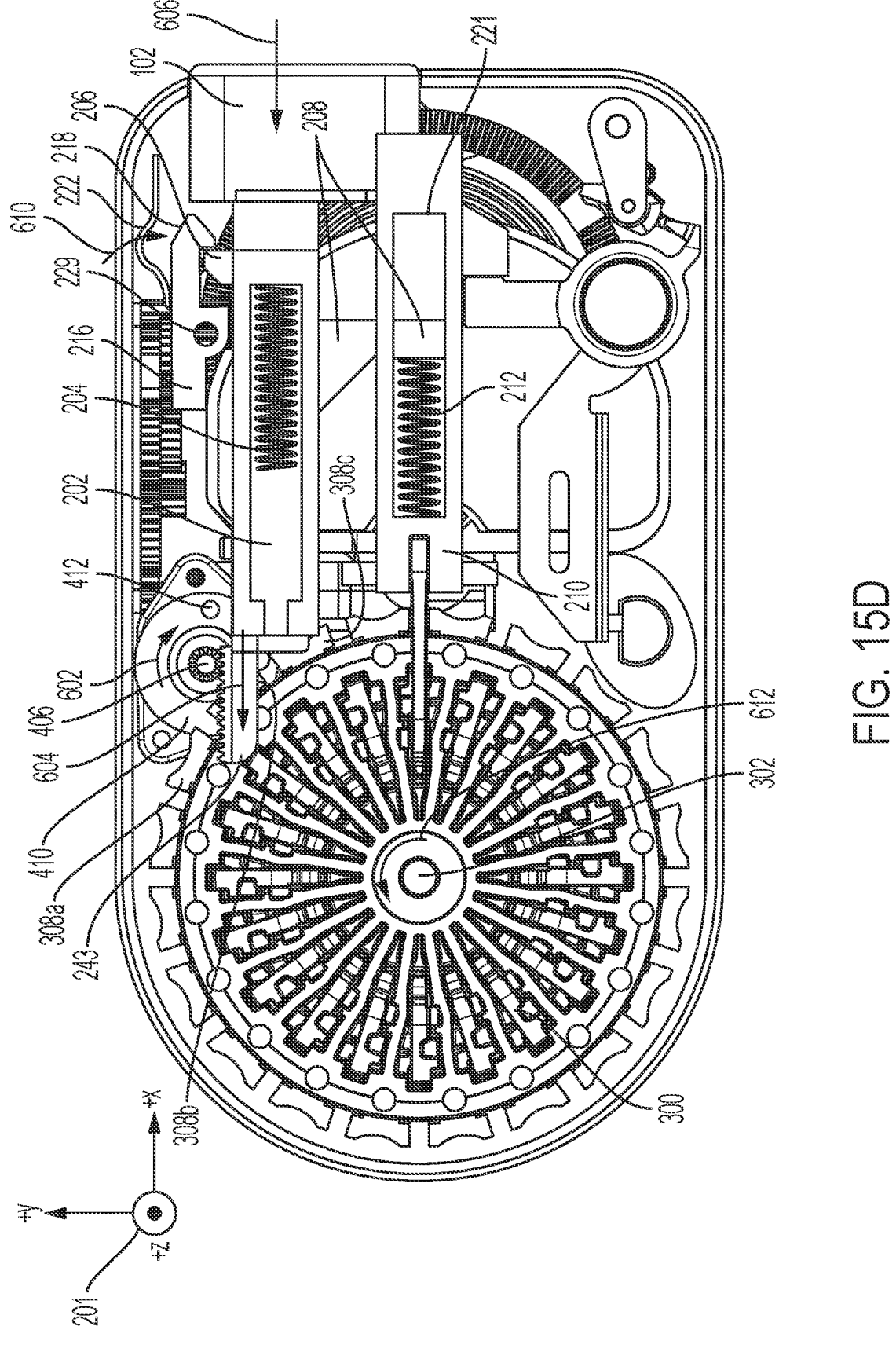
Figures 18A, 18B, 18C:
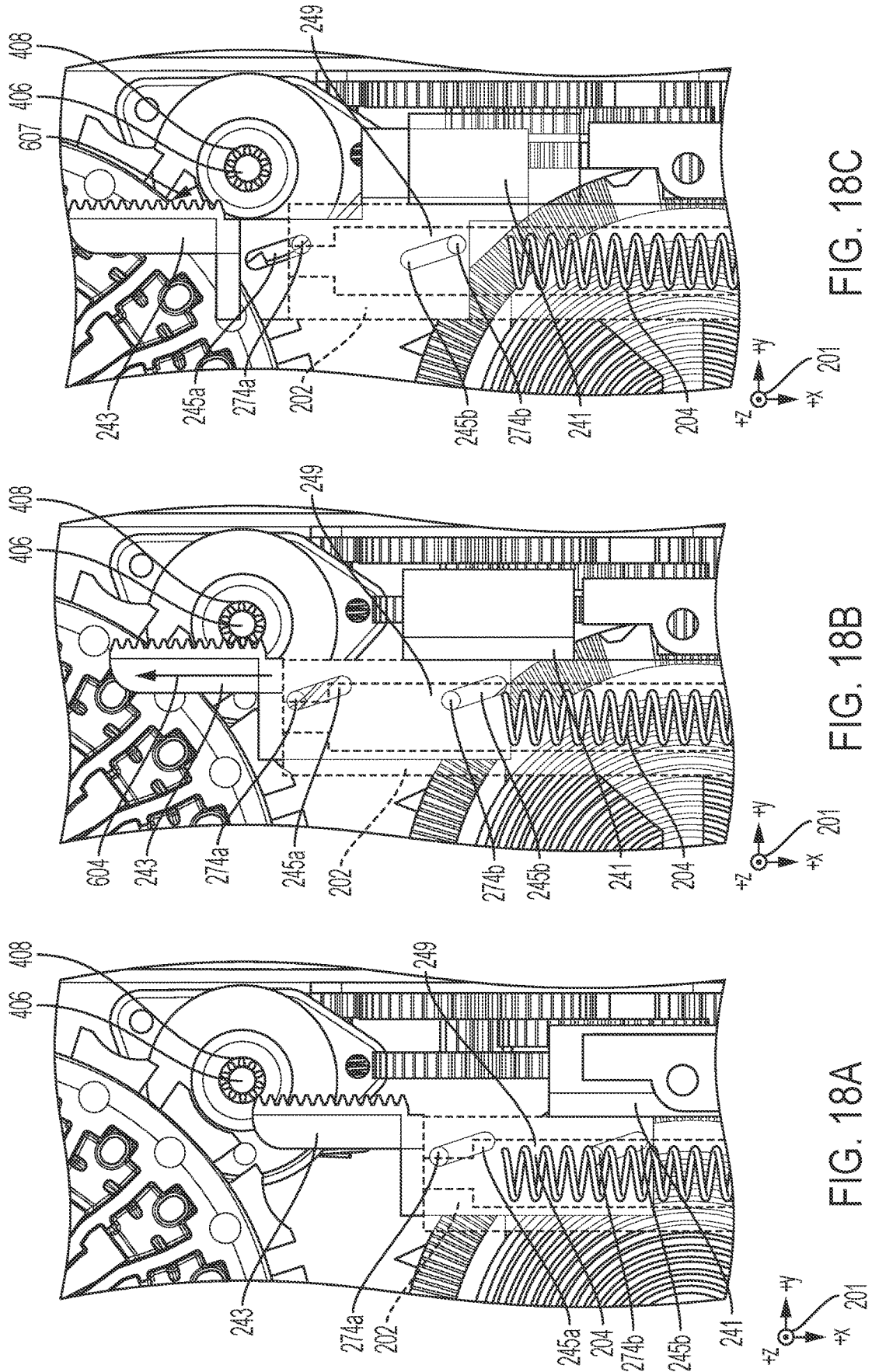
FIG. 18A, FIG. 18B, and FIG. 18C show dis-engagement of a side-facing slide rack component from a pinion coupler component in the exemplary drug-delivery device.

Proximal movement of secondary slide 202 also causes side-facing slide rack 243 to translate in the proximal direction, as shown by arrow 604 in FIGS. 15B-D. Due to the engagement between the teeth of side-facing slide rack 243 and teeth 408 of pinion coupler 406, proximal movement of side-facing slide rack 243 causes pinion coupler 406 to rotate in the clockwise direction (when viewed from the top down), as shown by arrow 602. Due to the rotational coupling between pinion coupler 406 and Geneva wheel 410, Geneva wheel 410 also rotates in the direction of arrow 602. Rotation of Geneva wheel 410 causes Geneva pin 412 to disengage from the gap between the two Geneva wheel members 308a, 308b to which pin 412 was initially engaged, as shown in FIG. 15B. As Geneva wheel 410 continues to rotate, pin 412 re-engages with the next gap defined between two Geneva wheel members (308b, 308c) on cartridge 300 in the clockwise direction, as shown in FIG. 15D. This disengagement and re-engagement of pin 412 within the next gap between Geneva wheel members allows cartridge 300 to advance or index one increment in the counter-clockwise direction (when viewed from the top down), as depicted by arrow 612. When the pin 412 is in re-engagement, the pin 412 maintain its position so that the cartridge does not rotate, and the Geneva wheel 410 is inhibited from further rotation as there is disengagement of side-facing rack 243 from teeth 408, which is depicted in FIG. 18C.

By the end of the sequence of states depicted by FIGS. 15A-D, work done by the user in pressing loading button 102 has been converted into potential energy stored in the compressed springs 204 and 212. This potential energy is prevented from being released by latch tab 218, which prevents secondary slide 202 from translating distally and releasing the springs. This potential energy is also prevented from being released by blocker 226, which prevents primary slide 210 from translating proximally (as described below). The work done by the user has also been used to index or advance the cartridge 300 by one increment, thus moving one spent or used needle assembly out of operational alignment with drive member or hammer 502, and placing a new, unused needle assembly into operational alignment with hammer 502.

Figure 16A:
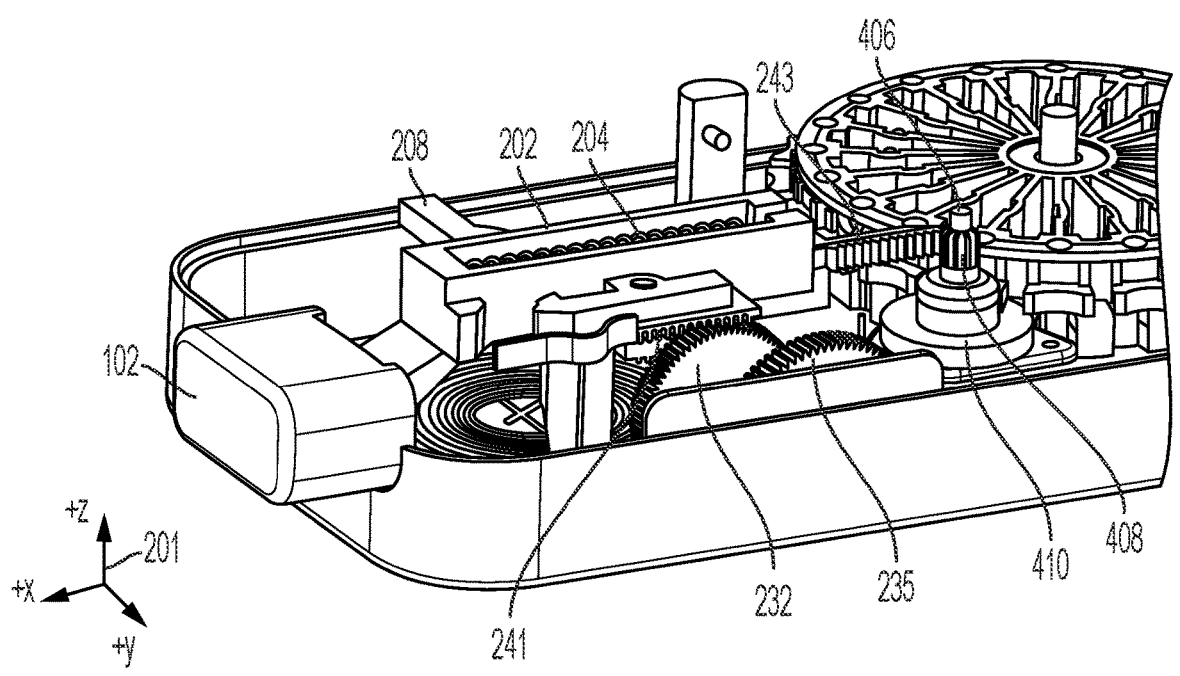
FIG. 16A and FIG. 16B show proximal movement of the secondary slide component caused by depression of the loading button on the exemplary drug-delivery device.
Figure 16B:
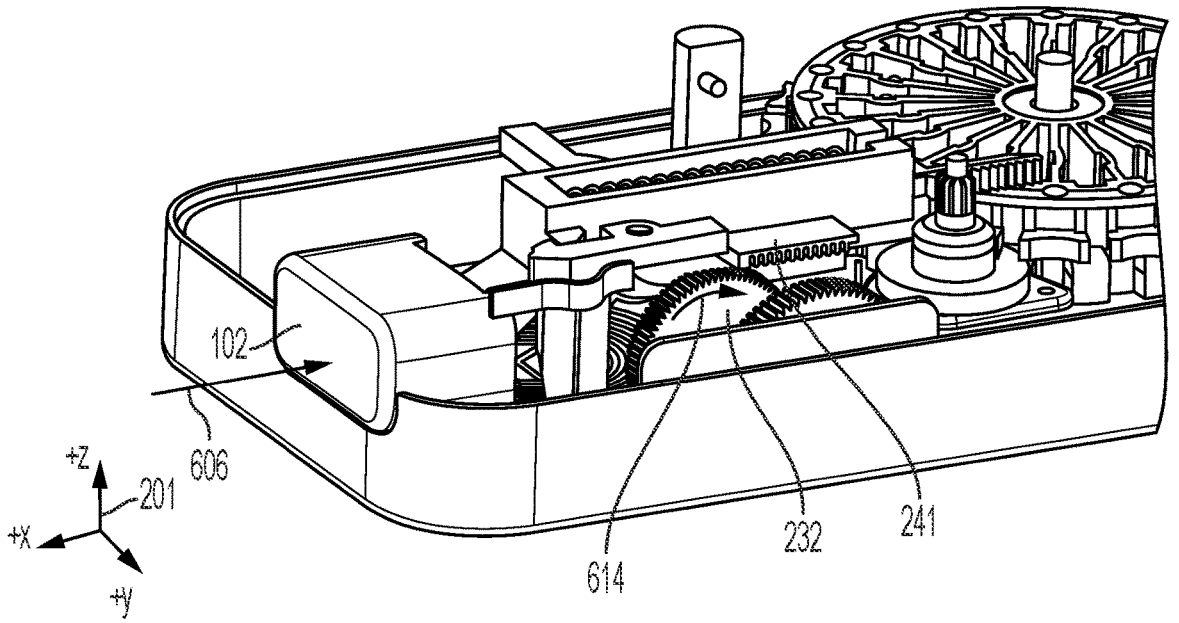

FIGS. 16A and 16B show the proximal movement of secondary slide 202 caused by depression of loading button 102 from the +y side of device 100. FIG. 16A shows the state of device 100 in its neutral state, before loading button 102 is pressed. FIG. 16B depicts the proximal movement of button 102 as the user depresses it, as shown by arrow 606. Proximal movement of button 102 causes secondary slide 202 to translate proximally, which in turn causes downward-facing slide rack 241 to also translate proximally (since slide rack 241 is mounted to secondary slide 202). Due to the engagement between the downward-facing teeth of downward-facing slide rack 241 and gear 232, proximal movement of downward-facing slide rack 241 causes gear 232 to rotate in the direction indicated by arrow 614.

Figure 17A:
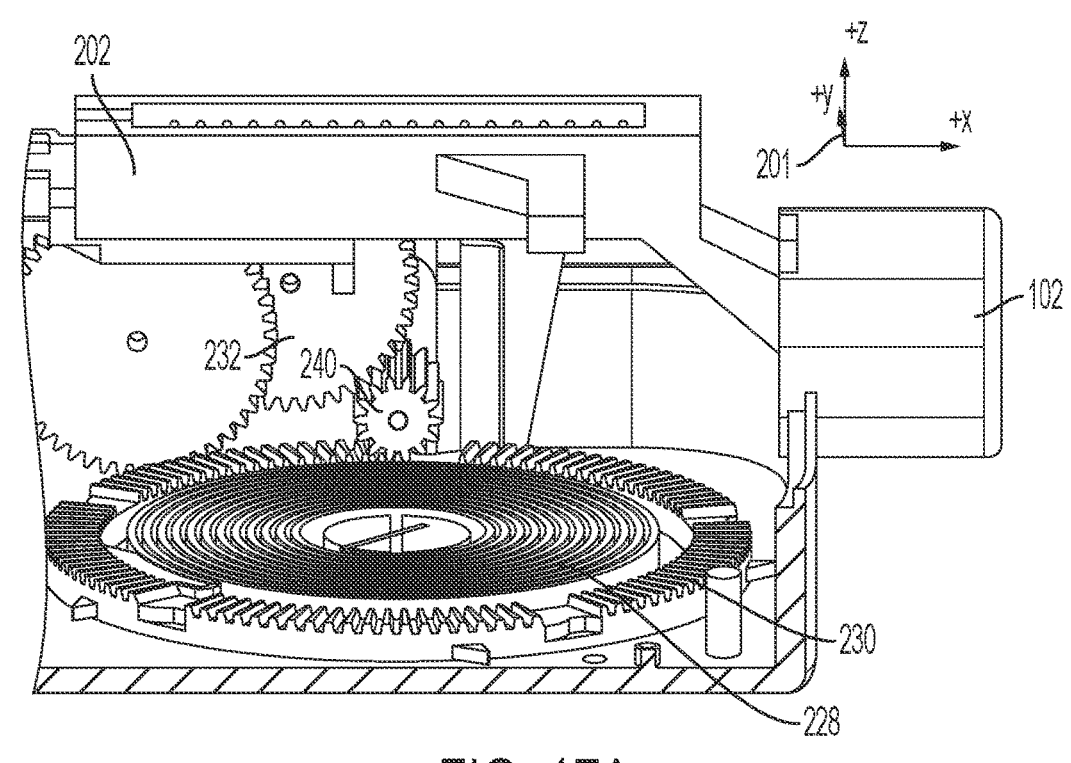
FIG. 17A and FIG. 17B show rotation of a face gear component within the exemplary drug-delivery device.
Figure 17B:
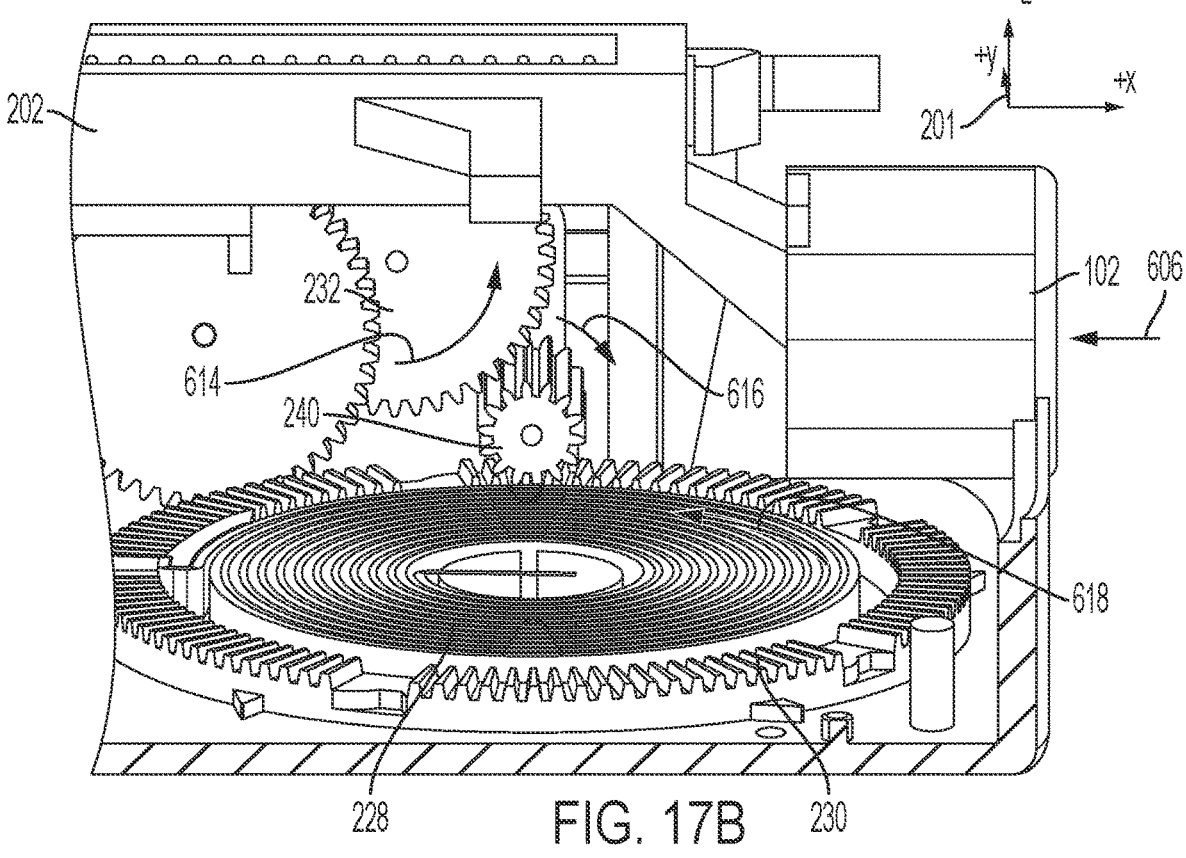

FIGS. 17A and 17B show the results of rotating gear 232 in the direction of arrow 614. For clarity, certain components (e.g., primary slide 210 and drug reservoir 150) have not been depicted to better show the movement of other components. Due to the engagement between gears 232 and 240, rotational movement of gear 232 in the direction of arrow 614 causes gear 240 to rotate in the direction of arrow 616. Rotation of gear 240 in the direction of arrow 616 in turn drives face gear 230 to rotate in the direction of arrow 618. As face gear 230 is rotated in the direction of arrow 618, tension is added to clock spring 228. As previously discussed, face gear 230 defines a plurality of notches 270 on the top surface thereof. As face gear 230 rotates in the direction of arrow 618, one of these notches 270 eventually aligns with pawl 256 of latch assembly 250. When this alignment occurs, pawl 256 slides into notch 270 under the biasing pressure of torsion v-spring 258, thus preventing face gear 230 from rotating counter to the direction indicated by arrow 618.

By the end of the sequence of states depicted by FIGS. 16A-B and FIGS. 17A-B, the work done by the user in pressing loading button 102 has also been converted into potential energy stored in the rotational tension of clock spring 228. This potential energy is prevented from being released by pawl 256, which interacts with one of the notches 270 of face gear 230 to prevent face gear 230 and clock spring 228 from unwinding.

After cartridge 300 has been advanced one increment (as described above in FIGS. 15A-D) and after face gear 230 has been rotated and locked (as described above in FIGS. 16A-B and 17A-B), side-facing slide rack 243 may be disengaged from teeth 408 of pinion coupler 406, and downward-facing slide rack 241 may be disengaged from gear 232. Disengagement of side-facing rack 243 from teeth 408 is depicted in FIGS. 18A-C, which depict a top-down view of device 100. For clarity, secondary slide 202 has been rendered transparent using dashed lines in order to reveal the components underneath it. As apparent from this view, both side-facing slide rack 243 and downward-facing slide rack 241 are mounted to a common slide rack platform 249. Slide rack platform 249 is a substantially planar structure that lies in the horizontal plane of device 100 and is in turn mounted below secondary slide 202. Platform 249 defines two slide rack slots 245a, 245b which extend diagonally in the +x/+y direction in the horizontal plane. Two underside pins 274a, 274b extending downward from the bottom wall 205 of secondary slide 202 fit into the slide rack slots 245a, 245b, respectively.

FIG. 18A depicts an initial, neutral state of device 100 in which secondary slide 202 is positioned at its furthest distal extent (i.e., in the secondary slide distal position such as in FIG. 15A). In FIG. 18B, secondary slide 202 translates proximally in the direction of arrow 604 in response to the user depressing loading button 102, as previously described. As secondary slide 202 translates proximally, underside pins 274a, 274b engage the proximal edges of slide rack slots 245a, 245b, thus causing platform 249, downward-facing slide rack 241, and side-facing slide rack 243 to also translate proximally. When secondary slide 202 completes its proximal translation, platform 249 may continue to slide in the proximal direction such that underside pins 274a, 274b now engage the distal edges of slide rack slots 245a, 245b, as shown in FIG. 18C. Since slide rack slots 245a, 245b extend diagonally in the +x/+y direction, this continued proximal translation of platform 249 in the −x direction causes platform 249 to also translate in the −y direction, as illustrated by arrow 607, radially away from the pinion coupler 406. This translation in the −y direction causes the teeth of side-facing slide rack 243 to disengage from teeth 408 of pinion coupler 406.

Figure 19A:
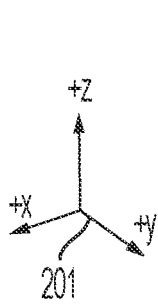
FIG. 19A, FIG. 19B, and FIG. 19C show dis-engagement of a downward-facing slide rack component from a gear component in the exemplary drug-delivery device.
Figure 19A:
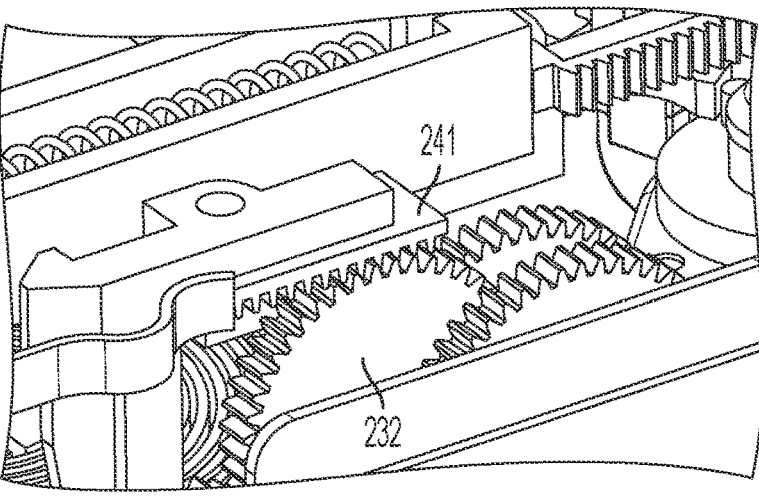
Figure 19B:
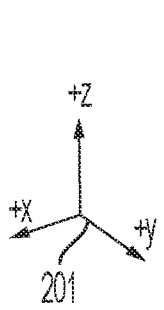
Figure 19B:
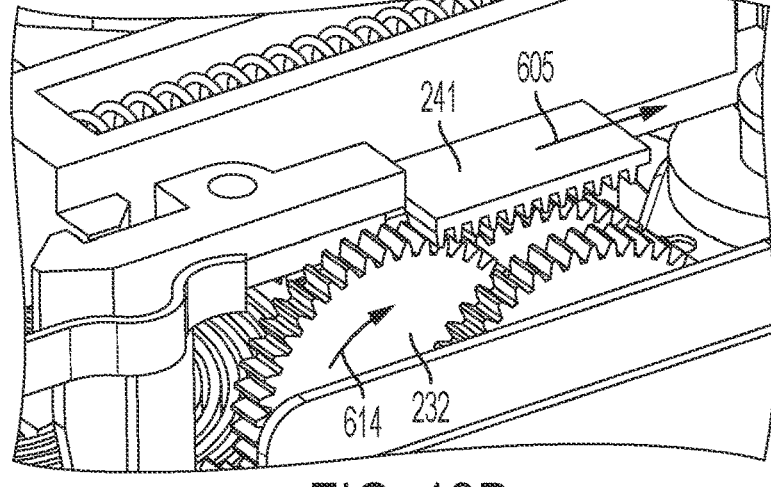
Figure 19C:
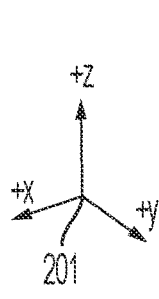
Figure 19C:
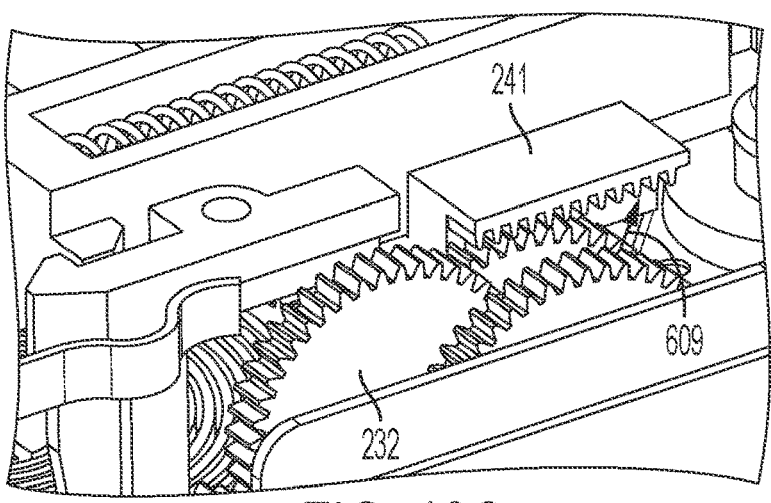

FIGS. 19A-C depict the same sequence of states of device 100 from a different angle, and best illustrates how downward-facing slide rack 241 disengages from gear 232. Similar to FIG. 18A, FIG. 19A depicts the initial neutral state of device 100. FIG. 19B shows how the downward-facing slide rack 241 translates proximally (in the −x direction, as indicated by arrow 605) in response to the user depressing loading button 102, as previously described. When platform 249 translates in the −x/−y direction, as previously described and illustrated in FIG. 18C, downward-facing slide rack 241 also translates in the −x/−y direction, as shown by arrow 609 in FIG. 19C. This causes the teeth of downward-facing slide rack 241 to disengage from the teeth of gear 232.

Figures 20A, 20B:
FIG. 20A and FIG. 20B show how pressing the exemplary drug-delivery device against a patient's body unlocks a dosing button component.

After device 100 has been loaded by pressing loading button 102 and slide racks 241, 243 have been disengaged from gear 232 and pinion coupler 406, respectively, device 100 is ready to be placed onto the patient's body for an injection. FIG. 20A shows the configuration of device 100 after it has been loaded, but before it has been pressed against the patient's body. In this configuration, blocker member 236 of dosing button lock 224 is positioned underneath blocker 226, thus preventing blocker 226 from translating downwards. This prevents the user from triggering device 100 prematurely. FIG. 20B depicts what happens when the user presses device 100 against the patient's body. Pressing device 100 against the patient's body exerts an upward force on the on-body sensing button 106, which overcomes the downward biasing pressure of sensing button spring 114 and causes button 106 to translate upwards into sensing button cavity 120 in the direction of arrow 620. As on-body sensing button 106 translates upwards, pin 118 rides within pin slot 244 of dosing button lock 224, as previously described. Since pin slot 244 in vertical panel 232 extends diagonally in the +x/+z direction, the movement of pin 118 upwards within pin slot 244 also causes dosing button lock 224 to translate in the proximal direction (i.e., in the −x direction), as illustrated by arrow 622. As dosing button lock 224 translates proximally, blocker member 236 clears blocker 226, thus allowing blocker 226 to translate downwards (i.e., in the direction of arrow 624). This unlocks dosing button 104, thus readying device 100 for an injection.

Figure 21A:
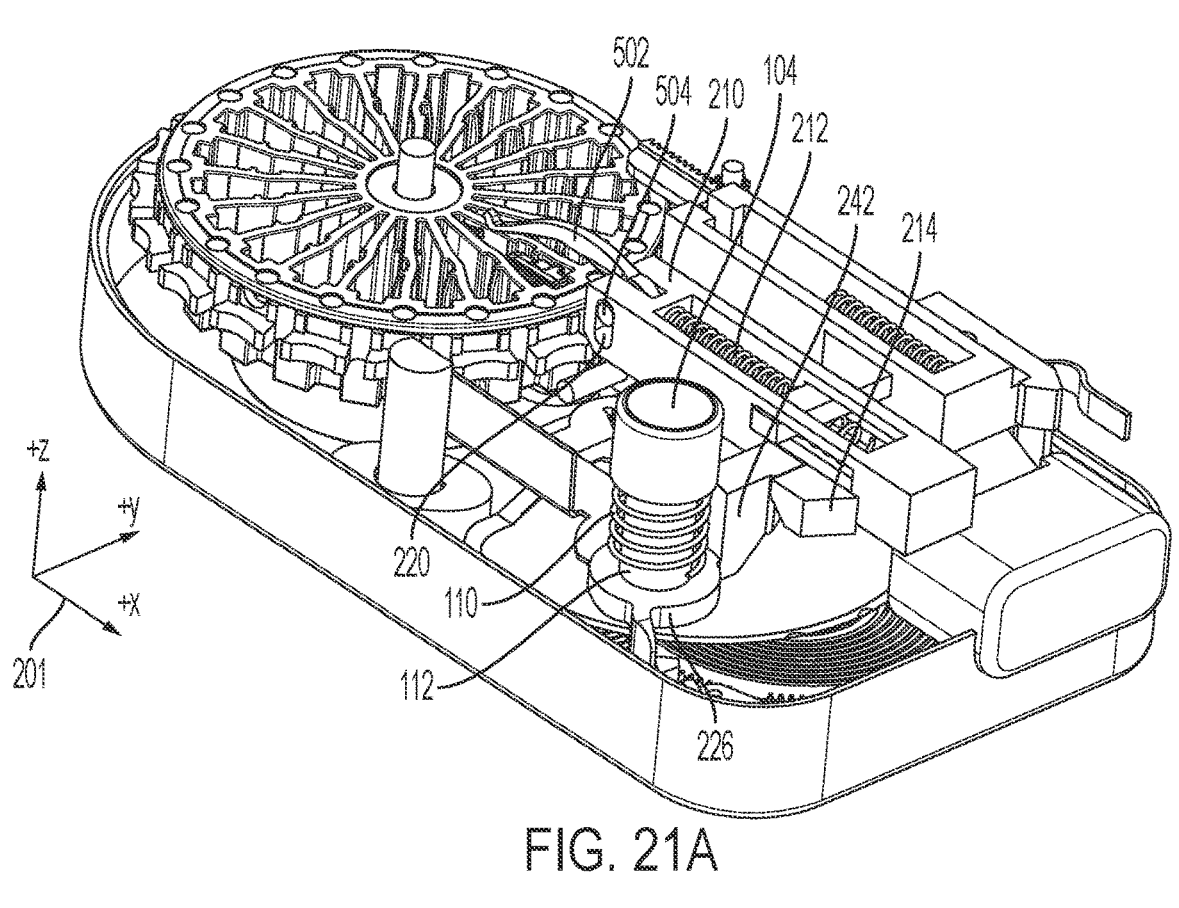
FIG. 21A and FIG. 21B show how pressing the dosing button component releases a primary slide component to translate proximally in the exemplary drug-delivery device.
Figure 21B:
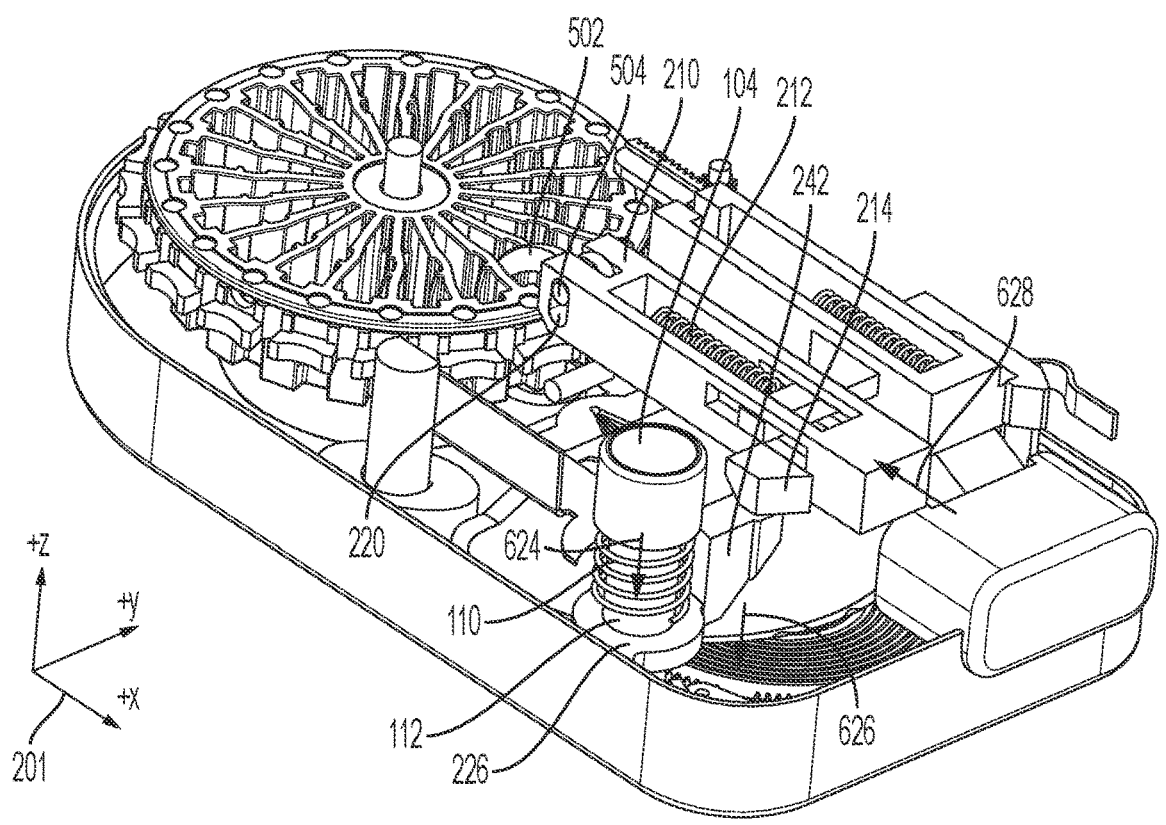

FIG. 21A depicts the configuration of device 100 after it has been pressed against the patient's body (thus unlocking dosing button 104), but before the dosing button 104 has been depressed. In this state, blocking tab 242 of blocker 226 is positioned in front of locking tab 214 of primary slide 210, thus preventing primary slide 210 from translating proximally in the −x direction. As previously discussed, this position of primary slide 210 is referred to herein as the primary slide distal position. FIG. 21B depicts what happens when the user depresses dosing button 104. As dosing button 104 is depressed downward in the direction of arrow 624, the downward force provided by the user overcomes the upward biasing pressure of dosing button spring 110 and causes button 104 to translate downwards. The downward force on button 104 is transmitted to blocker 226 via dosing button shaft 112. This causes blocker 226 to also translate downwards in the direction of arrow 626. As blocker 226 translates downwards, blocking tab 242 clears the locking tab 214 of primary slide 210, thus allowing primary slide 210 to translate proximally in the direction of arrow 628 (i.e., in the −x direction). Since spring 212 has been previously compressed by proximal movement of compression tab 208 of secondary slide 202 (as previously described), primary slide 210 is propelled proximally by the loaded spring 212 once blocking tab 226 clears locking tab 214. The position of primary slide 210 when it has translated to its maximum proximal extent is referred to herein as the primary slide proximal position.

FIGS. 22A-B provide profile views of device 100 showing how proximal movement of primary slide 210 drives a needle assembly 306 within cartridge 300 from a retracted position to an injection position. FIG. 22A shows the configuration of device 100 before the user presses dosing button 104. In this state, needle assembly 306 is disposed in a retracted position within cavity 304 of cartridge 300. When primary slide 210 is propelled forward by spring 212, primary slide 210 exerts a proximal force in the direction of arrow 630 on pin 504 of hammer 502. This proximal force causes hammer 502 to rotate around pin 506 in the direction of arrow 631. As hammer 502 rotates in the direction of arrow 631, hammer head 503 pushes down on ledge 328 of a needle assembly 306 within cartridge 300 that is in operational alignment with hammer 502, thus driving that needle assembly downwards in the direction of arrow 632 to an injection position, as shown in FIG. 22B. As needle assembly 306 translates downwards, first leg segment 324 of needle 312 penetrates drug septum 182, while second leg segment 326 of needle 312 projects downward out of needle aperture 108 in lower housing 103, punctures the patient's skin and into the patient's body. In this way, when needle assembly 306 is in its injection position, needle 312 establishes a fluid path from drug septum 182 into the patient's body. When the needle assembly is disposed in the injection position, the biasing force of spring 212 biases primary slide 210 in the proximal direction, thus causing hammer head 503 to maintain downward pressure on ledge 328 until the needle assembly is retracted (as described below). This ensures the needle assembly maintains its proper depth within the patient's body and in the drug septum 182.

In addition to unlocking primary slide 210, downward translation of blocker 226 also drives latch assembly 250 to unlock face gear 230. The interaction between blocker 226 and latch assembly 250 is best depicted in FIGS. 23A-C. FIG. 23A shows the spatial position of blocker 226 relative to latch assembly 250 before the user presses down on dosing button 104. In this initial position, fin 232 of blocker 226 is positioned just above latch pin 252 of latch assembly 250. As blocker 226 is driven downwards when the user depresses button 104, bottom surface 262 of fin 232 contacts latch pin 252. Since bottom surface 262 is angled diagonally in a −x/+z direction, downward movement of bottom surface 262 causes pin 252 to rotate horizontally in the direction indicated by arrow 638 around axis 264 (see FIGS. 23B and 23C). As pin 252 rotates in the direction of arrow 638, torsion v-spring 258 transmits rotational torque on pawl 256 in the direction of arrow 640 (again around axis 264).

Figures 24A, 24B, 24C:
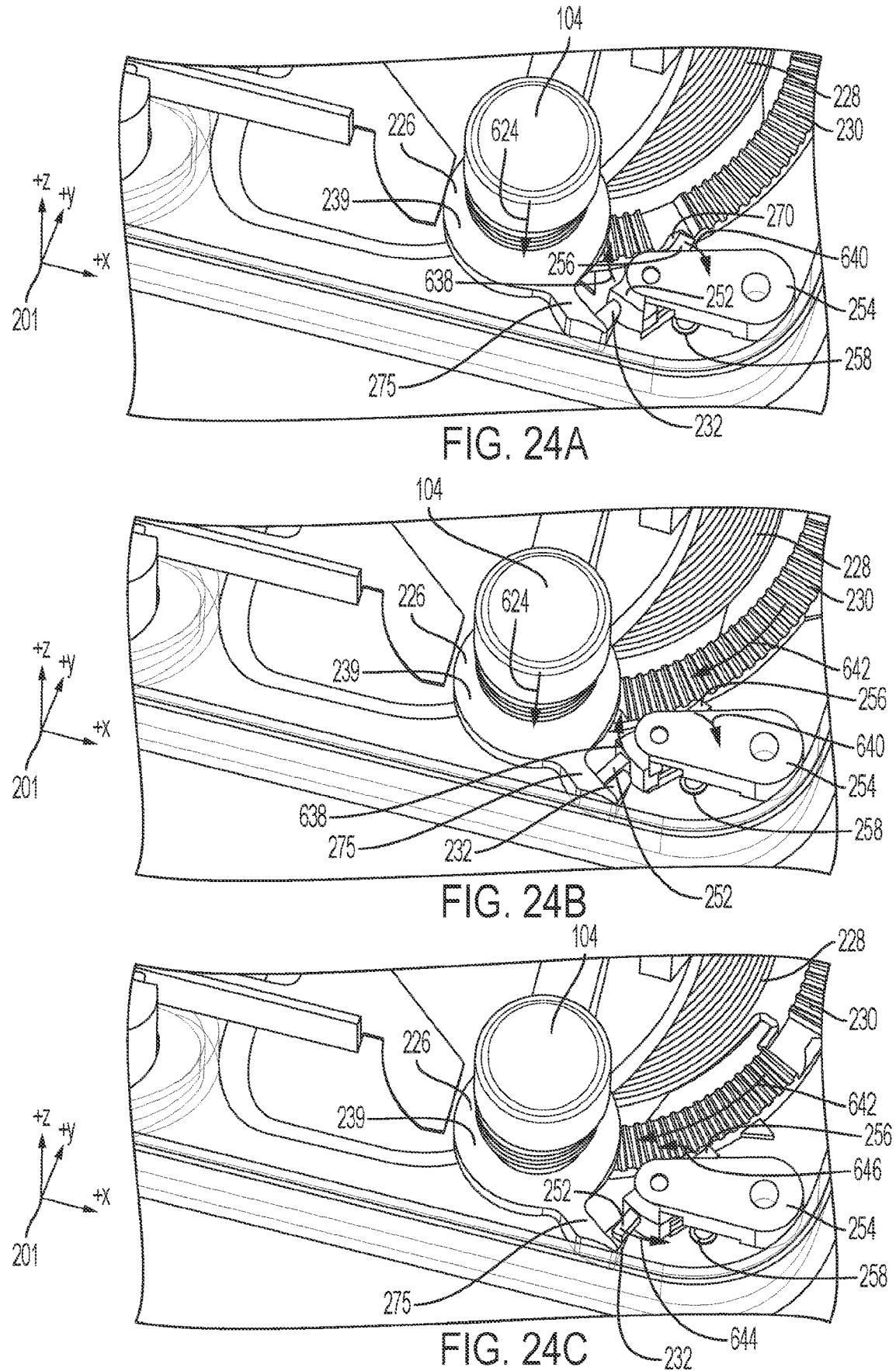
FIG. 24A, FIG. 24B, and FIG. 24C show how actuation of the dosing button releases unwinding of the face gear component in the exemplary drug-delivery device.

FIGS. 24A-C show the interaction between blocker 226 and latch assembly 250 from another angle. FIG. 24A shows the state of device 100 after the user has loaded the device by depressing loading button 102, but before the user has depressed button 104. In this state, work done by the user in depressing loading button 102 is stored in the form of potential energy within coiled clock spring 228, which is coupled to face gear 230. However, face gear 230 and clock spring 228 are prevented from unwinding by pawl 256, which fits within one of the notches 270 defined on face gear 230. As the user depresses dosing button 104, button 104 translates downward in the direction of arrow 624. This downward force on button 104 causes blocker 226 to also translate downward and, as previously discussed, causes latch pin 252 to rotate in the direction of arrow 638, and pawl 256 to rotate in the direction of arrow 640. Rotation of pawl 256 in the direction of arrow 640 causes pawl 256 to disengage from notch 270, thus allowing face gear 230 and clock spring 228 to unwind in the direction of arrow 642, as depicted in FIG. 24B.

Referring back to FIG. 23C, as the user continues to push downward on loading button 104, and as blocker 226 continues to translate downward, latch pin 252 eventually leaves contact with bottom surface 262 of fin 232, and instead contacts proximal surface 266 of fin 232. At this point, latch pin 252 stops rotating in the direction of arrow 638. As blocker 226 continues to translate downward, latch pin 252 clears proximal surface 266 as the entire fin 232 slips underneath latch pin 252. When the user stops pushing downward on button 104, button 104 and blocker 226 rise upward again due to the biasing pressure of dosing button spring 110. At this point, latch pin 252 contacts top surface 260 of fin 232. Since top surface 260 of fin 232 is also angled diagonally in a −x/+z direction, top surface 260 now forces latch pin 252 to rotate in the opposite direction around axis 264, i.e., in the direction of arrow 644. As pin 252 rotates in the direction of arrow 644, torsion v-spring transmits rotational torque on pawl 256 in the direction of arrow 646.

Figures 25A, 25B, 25C:
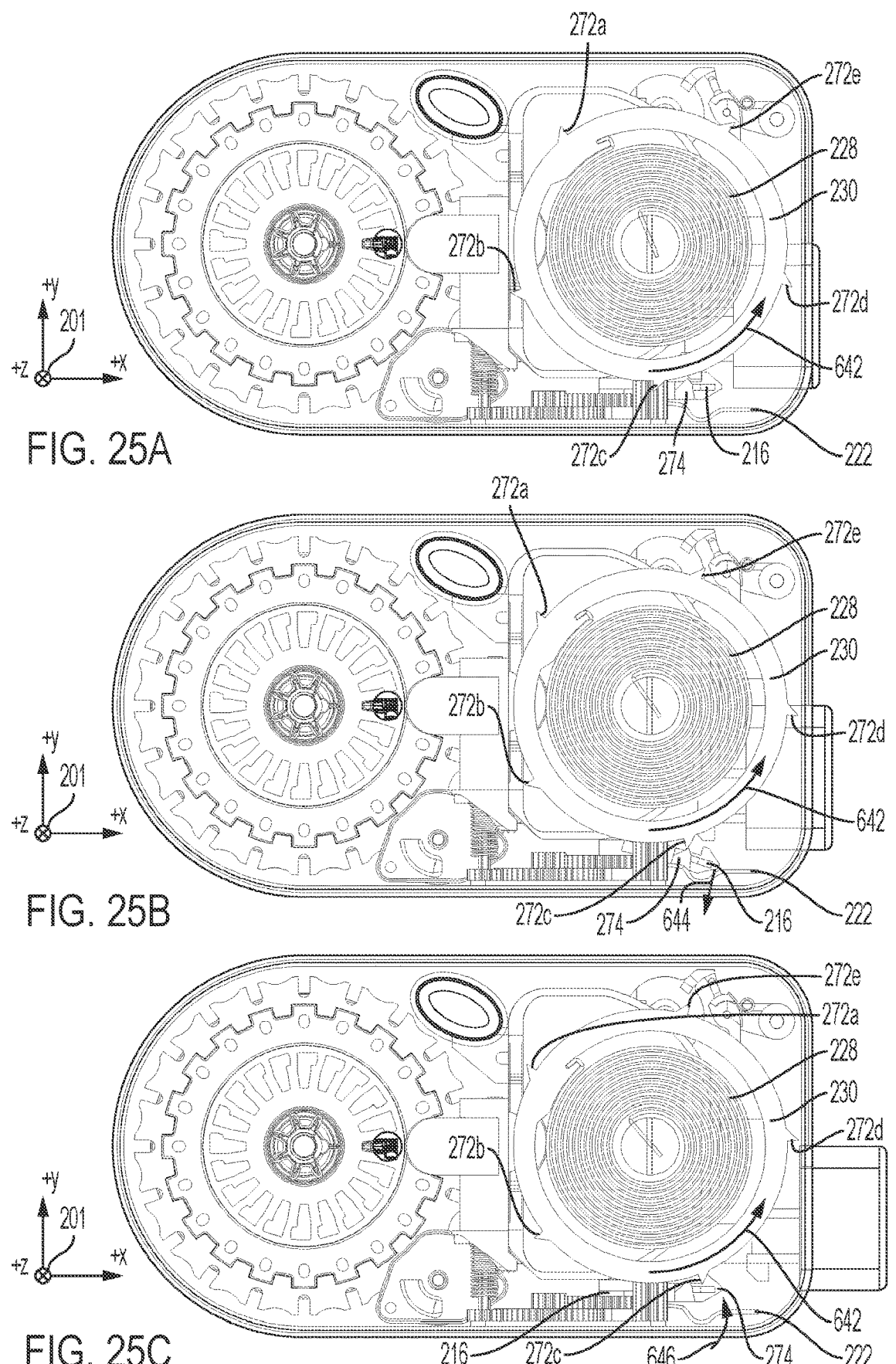
FIGS. 25A, 25B, and 25C show how unwinding of the face gear component releases a slide latch component in the exemplary drug-delivery device.

FIGS. 25A-C provide a view of device 100 from below, in which lower housing 103 has been rendered transparent to better show how the unwinding of face gear 230 unlatches latch 216. FIG. 25A depicts device 100 after pawl 256 has been disengaged from one of the notches 270 in face gear 230 and face gear 230 and clock spring 228 begin unwinding in the direction of arrow 642. While face gear 230 and clock gear 228 are unwinding, the needle insertion/retraction mechanism 500 drives a needle assembly 306 into the injection position, as previously discussed and depicted in FIGS. 22A-B. Also, while face gear 230 unwinds, it drives rotation of gears 240, 232, 234, 235, and 238 (see FIG. 6). Rotation of gear 238, in turn, provides rotational input to pump 180, causing pump 180 to pump liquid drug from reservoir 150, through septum 182 and the driven needle 312 and into the patient.

Figure 29:
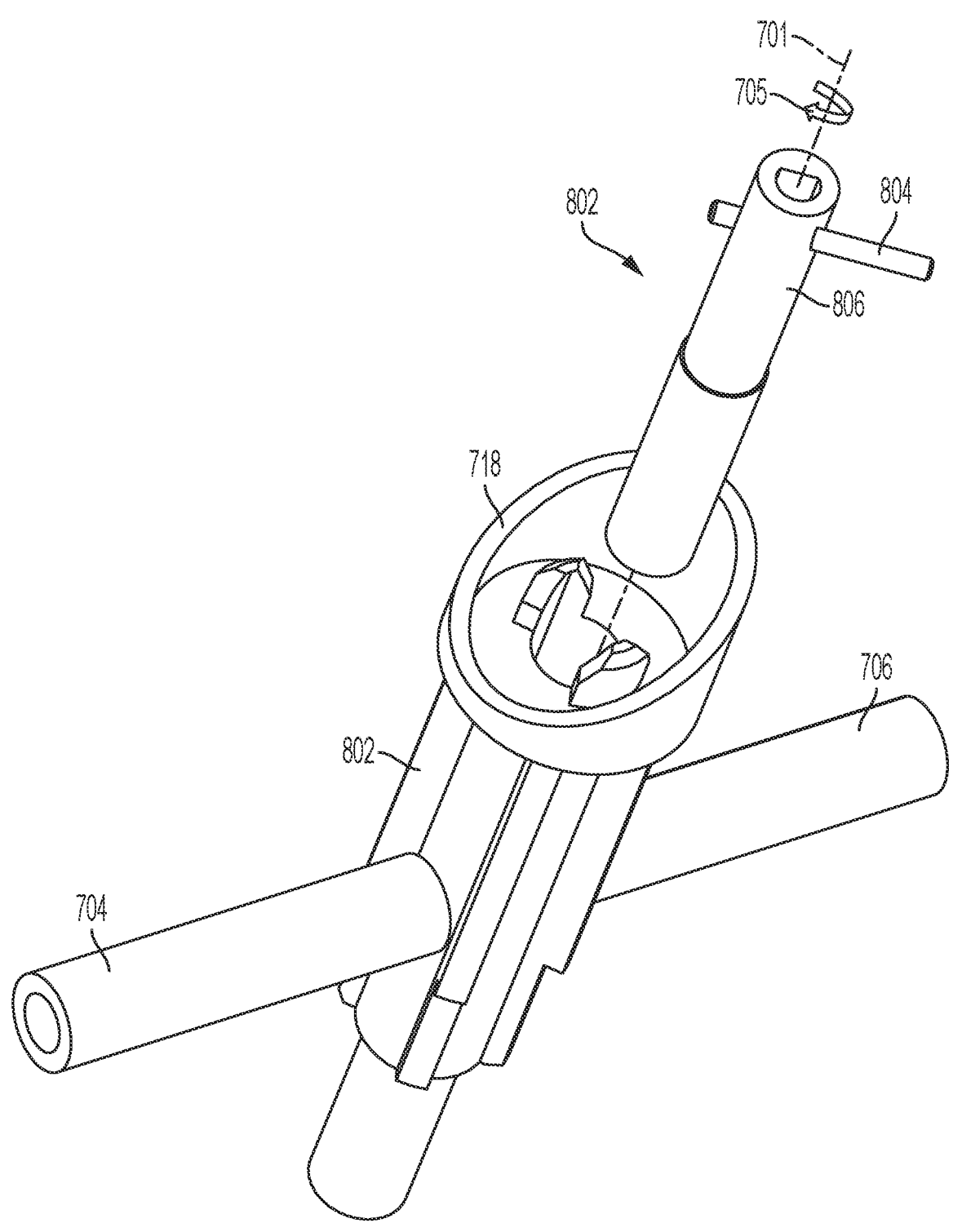
FIG. 29 shows an exploded view of the drug pump embodiment.
Figure 30A:
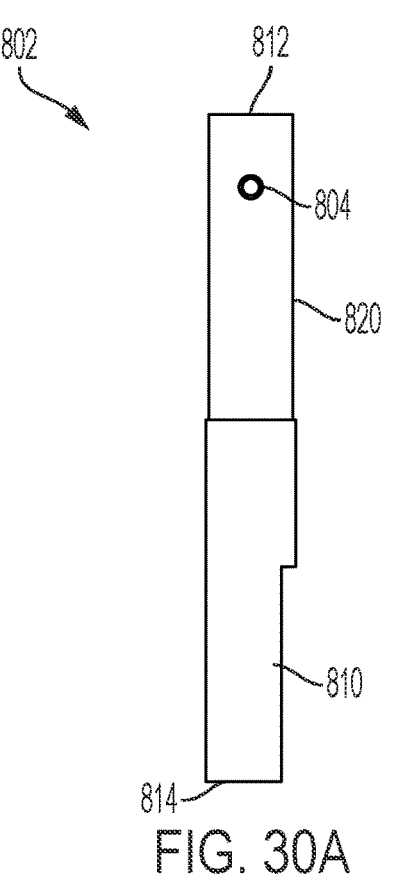
FIGS. 30A, 30B, 30C, and 30D show different profile views of a rotating plunger component within the drug pump embodiment.
Figure 30B:
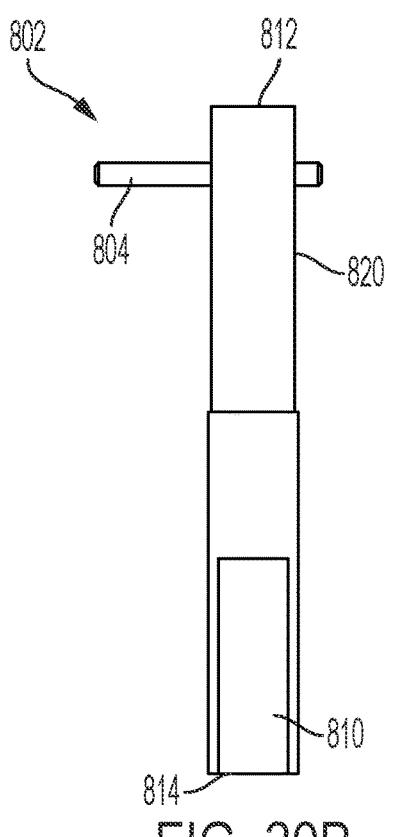
Figure 30C:
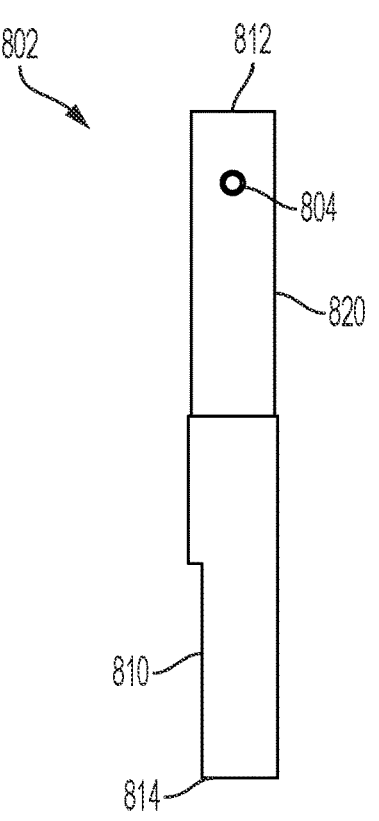
Figure 30D:
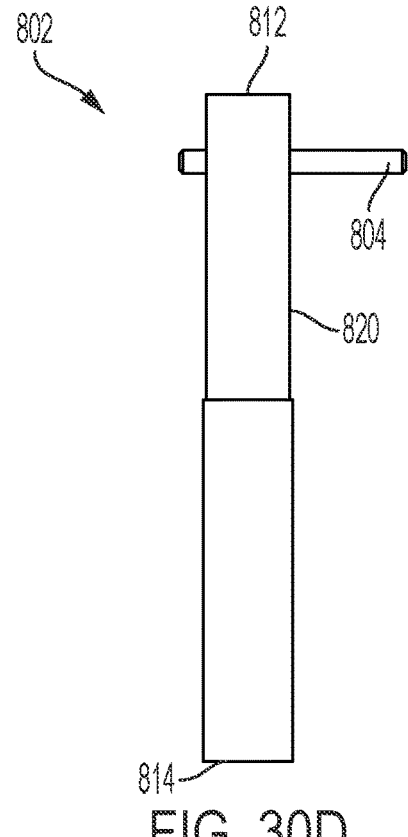

FIGS. 28 through 35A-D depict one potential embodiment of pump 180. Pump 180 includes mounting frame 602, rotary drive shaft 604, rotating plunger 802, pump housing 702, and return spring 624. A first end of frame 602 supports a rotary drive shaft 604, which is in turn connected to rotating plunger 802. Rotary drive shaft 604 may be connected to gear 238, which provides rotational input to pump 180 that causes rotary drive shaft 604 to rotate about longitudinal axis 701 in the direction of arrow 705 (e.g., in a clockwise direction), as shown in FIG. 29.

Figure 31:
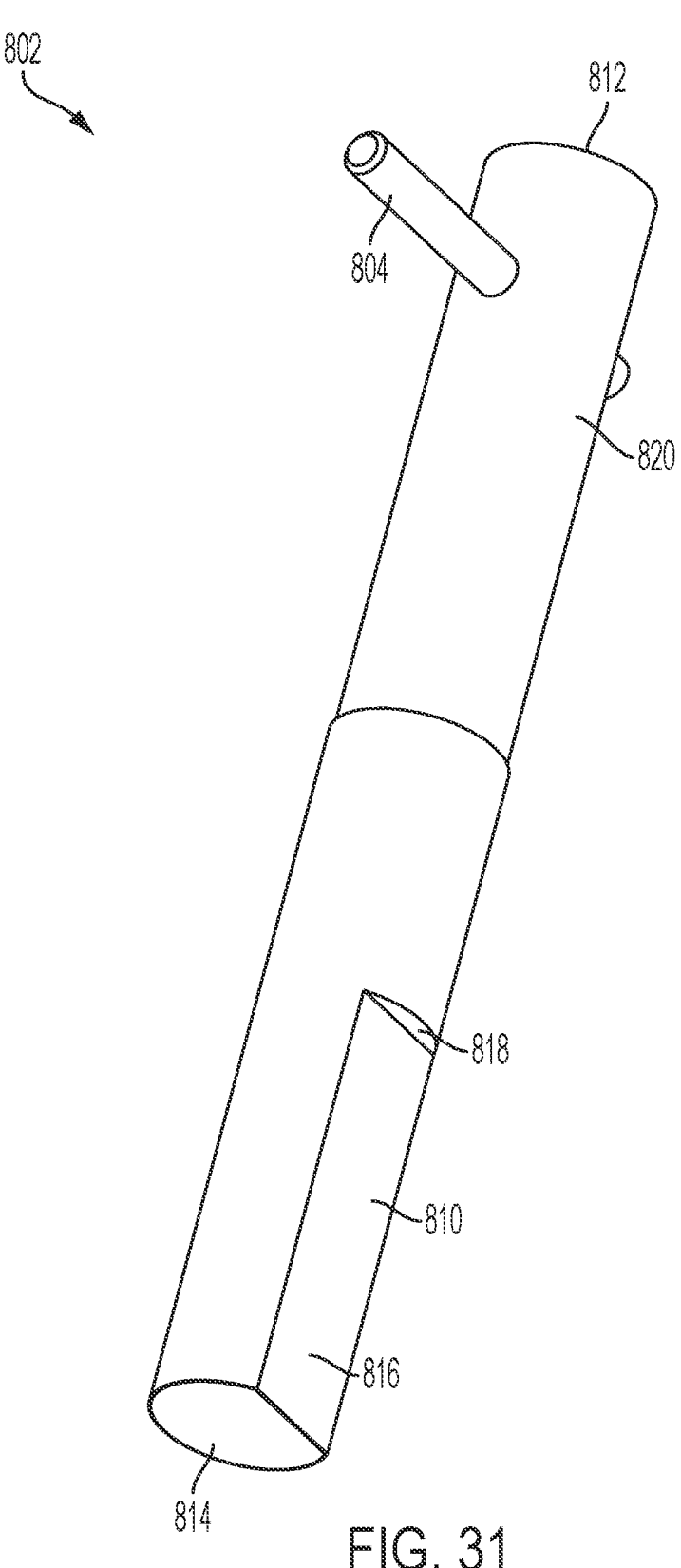
FIG. 31 shows a perspective view of the rotating plunger component within the drug pump embodiment.

FIGS. 30A-30D and 31 depict the rotating plunger 802 in more detail, according to some embodiments. FIGS. 30A-30D depict plunger 802 from four separate profile views, while FIG. 31 provides a perspective view. Plunger 802 comprises a substantially cylindrical elongated body having a first end 812 and a second end 814 connected by curved, cylindrical side wall 820. Plunger pin 804 protrudes radially outward from side wall 820 of plunger 802 and may be rigidly affixed thereto. In some embodiments, pin 804 and side wall 820 may be formed of one monolithic piece; in other embodiments, pin 804 may be a separate part that is adhered, joined, inserted, or molded into side wall 820. As depicted, pin 804 may be disposed adjacent to the first end 812 of plunger 802. However, the pin may be disposed at any point along the length of plunger 802. As best seen in FIG. 31, plunger 802 may include a reduced cross-sectional area portion that may be defined by a cutout 810 disposed adjacent to the second end 814. Cutout 810 is defined by a substantially planar longitudinal portion 816 recessed below the side wall 820 and connected to a lip 818 which steps inwards from the cylindrical side wall 820 of plunger 802. Portion 816 and lip 818 may intersect in a transverse relationship. In one embodiment, planar portion 816 of cutout 810 faces a first radial direction, and the pin 804 extends in a second radial direction that is perpendicular to the first radial direction of the placement of the cutout.

Figure 32:
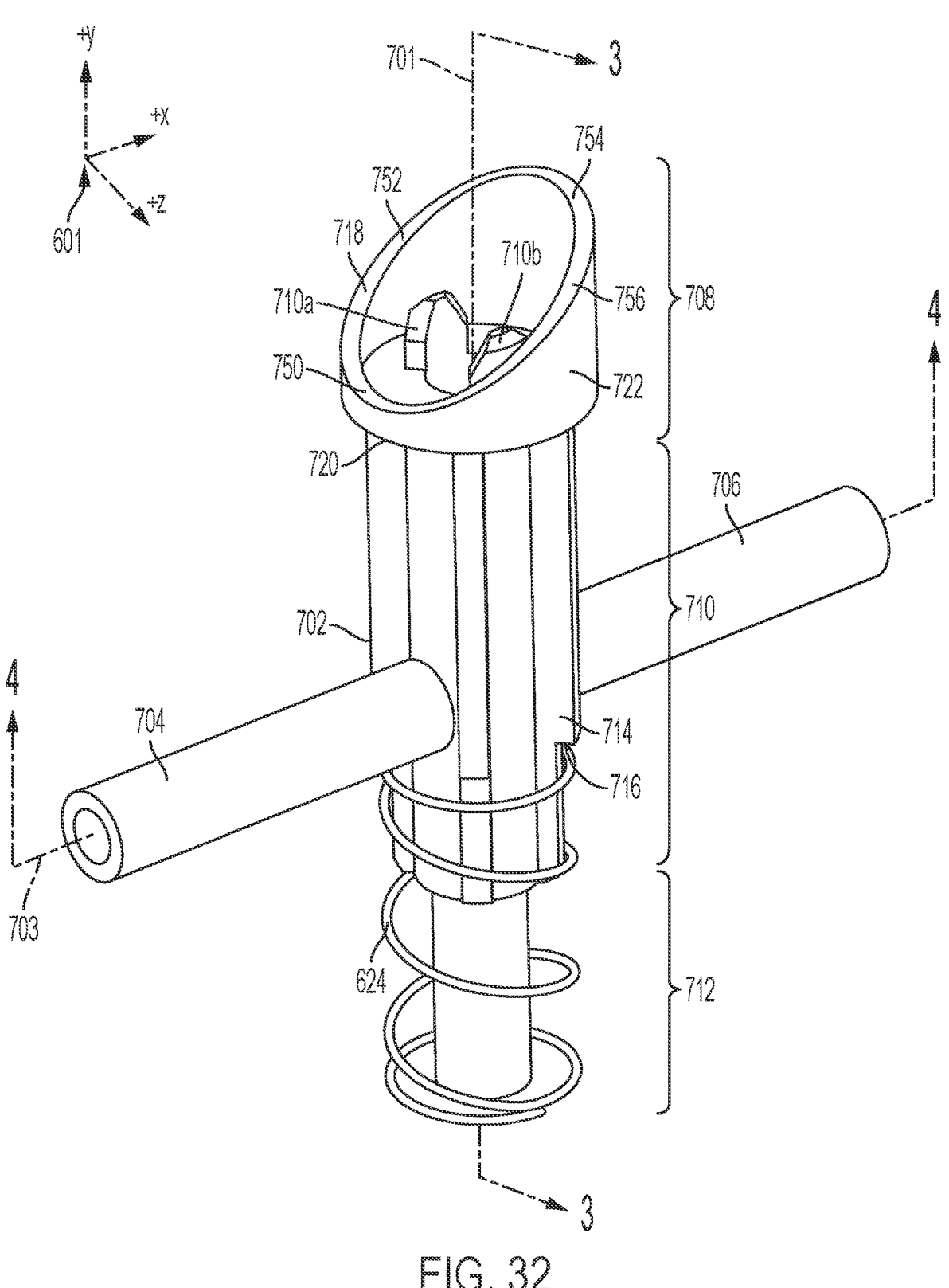
FIG. 32 shows a perspective view of a pump housing component of the drug pump embodiment.
Figure 33:
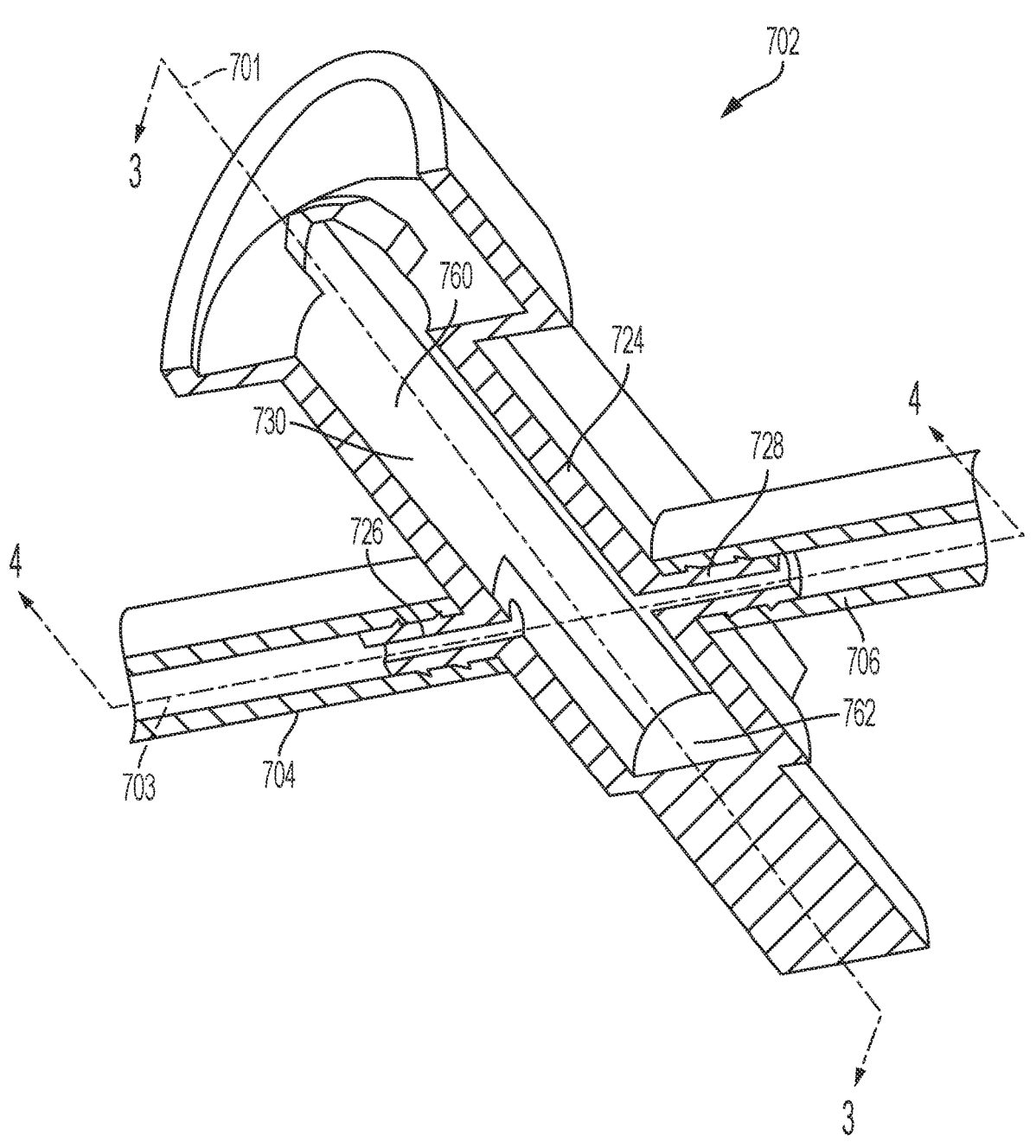
FIG. 33 shows a cutaway view of the drug pump housing component.

Plunger 802 is received within pump housing 702. One exemplary embodiment of housing 702 is depicted in greater detail in FIGS. 32 and 33; FIG. 32 provides a perspective view of housing 702, while FIG. 33 provides a cross-sectional view of housing 202 when cut along line 3-3. Housing 702 may be constructed from any suitable and relatively rigid material, such as an olefin plastic (e.g., cyclic olefin copolymer and/or polypropylene). The interface between housing 702 and plunger 802 may be lubricated with an appropriate pharmaceutical container lubricant, such as silicone oil.

Housing 702 comprises three sections: a first section 708, an intermediate section 710, and a third section 712, each disposed along a common axis 701. First section 708 comprises a side wall 722 that defines an angled pin track 718. Pin track 718 is angled such that a plane defined by track 718 is not perpendicular to longitudinal axis 718 but is angularly offset such that a first end 754 of track 718 is further from intermediate section 710 than the opposite, second end 750 of track 718. Second end 750 is connected to first end 754 of track 718 via an upwardly-sloping portion 752, and a downwardly-sloping portion 756. First section 708 also comprises two tabs 710a, 710b that receive and support plunger 802.

Intermediate section 710 comprises a side wall 724, and one or more axial ridges 714 projecting radially outward from side wall 724. One or more of the ridges 714 have a radially inward step 716 oriented towards the third section

712 of housing 702. As best shown in FIG. 33, side wall 724 defines a cavity 730 internally along the axis 701 having an open first end 760 and a closed second end 762. Side wall 724 also defines an inlet port 726 and an outlet port 728, shown defined by radially extending arms. In one embodiment, the ports 726, 728 are oriented in different radial directions. In one embodiment, the ports 726, 728 are oriented extending in opposite directions (for example, angularly spaced 180 degrees from each other) along a transverse axis 703 that extends orthogonal to the longitudinal axis 701. Inlet port 726 and outlet port 728 pass through side wall 724 and are in fluid communication with cavity 730. Ducts are shown disposed on the arms in a fluid tight seal. Inlet port 726 is fluidically connected with an inlet duct 704, while outlet port 728 is fluidically connected to an outlet duct 706. During operation of the pump subsystem, fluid is sucked in through inlet port 726/inlet duct 704 and into the cavity 730 and expelled through outlet port 728/outlet duct 706.

Returning to FIG. 32, third section 712 of housing 702 comprises a substantially cylindrical body having a smaller cross-sectional area compared to first section 708 and intermediate section 710. Third section 712 may also take the form of other shapes. Return spring 724 may be wrapped around third section 712 such that a first end of spring 624 abuts the inward step 716 of one or more of the ridges 714, and a second end of spring 624 abuts and/or is received within a receptacle on mounting frame 602 (see FIG. 28). Thus mounted, return spring 624 provides biasing pressure against housing 702.

When plunger 802 is received within housing 702, plunger 802 is configured to rotate about longitudinal axis 701 within cavity 730. Plunger 802 is also configured to translate longitudinally along longitudinal axis 701 within cavity 730. The biasing pressure of return spring 624 causes the pin track 718 to abut and/or engage against the underside of plunger pin 804 at all times while plunger 802 rotates within cavity 730. When plunger 802 is received within cavity 730, the surfaces that define cutout 810 (that is, surfaces 816, 818) and the interior wall of cavity 730 (i.e., the interior surface of side wall 724) together define a working chamber 902 (see FIGS. 34A-34D) that is brought into repeated and sequential fluid-flow communication with no port, then the inlet port, then no port, and then the outlet port as the plunger moves within the cavity.

In operation, rotational input from gear 238 provides a rotary force to drive shaft 604. The rotary force causes shaft 604 and plunger 802 to rotate about longitudinal axis 701 in the direction of arrow 705 (see FIG. 29, FIGS. 34A-34D). As plunger 802 rotates within cavity 802, the plunger 802 and housing 702 successively move through the series of configurations depicted in FIGS. 34A-34D, and 35A-35D. Each of FIGS. 34A-34D show a profile, cross-sectional view of pump subsystem 108 along line 3-3. Each of FIGS. 35A-35D show a top-down, cross-sectional view of pump subsystem 108 along line 4-4. For clarity, the position of plunger pin 804 is outlined in phantom in FIGS. 35A-35D.

Figures 34A, 34B, 34C, 34D:
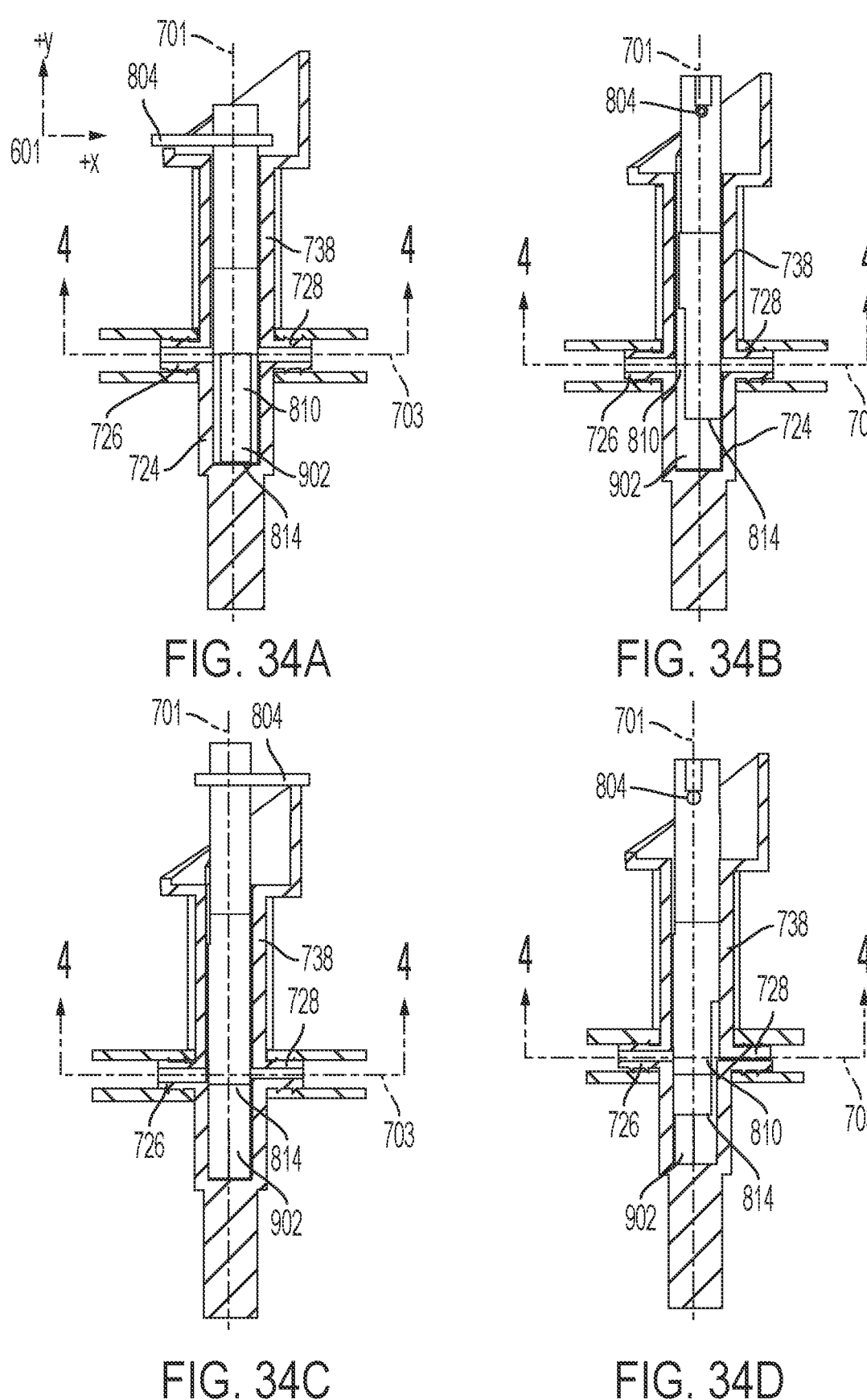
FIGS. 34A, 34B, 34C, and 34D show different cutaway profile views of the drug pump embodiment in operation.
Figures 35A, 35B:
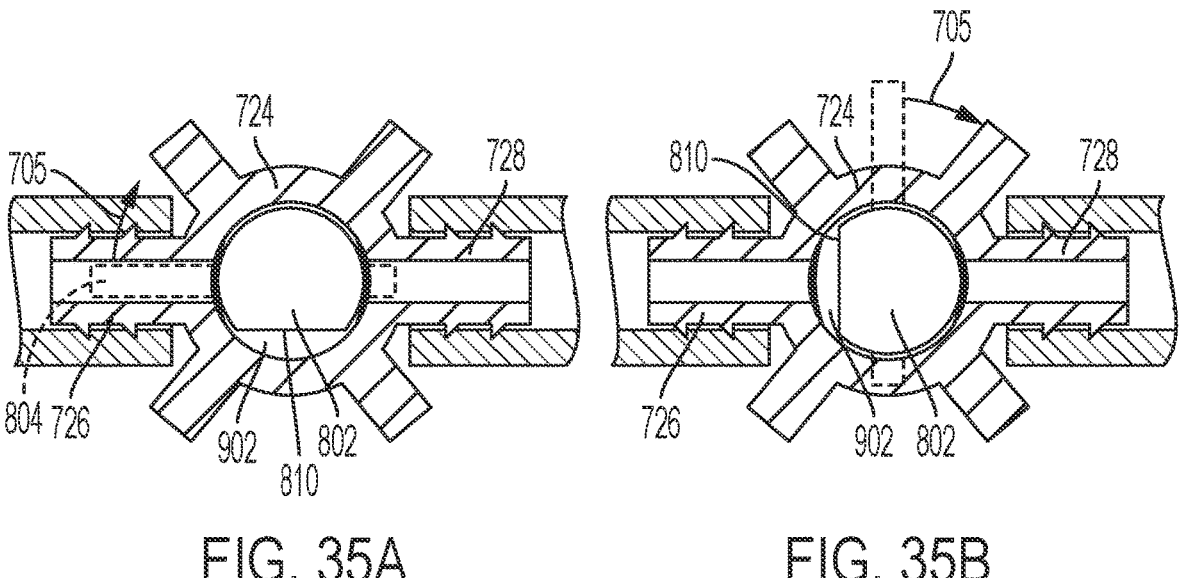
FIGS. 35A, 35B, 35C, and 35D show different top-down cutaway views of the drug pump embodiment in operation.

In FIG. 34A and FIG. 35A, plunger 802 is rotated such that plunger pin 804 is pointed towards the left in FIG. 34A and FIG. 35A. When plunger pin 304 is pointed in this direction, spring 624 causes pin 804 to engage against the lowest portion (i.e., second end 750) of pin track 718, thus causing plunger 802 to translate longitudinally to its furthest position within cavity 730 relative to housing 702. While plunger 802 is at this furthest position, distal end 814 of plunger 802 may come into contact with the closed end 762 of cavity 730 (or be located close to the closed end 762 of cavity 730), such that working chamber 902 has the smallest volume of any of the four configurations depicted in FIGS. 34A-34D and 35A-35D. Also, while plunger 802 is at this furthest position, cutout 810 is oriented out of the page in FIG. 34A, and downwards in FIG. 35A. As previously mentioned, cutout 810 and the interior wall of cavity 730 (i.e., the interior surface of side wall 724) define a working chamber 902. When cutout 810 is so oriented, the curved side wall 820 of plunger 802 presses tightly against the interior surfaces of side wall 724 surrounding inlet port 726 and outlet port 728, respectively, so as to establish a fluid-tight seal that blocks both ports. As a result, working chamber 902 is not in fluid communication with either port while in this configuration.

In FIG. 34B and FIG. 35B, plunger 802 is rotated such that plunger pin 804 is pointed into the page in FIG. 34B, and upwards in FIG. 35B. When plunger pin 804 is pointed in this direction, spring 624 causes pin 804 to engage against upwardly-sloping portion 752 of pin track 718. This causes plunger 802 to translate longitudinally out of housing 702 as plunger 802 rotates, thus increasing the volume of working chamber 902. Also, in this configuration, cutout 810 is oriented to the left in FIG. 34B and FIG. 35B, thus opening fluid communication between working chamber 902 and inlet port 726. The opened fluid communication and the increasing volume of working chamber 902 causes fluid to be sucked into working chamber 902 from inlet port 726 as pin 804 rotates (or, if the fluid is stored under pressure in the drug reservoir, allows fluid to enter working chamber 902).

Figures 35C, 35D:
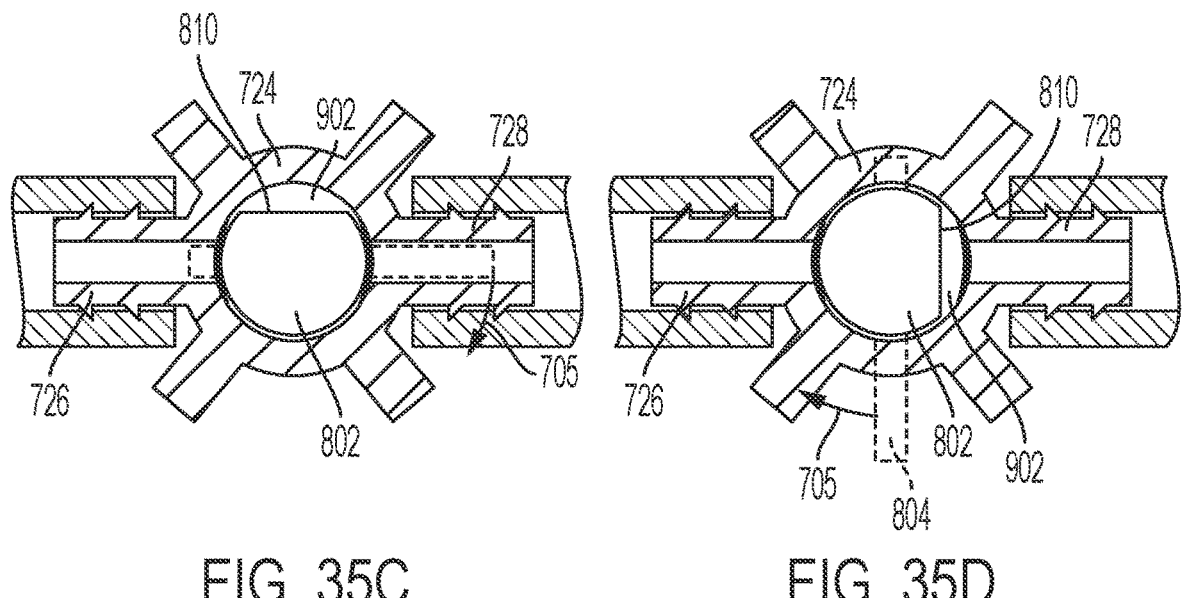

In FIG. 34C and FIG. 35C, plunger 802 is rotated such that plunger pin 804 is pointed to the right in FIG. 34C and FIG. 35C. When plunger pin 804 is pointed in this direction, spring 624 causes pin 804 to engage against the highest portion (i.e., first portion 754) of pin track 718, thus allowing plunger 802 to translate longitudinally to its furthest position out of cavity 730 relative to housing 702. When in this configuration, distal end 814 of plunger 802 is located at its shallowest position within cavity 730 such that working chamber 902 is at its largest volume of any of the four configurations depicted in FIGS. 34A-34D and 35A-35D. Also, when in this configuration, cutout 810 is oriented into the page in FIG. 34C, or upwards in FIG. 35C. When cutout 802 is so oriented, the curved side wall 820 of plunger 802 again establishes a fluid-tight seal against both inlet port 726 and outlet port 728, which means the working chamber 902 is not in fluid communication with either port.

In FIG. 34D and FIG. 35D, plunger 802 is rotated such that plunger pin 804 is pointed out of the page in FIG. 34D, or downwards in FIG. 35D. When plunger pin 804 is pointed in this direction, spring 624 causes pin 804 to engage against the downwardly-sloping portion 756 of pin track 718. This causes plunger 802 to translate longitudinally into housing 702 as plunger 802 rotates, thus decreasing the volume of working chamber 902. Also, in this configuration, cutout 910 is oriented towards the right in FIGS. 34D and 35D, thus opening fluid communication between working chamber 902 and outlet port 728. The opened fluid communication and the decreasing volume of working chamber 902 causes fluid to be expelled from working chamber 902 and out through outlet port 728 as pin 804 rotates. In this configuration, curved side wall 820 of plunger 802 continues to press tightly against inwardly offset segment 732, thus maintaining the fluid-tight seal that blocks inlet port 726.

A complete pump cycle comprises the four configurations described above in FIGS. 34A-34D and 35A-35D. For further details regarding the operation and/or configuration of pump 180, or for alternative embodiments of pump 180 that may be used, refer to U.S. Prov. App. No. 62/891,600, entitled "ROTARY PLUNGER PUMP SUBSYSTEMS" and filed on Aug. 26, 2019, the entire contents of which are hereby incorporated by reference.

Now that operation of pump 180 has been described, attention is directed back to FIGS. 25A-C. After a predetermined time (during which the drug is being pumped into the patient), face gear 230 eventually rotates into a position where one of its fins 272 come into alignment with arm 274 of latch 216. The sloped leading edge of fin 272 comes into contact with arm 274, thus pushing latch 216 to rotate in the direction of arrow 644, as depicted in FIG. 25B. This causes latch 216 to unlock secondary slide 202, as described below. As gear 232 continues to rotate, fin 272 eventually clears arm 274 of latch 216, and latch 216 moves back in the direction of arrow 646 into its neutral position under the biasing pressure of spring 222.

Figures 26A, 26B, 26C:
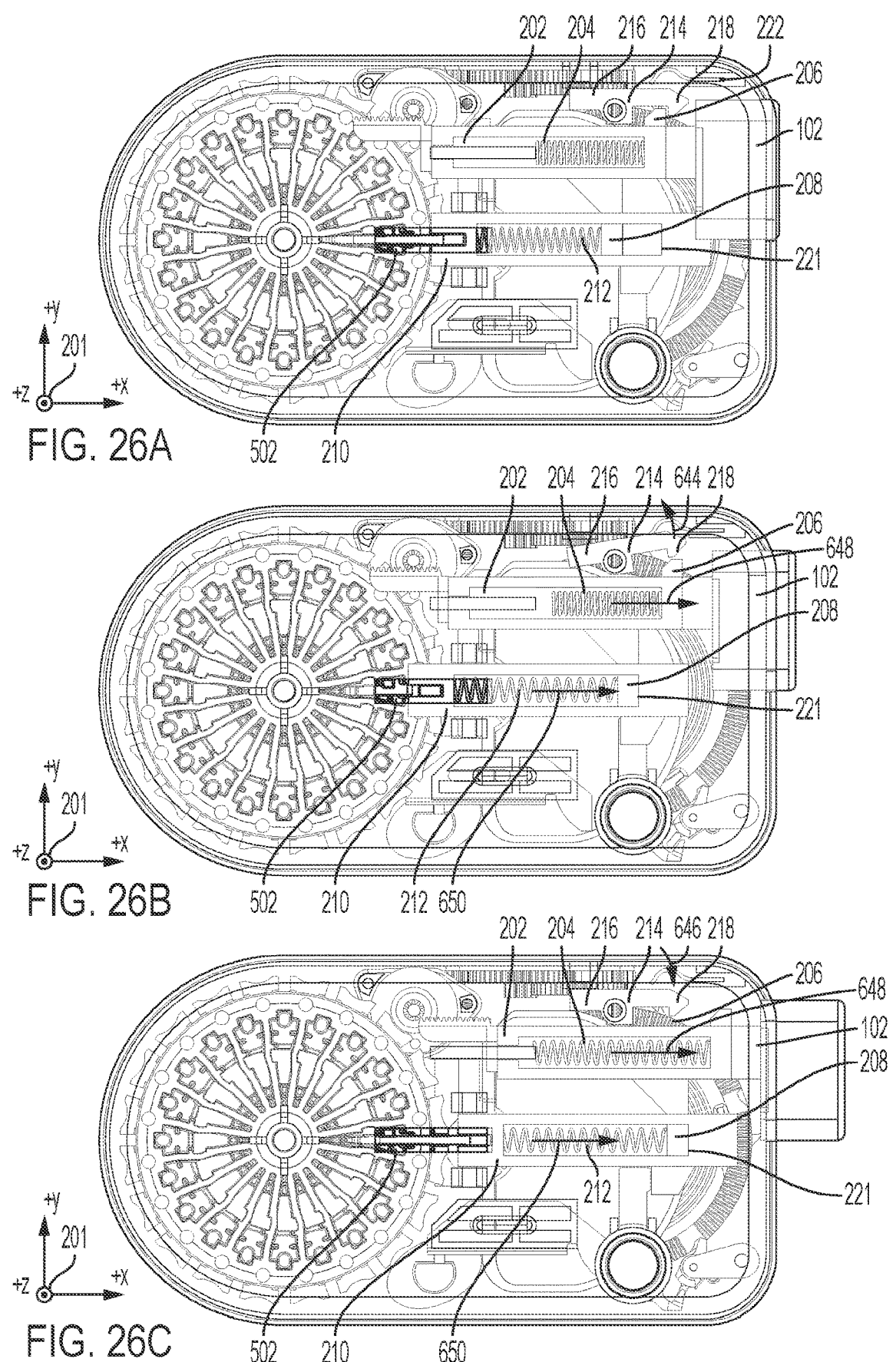
FIGS. 26A, 26B, and 26C show how release of the slide latch component releases distal movement of the secondary slide component and the primary slide component in the exemplary drug-delivery device.

FIGS. 26A-C depict the same sequence of states of device 100 as FIGS. 25A-C from above to better show how slides 202 and 210 move in response to unlocking of latch 216. FIG. 26A depicts device 100 after pawl 256 has been disengaged and face gear 230 begins unwinding, but before latch 216 is unlocked. In this state, latch tab 218 of latch 216 is positioned distal to locking tab 206 of secondary slide 202, thus preventing secondary slide 202 from translating distally under the biasing pressure of spring 204. In FIG. 26B, latch 216 rotates in the direction of arrow 644, thus clearing locking tab 206. This allows secondary slide 202 to translate distally in the direction of arrow 648 (i.e., in the +x direction) due to the biasing pressure of compressed spring 204. As secondary slide 202 translates distally, compression tab 208 contacts distal wall 221 of primary slide 210 and causes primary slide 210 to also translate distally in the direction of arrow 650 (i.e., in the +x direction). Eventually, latch 216 rotates in the direction of arrow 646 back to its neutral position (FIG. 26C) under the biasing pressure of spring 222. However, since locking tab 206 is now distal to latch tab 218, rotation of latch 216 back to its neutral position does not stop secondary slide 202 from translating distally until it hits a stop. Secondary slide 202 eventually translates back to its secondary slide distal position, and primary slide 210 eventually translates back to its primary slide distal position, as depicted in FIG. 26C.

Figures 27A, 27B, 27C:
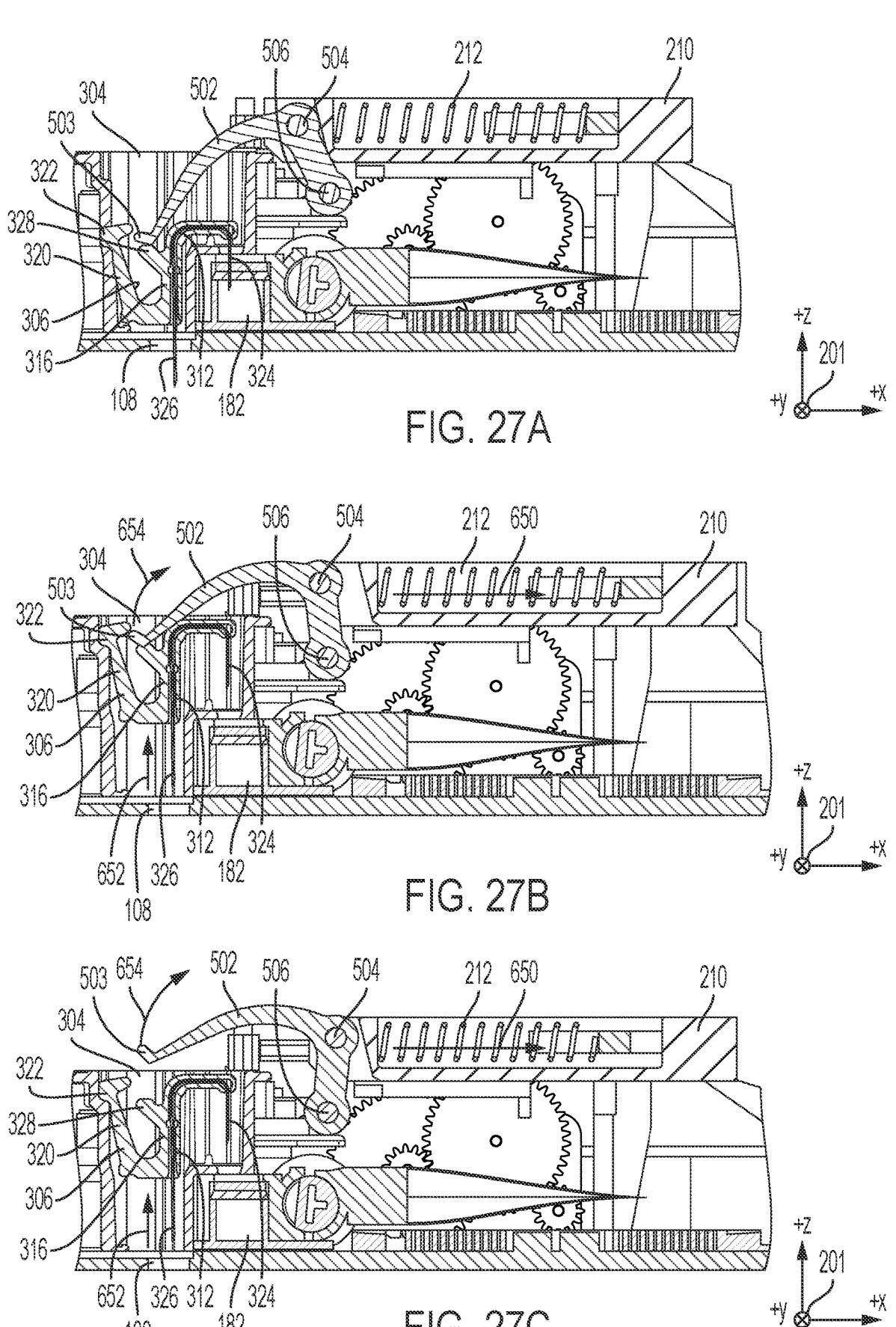
FIGS. 27A, 27B, and 27C show how distal movement of the primary slide component drives retraction of the inserted needle in the exemplary drug-delivery device.
Figure 28:
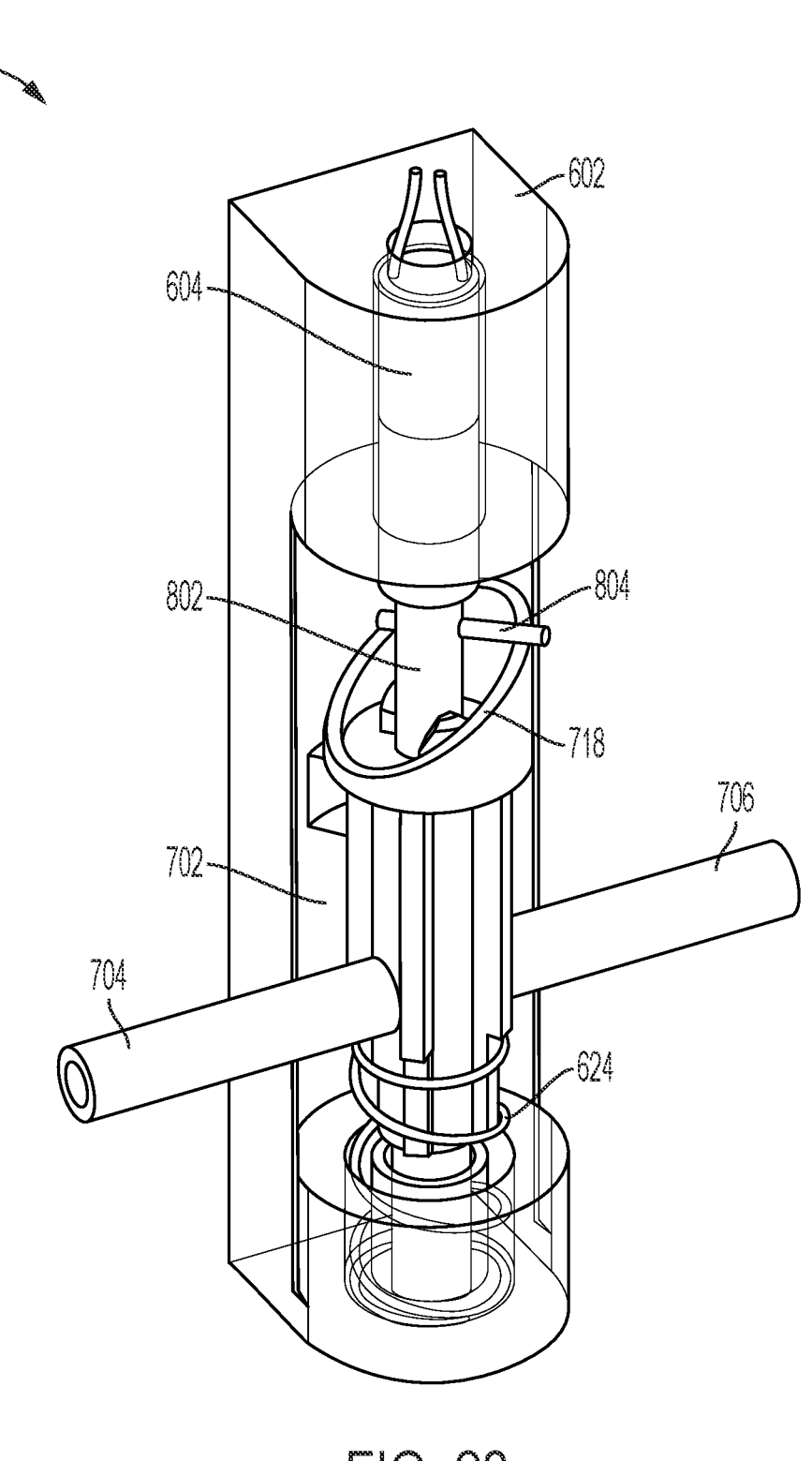
FIG. 28 shows one potential embodiment of a drug pump.

FIGS. 27A-C depict the same sequence of states of device 100 as FIGS. 25A-C and 26A-C from the side to better show how distal translation of primary slide 210 causes the needle insertion/retraction mechanism 500 to retract the needle 312. FIG. 27A depicts device 100 after pawl 256 has been disengaged and face gear 230 begins unwinding, but before latch 216 is unlocked. In this state, needle assembly 306 is in its injection position and head 503 of hammer 502 is in contact with ledge 328 of needle assembly 306. In FIG. 27B, primary slide 210 begins translating distally, thus causing hammer 502 to rotate about pin 506 in the direction of arrow 654. This rotation of hammer 502 causes head 503 to contact the underside of tang 322 of needle assembly 306 and pull the entire needle assembly upwards in the direction of arrow 652. This upwards motion retracts needle assembly 306 from its injection position back to its retracted position. In particular, first leg segment 324 of needle 312 is drawn out of drug septum 182 and second leg segment 326 is drawn out of the patient's body, thus breaking the fluid path between drug septum 182 and the patient's body. As primary slide 210 continues to translate distally and hammer 502 continues to rotate about pin 506 in the direction of arrow 654, head 503 of hammer 502 eventually disengages from tang 322 of needle assembly 306, as depicted in FIG. 27C.

The terms "first", "second", "third", "primary", "secondary", and the like, whether used in the description or in the claims, are provided for distinguishing between similar elements and not necessarily for describing a sequential or chronological order. It is to be understood that the terms so used are interchangeable under appropriate circumstances (unless clearly disclosed otherwise) and that the embodiments of the disclosure described herein are capable of operation in other sequences and/or arrangements than are described or illustrated herein.

While this invention has been described as having exemplary designs, the present invention can be further modified within the scope of this disclosure. This application is therefore intended to cover any variations, uses, or adaptations of the invention using its general principles. Further, this application is intended to cover such departures from the present disclosure as come within known or customary practice in the art to which this invention pertains.

For example, in some embodiments, the drug-delivery device may not comprise a needle cartridge holding a plurality of needle assemblies; instead, the device may comprise only a single needle assembly. Such a device may be configured for single-use only, rather than for multiple uses. This single needle assembly may be configured to be inserted and/or retracted using the insertion/retraction mechanisms discussed above.

In at least some of the above-described embodiments, one or more springs in the drug-delivery device are loaded when the user actuates a loading button. When the user then actuates a dosing button, the one or more loaded springs are released to (i) operate a drive member to drive a needle assembly in operational alignment with the drive member from a retracted position to an injection position, (ii) drive a pump to pump drug fluid from a drug reservoir through the driven needle assembly, and (iii) retract the driven needle assembly from the injection position back to the retracted position. In other embodiments however, releasing the one or more loaded springs need not drive all of functions (i) through (iii) listed above. For example, in some embodiments, releasing the one or more loaded springs (upon actuation of the dosing button) may drive only function (i) but not functions (ii) and (iii). In other embodiments, releasing the one or more loaded springs upon actuation of the dosing button may drive only functions (i) and (ii) but not (iii). In yet other embodiments, releasing the one or more loaded springs upon actuation of the dosing button may drive functions (ii) and (iii), but not function (i). In general, embodiments in which releasing the one or more springs (upon actuation of the dosing button) accomplishes any one or more of functions (i) through (iii) listed above are also within the scope of this disclosure.

Furthermore, in at least some of the above-described embodiments, the needle cartridge is indexed when the user actuates the loading button, and not when the one or more loaded springs are released when the user actuates the dosing button. In other embodiments, however, the needle cartridge may be indexed when the one or more loaded springs are released when the user actuates the dosing button.

What is claimed is:

1. A drug-delivery device, comprising:
   a housing;
   a drug reservoir within the housing configured to contain a drug fluid;
   a drive member;
   a needle assembly disposed in a retracted position within the housing;

a pump in fluid communication with the drug reservoir;
   one or more springs;
   a loading button coupled to the housing configured to be manually actuated to load the one or more springs using work done through actuation of the loading button; and
   a dosing button coupled to the housing configured to be manually actuated after actuation of the loading button to release the one or more loaded springs to:
      operate the drive member to drive the needle assembly from the retracted position to an injection position,
      drive the pump to pump the drug fluid from the drug reservoir through the driven needle assembly, and
      retract the driven needle assembly from the injection position to the retracted position.

2. The device of claim 1, further comprising the drug fluid contained within the drug reservoir.

3. The device of claim 1, wherein the needle assembly is a first needle assembly of a plurality of needle assemblies, and the plurality of needle assemblies is disposed in a needle cartridge within the housing.

4. The device of claim 3, wherein actuation of the loading button advances the needle cartridge so that a second needle assembly of the plurality of needle assemblies is moved out of operational alignment with the drive member and the first needle assembly is moved into operational alignment with the drive member.

5. The device of claim 1, further comprising an unlocking button configured to prevent actuation of the dosing button until the unlocking button is moved to an unlocked configuration.

6. The device of claim 1, wherein:
   the one or more springs comprise one or more linear springs movable between an axially expanded configuration and an axially compressed configuration;
   actuation of the loading button loads the one or more linear springs by moving the one or more linear springs to the axially compressed configuration; and
   actuation of the dosing button after actuation of the loading button releases the one or more linear springs by moving the one or more linear springs to the axially expanded configuration to operate the drive member.

7. The device of claim 1, wherein:
   the one or more springs comprise one or more clock springs movable between an unwound configuration and a wound configuration;
   actuation of the loading button loads the one or more clock springs by moving the one or more clock springs to the wound configuration using work done through actuation of the loading button; and
   actuation of the dosing button after actuation of the loading button releases the one or more clock springs by moving the one or more clock springs to the unwound configuration to drive the pump.

8. The device of claim 1, wherein:
   the one or more springs comprise a first linear spring and a second linear spring, each movable between an axially expanded configuration and an axially compressed configuration;
   the device further comprises a primary slide and a secondary slide, wherein:
      the primary slide is configured to slidably move parallel to a linear axis of the device between a first primary slide position and a second primary slide position,
      the secondary slide is configured to slidably move parallel to the linear axis between a first secondary slide position and a second secondary slide position, the primary slide is coupled to the first linear spring, and the secondary slide is coupled to both of the first linear spring and the second linear spring;

the device further comprises a blocker that, until released, is configured to prevent the primary slide from moving from the first primary slide position to the second primary slide position;

actuation of the loading button moves the secondary slide from the first secondary slide position to the second secondary slide position to move both of the first linear spring and the second linear spring to the axially compressed configuration; and actuation of the dosing button after actuation of the loading button releases the blocker to allow the first linear spring to move to the axially expanded configuration, wherein movement of the first linear spring to the axially expanded configuration moves the primary slide from the first primary slide position to the second primary slide position, and wherein movement of the primary slide to the second primary slide position operates the drive member.

9. The device of claim 8, further comprising a latch that, until released, is configured to prevent the secondary slide from moving from the second secondary slide position to the first secondary slide position after actuation of the loading button;

wherein the latch is configured to be released a predetermined time after the blocker is released to allow the second linear spring to move to the axially expanded configuration, wherein movement of the second linear spring to the axially expanded configuration moves the secondary slide from the second secondary slide position to the first secondary slide position.

10. The device of claim 9, wherein the primary slide and the secondary slide are coupled such that movement of the secondary slide from the second secondary slide position to the first secondary slide position causes the primary slide to move from the second primary slide position to the first primary slide position, wherein movement of the primary slide to the first primary slide position retracts the driven needle assembly from the injection position to the retracted position.

11. The device of claim 9, wherein the device is a re-usable device that, when the primary slide returns to the first primary slide position and the secondary slide returns to the first secondary slide position, is configured to allow a second actuation of the loading button, and then a second actuation of the dosing button after the second actuation of the loading button, to deliver a second dose of the drug fluid.

12. The device of claim 9, further comprising a clock spring rotatable between an unwound configuration and a wound configuration, a face gear rotationally locked with the clock spring, and a pawl configured to engage with the face gear, wherein actuation of the loading button loads the clock spring by rotating the face gear in a first rotational direction, wherein rotation of the face gear in the first rotational direction rotates the clock spring to the wound configuration;

wherein the pawl is configured to engage with the face gear after rotation of the clock spring to the wound configuration to prevent rotation of the face gear in a second rotational direction opposite the first rotational direction, and to prevent rotation of the clock spring to the unwound configuration;

wherein actuation of the dosing button after actuation of the loading button dis-engages the pawl from the face gear to allow the face gear to rotate in the second rotational direction, wherein rotation of the face gear in the second rotational direction rotates the clock spring to the unwound configuration; and wherein rotation of the face gear in the second rotational direction by a predetermined rotational angle releases the latch to allow the second linear spring to move to the axially expanded configuration, wherein movement of the second linear spring to the axially expanded configuration moves the secondary slide from the second secondary slide position to the first secondary slide position.

13. The device of claim 1, wherein the pump is a rotary plunger pump.

14. The device of claim 1, wherein the device is configured to use only energy released from the one or more loaded springs to operate the drive member, to drive the pump, and to retract the driven needle assembly.

15. A needle-insertion mechanism for a drug-delivery device, the mechanism comprising:

a drive member;

a needle assembly disposed in a retracted position within a housing of the drug-delivery device;

first linear spring;

second linear spring;

a primary slide configured to slidably move parallel to a linear axis of the device between a first primary slide position and a second primary slide position, wherein the primary slide is coupled to the first linear spring;

a secondary slide configured to slidably move parallel to the linear axis of the device between a first secondary slide position and a second secondary slide position, wherein the secondary slide is coupled to the first linear spring and the second linear spring;

a blocker that, until released, is configured to prevent the primary slide from moving from the first primary slide position to the second primary slide position;

a loading button configured to be manually actuated to move the secondary slide from the first secondary slide position to the second secondary slide position using work done through actuation of the loading button to compress both the first linear spring and the second linear spring; and a dosing button configured to be manually actuated after actuation of the loading button to release the blocker to allow the primary slide to move from the first primary slide position to the second primary slide position under biasing pressure from the compressed first linear spring, wherein movement of the primary slide to the second primary slide position operates the drive member to drive the needle assembly from the retracted position to an injection position.

16. The mechanism of claim 15, wherein:

the mechanism further comprises a latch that, until released, is configured to prevent the secondary slide from moving from the second secondary slide position to the first secondary slide position after actuation of the loading button; and the mechanism is configured to release the latch a predetermined time after the release of the blocker to allow the secondary slide to move from the second secondary slide position to the first secondary slide position under biasing pressure from the compressed second linear spring.

17. The mechanism of claim 16, wherein the primary slide and the secondary slide are coupled such that movement of the secondary slide from the second secondary slide position to the first secondary slide position causes the primary slide to move from the second primary slide position to the first primary slide position, wherein movement of the primary slide to the first primary slide position retracts the driven needle assembly from the injection position to the retracted position.

18. The mechanism of claim 16, wherein:

the device further comprises a clock spring rotatable between an unwound configuration and a wound configuration, a face gear rotationally locked with the clock spring, and a pawl configured to engage with the face gear;

actuation of the loading button loads the clock spring by rotating the face gear in a first rotational direction, wherein rotation of the face gear in the first rotational direction rotates the clock spring to the wound configuration;

the pawl is configured to engage with the face gear after rotation of the clock spring to the wound configuration to prevent rotation of the face gear in a second rotational direction opposite the first rotational direction, and to prevent rotation of the clock spring to the unwound configuration;

actuation of the dosing button after actuation of the loading button dis-engages the pawl from the face gear to allow the face gear to rotate in the second rotational direction, wherein rotation of the face gear in the second rotational direction rotates the clock spring to the unwound configuration; and rotation of the face gear in the second rotational direction by a predetermined rotational angle releases the latch to allow the secondary slide to move from the second secondary slide position to the first secondary slide position under biasing pressure from the compressed second linear spring.

19. A device for storing and handling needles, the device comprising:

a housing;

a drive member;

a needle cartridge holding a plurality of needle assemblies, each needle assembly disposed in a separate retracted position within the needle cartridge;

one or more springs;

a loading button coupled to the housing configured to be manually actuated to load the one or more springs using work done through actuation of the loading button, and to advance the needle cartridge so a first needle assembly of the plurality of needle assemblies is moved out of operational alignment with the drive member and a second needle assembly of the plurality of needle assemblies is moved into operational alignment with the drive member;

a dosing button coupled to the housing configured to be manually actuated after actuation of the loading button to release the one or more loaded springs to operate the drive member to drive the second needle assembly from its retracted position within the needle cartridge to an injection position;

a drug reservoir configured to contain a drug fluid; and a pump in fluid communication with the drug reservoir.

20. The device of claim 19, wherein the device is further configured to, after operating the drive member to drive the second needle assembly to the injection position, retract the second needle assembly to its retracted position using energy released from the one or more springs.

21. The device of claim 19, wherein:

the needle cartridge comprises a plurality of Geneva wheel members;

the device further comprises a Geneva wheel configured to engage with the Geneva wheel members; and the Geneva wheel is configured to rotate in response to actuation of the loading button, wherein engagement between the Geneva wheel and the Geneva wheel members causes the needle cartridge to rotate such that the first needle assembly is moved out of operational alignment with the drive member and the second needle assembly is moved into operational alignment with the drive member.

22. The device of claim 19, wherein the device is configured to, after operating the drive member to drive the second needle assembly to the injection position, drive the pump to pump the drug fluid from the drug reservoir through the second needle assembly using energy released from the one or more springs.

23. The device of claim 22, wherein the device is configured to use only energy released from the one or more loaded springs to operate the drive member and to drive the pump.

24. The device of claim 19, wherein the pump is a rotary plunger pump.

25. The device of claim 19, further comprising an unlocking button configured to prevent actuation of the dosing button until the unlocking button is moved to an unlocked configuration.

26. The device of claim 19, wherein the device is configured to use only energy released from the one or more loaded springs to operate the drive member.

27. The device of claim 20, wherein the device is configured to use only energy released from the one or more loaded springs to operate the drive member and to retract the second needle assembly.

28. A drug-delivery device, comprising:

a housing;

a drug reservoir within the housing configured to contain a drug fluid;

a pump in fluid communication with the drug reservoir;

a needle cartridge holding a plurality of needle assemblies;

one or more springs;

a loading button coupled to the housing configured to be manually actuated to load the one or more springs using work done through actuation of the loading button and to advance the needle cartridge so a first needle assembly of the plurality of needle assemblies is moved out of a dosing position within the device, and a second needle assembly of the plurality of needle assemblies is moved into the dosing position; and a dosing button coupled to the housing configured to be manually actuated after actuation of the loading button to release the one or more loaded springs to drive the pump to pump the drug fluid from the drug reservoir through the second needle assembly.

29. The device of claim 28, further comprising a drive member, wherein the dosing position is in operational alignment with the drive member, wherein:

actuation of the dosing button after actuation of the loading button releases the one or more loaded springs to operate the drive member to drive the second needle assembly to an injection position.

30. The device of claim 29, wherein the device is further configured to, after operating the drive member to drive the second needle assembly to the injection position, use energy released from the one or more springs to retract the second needle assembly to the dosing position.

31. The device of claim 30, wherein the device is configured to use only energy released from the one or more loaded springs to drive the pump, operate the drive member, and retract the second needle assembly.

32. The device of claim 29, wherein:

the one or more springs comprise one or more linear springs each movable between an axially expanded configuration and an axially compressed configuration;

actuation of the loading button moves the one or more linear springs to the axially compressed configuration using work done through actuation of the loading button; and actuation of the dosing button after actuation of the loading button releases the one or more linear springs by allowing them to move to the axially expanded configuration, wherein movement of the one or more linear springs to the axially expanded configuration operates the drive member.

33. The device of claim 29, wherein the device is configured to use only energy released from the one or more loaded springs to drive the pump and operate the drive member.

34. The device of claim 28, wherein the pump is a rotary plunger pump.

35. The device of claim 28, further comprising an unlocking button configured to prevent actuation of the dosing button until the unlocking button is moved to an unlocked configuration.

36. The device of claim 28, wherein:

the one or more springs comprise one or more clock springs movable between an unwound configuration and a wound configuration; and actuation of the loading button loads the one or more clock springs by moving the one or more clock springs to the wound configuration using work done through actuation of the loading button, and actuation of the dosing button after actuation of the loading button releases the one or more clock springs by moving the one or more clock springs to the unwound configuration to drive the pump.

37. The device of claim 28, wherein the device is configured to use only energy released from the one or more loaded springs to drive the pump.

* * * * *